(12) United States Patent
Kusumi et al.

(10) Patent No.: US 8,618,122 B2
(45) Date of Patent: Dec. 31, 2013

(54) COMPOUND HAVING ACIDIC GROUP WHICH MAY BE PROTECTED, AND USE THEREOF

(75) Inventors: Kensuke Kusumi, Osaka (JP); Masaya Kokubo, Osaka (JP); Hiroshi Ochiai, Osaka (JP); Shiro Shibayama, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/301,194

(22) PCT Filed: May 15, 2007

(86) PCT No.: PCT/JP2007/059960
§ 371 (c)(1),
(2), (4) Date: Nov. 17, 2008

(87) PCT Pub. No.: WO2007/132846
PCT Pub. Date: Nov. 22, 2007

(65) Prior Publication Data
US 2009/0192182 A1 Jul. 30, 2009

(30) Foreign Application Priority Data

May 16, 2006 (JP) ................................. 2006-136925

(51) Int. Cl.
*A61K 31/44* (2006.01)
*A61K 31/415* (2006.01)
*C07D 215/00* (2006.01)
*C07D 233/00* (2006.01)

(52) U.S. Cl.
USPC ........... 514/278; 514/396; 546/16; 548/335.1

(58) Field of Classification Search
USPC ................... 514/278, 396; 546/16; 548/335.1
See application file for complete search history.

(56) References Cited

U.S. PATENT DOCUMENTS

| 3,301,857 | A | 1/1967 | Berger et al. |
|---|---|---|---|
| 5,534,537 | A | 7/1996 | Ciccarone et al. |
| 5,962,462 | A | 10/1999 | Mills et al. |
| 6,291,469 | B1 | 9/2001 | Fisher et al. |
| 7,176,227 | B2 | 2/2007 | Yamazaki et al. |
| 7,883,991 | B1 | 2/2011 | Wu et al. |
| 2002/0018124 | A1 | 2/2002 | Mottur et al. |
| 2003/0018046 | A1 | 1/2003 | Bridger et al. |
| 2003/0187023 | A1 | 10/2003 | Kubo et al. |
| 2003/0220341 | A1 | 11/2003 | Bridger et al. |
| 2004/0019058 | A1 | 1/2004 | Bridger et al. |
| 2004/0254221 | A1 | 12/2004 | Yamazaki et al. |
| 2005/0165063 | A1 | 7/2005 | Yamazaki et al. |
| 2007/0208007 | A1 | 9/2007 | Saitou et al. |
| 2007/0208033 | A1 | 9/2007 | Yamazaki et al. |
| 2008/0009495 | A1 | 1/2008 | Kokubo et al. |
| 2009/0169567 | A1 | 7/2009 | Kokubo et al. |
| 2009/0192182 | A1 | 7/2009 | Kusumi et al. |
| 2010/0026164 | A1 | 2/2010 | Honda et al. |
| 2012/0101280 | A1 | 4/2012 | Yoshida et al. |

FOREIGN PATENT DOCUMENTS

| EP | 0 070 171 | B1 | 10/1986 |
|---|---|---|---|
| EP | 1 308 439 | A1 | 5/2003 |
| EP | 1 378 510 | A1 | 1/2004 |
| EP | 1724263 | A1 | 11/2006 |
| EP | 1961744 | A1 | 8/2008 |
| JP | 49-13184 | | 2/1974 |
| JP | 49-72332 | | 7/1974 |
| JP | 4-18092 | A | 1/1992 |
| JP | 11321508 | A | 11/1999 |
| JP | 2002-348288 | A | 12/2002 |
| JP | 2003-104884 | A | 4/2003 |
| JP | 2004-508421 | A | 3/2004 |
| JP | 2004-508422 | A | 3/2004 |
| JP | 2005-518397 | A | 6/2005 |
| WO | 95/01358 | A1 | 1/1995 |
| WO | 97/11940 | A1 | 4/1997 |
| WO | 98/25605 | A1 | 6/1998 |
| WO | 01/13917 | A1 | 3/2001 |
| WO | WO 01/14376 | A1 | 3/2001 |
| WO | 02/22599 | A2 | 3/2002 |

(Continued)

OTHER PUBLICATIONS

American Cancer Society, "Can Cancer Be Prevented?" http://www.cancer.org/docroot/CRI/content/CRI_2_4_2x_Can_cancer_be_prevented.asp, accessed May 27, 2010.*

(Continued)

*Primary Examiner* — Paul Zarek
(74) *Attorney, Agent, or Firm* — Sughrue Mion, PLLC

(57) ABSTRACT

A compound represented by general formula (I):

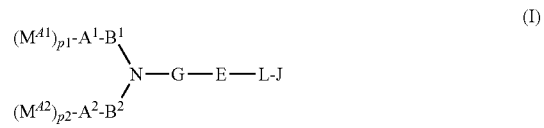

a salt thereof, a solvate thereof, or a prodrug thereof wherein all symbols are as defined in the specification. The compound of the present invention has antagonistic activity against CXCR4 and is therefore useful as a preventive and/or therapeutic agent for CXCR4-mediated diseases, for example, inflammatory and immune diseases (for example, rheumatoid arthritis, arthritis, systemic erythematosus, retinopathy, macular degeneration, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiovascular disease, metabolic diseases, cancerous diseases (for example, cancer, cancer metastasis, etc.), or an agent for regeneration therapy.

12 Claims, No Drawings

(56) References Cited

FOREIGN PATENT DOCUMENTS

| WO | 02/22600 A2 | 3/2002 |
|---|---|---|
| WO | 02/074770 A1 | 9/2002 |
| WO | 03/020721 A1 | 3/2003 |
| WO | 03/024941 A1 | 3/2003 |
| WO | 03/029218 A1 | 4/2003 |
| WO | 03/055876 A1 | 7/2003 |
| WO | 03/057698 A2 | 7/2003 |
| WO | WO 03/076443 A1 | 9/2003 |
| WO | 2004/024697 A1 | 3/2004 |
| WO | 2005/085209 A1 | 9/2005 |
| WO | 2006/022454 A1 | 3/2006 |

OTHER PUBLICATIONS

TeensHealth, "HIV and AIDS," http://kidshealth.org/teen/infections/stds/std_hiv.html, accessed May 27, 2010.*
van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*
Vippagunta SR, Brittain HG, and Grant D J, "Crystalline solids," Advanced Drug Delivery Reviews, May 2001,48(1), 3-26.*
Extended European search report dated Aug. 10, 2010, issued by the European Patent Office in a related European Application No. 05776646.1.
Office Action, dated Apr. 11, 2013, issued by the U.S. Patent and Trademark Office in counterpart U.S. Appl. No. 13/027,957.
Mashuta, M. et al. "Electron Transfer in $Fe^{II}Fe^{III}$ Model Complexes of Iron-Oxo Proteins." Journal of the American Chemical Society, 1992, vol. 114, pp. 3815-3827.
Ohkanda, Junko et al. "Design and Synthesis of Peptidomimetic Protein Farnesyltransferase Inhibitors as Anti-*Trypanosoma brucei* Agents." Journal of Medicinal Chemistry, 2004, vol. 47, pp. 432-445.
Ookubo, Takaharu et al. "*cis-µ*-1,2-Peroxo Diiron Complex: Structure and Reversible Oxygenation." Journal of the American Chemical Society, 1996, vol. 118, pp. 701-702.
Sorrell, Thomas N. et al. "Synthesis and Reactivity of Dinuclear Copper Complexes Having a *m*-Xylyl Spacer between Coordination Units" Inorganic Chemistry, 1991, vol. 30, pp. 207-210.
European Patent Office, Communication, dated Jun. 1, 2012, issued in counterpart European Application No. 06832893.9.
European Office Action, dated Aug. 4, 2011, issued in European Application No. 05776646.1.
Agarwal, R., et al., "Therapeutic potential of Curcuma longa, the golden spice of India, in drug discovery for ophthalmic diseases", Expert Opin. Drug Discov., 2009, pp. 147-158, vol. 4, No. 2.
Burger, J., et al., "CXCR4 chemokine receptor antagonists: perspectives in SCLC", Expert Opin. Investig. Drugs, 2009, 481-490, vol. 18, No. 4.
Jantzen and Robinson, "Prodrugs," "Modern Pharmaceuticals", 3rd Edition, Editors: Banker and Rhodes, 1996, p. 596.
Link, J., et al., "Clues to the etiology of autoimmune diseases through analysis of immunoglobulin genes", Arthritis Research, 2002, pp. 80-83, vol. 4, No. 2.
Lipinski, C., "Section VI—Topics in Chemistry and Drug Design", Annual Reports in Medicinal Chemistry, 1986, pp. 283-291, vol. 21.
Mehrad, B., et al., "Fibrocyte CXCR4 regulation as a therapeutic target in pulmonary fibrosis", The International Journal of Biochemistry & Cell Biology, 2009, pp. 1708-1718, vol. 41.
Mirzadegan, T., et al., "Identification of the Binding Site for a Novel Class of CCR2b Chemokine Receptor Antagonists", The Journal of Biological Chemistry, 2000, pp. 25562-25571, vol. 275, No. 33.
Mosley, C., et al., "Recent patents regarding the discovery of small molecule CXCR4 antagonists" Expert Opin. Ther. Patents, 2009, pp. 23-38, vol. 19, No. 1.
Pease, J., et al., "Chemokine receptor antagonists: part 2", Expert Opin Ther. Patents, 2009, pp. 199-221, vol. 19, No. 2.
Smith, P., et al., "New Spiropiperidines as Potent and Selective Non-Peptide Tachykinin NK2 Receptor Antagonists", J. Med. Chem., 1995, pp. 3772-3779, vol. 38, XP009135475.
Soto, H., et al., "Gene Array Analysis Comparison between Rat Collagen-induced Arthritis and Human Rheumatoid Arthritis", Scandinavian Journal of Immunology, 2008, pp. 43-57, vol. 68.
Tamamura, H. et al., "A future perspective on the development of chemokine receptor CXCR4 antagonists", Expert Opin. Drug Discov., 2008, pp. 1155-1166, vol. 3, No. 10.
Vippagunta, S/ et al., "Crystalline solids", Advanced Drug Delivery Reviews, 2001, pp. 3-26, vol. 48.
Arthritis Basics; http://www.webmed.com/osteoarthritis/guide/arthritis-basic, retrieved Apr. 26, 2010, pp. 1-4.
CA 1983:470751. See CA registry #85732-34-9 and CA registry #85732-35-0.
CA 1984: 510946. See CA registry #85732-35-0 and CA registry #85732-42-9.
CA 1989: 407312. See CA registry #85732-35-0 and CA registry #121061-07-2.
CA 2003: 282402. See CA registry #508240-62-8 and CA registry #508240-61-7.
CA 2003: 9915116. See CA registry #635713-68-7 and CA registry #635713-67-6.
Definition of Cancer; Medicine Net.com; http://www.medterms.com/script/main/art.asp?articlekey=(1 of 3), retrieved Nov. 27, 2007, pp. 1-3.
Rheumatoid Arthritis—Prevention, http://www.webmed.com/rheumatoid-arthritis/tc/rheumatoid-arthritis-prevention, retrieved Aug. 28, 2009, pp. 1-3.
International Search Report [PCT/ISA/210] issued Aug. 3, 2004, for PCT/JP2004/005493 counterpart of U.S. Appl. No. 12/332,716.
Extended European Search Report issued May 29, 2009 in European Application No. 06832893.9, counterpart of U.S. Appl. No. 12/094,100.
Supplementary European Search Report issued Jul. 9, 2010 in European Application No. 04727985.6 counterpart of U.S. Appl. No. 12/332,716.
European Office Action issued in European Application No. 06832893.9 on Oct. 20, 2010.
Mailey, Everett A. et al., "Synthesis of Derivatives of Alkylated and Arylated Piperidones and Piperidinols", Journal of Organic Chemistry, 1957, vol. 22, p. 1061-1065.
Rautio, J. et al., "Prodrugs: design and clinical applications". Nature Reviews: Drug Discovery. vol. 7. Mar. 2008. pp. 255-270.
Skerlj, R et al., Synthesis and SAR of Novel CXCR4 Antagonists that are Potent Inhibitors of T Tropic (XR) HIV-1 Replication, Bioorg. & Med. Chem. Letters. vol. 21 (2011). pp. 262-266.
Winters, G. et al. "Sintesi Di Spiroidantoine Da Chetoni Eterociclici Basici", Farmaco, Edizione Scientifica, 1970, vol. 25, No. 9, p. 681-693.
Extended European Search Report issued in European Application No. 07743395.1 on Jul. 12, 2011.
US Non-Final Office Action, issued in related U.S. Appl. No. 12/332,716 on Mar. 29, 2011.
US Non-Final Office Action, issued in related U.S. Appl. No. 12/094,100 on Jul. 27, 2011.
Notification of Reasons for Refusal dated Aug. 14, 2012 issued by the Japanese Patent Office in corresponding Japanese Patent Application No. 2007-545323.
Japanese Office Action mailed May 6, 2012 issued by the Japanese Patent Office in counterpart Japanese Patent Application No. 2006-531995.

* cited by examiner

COMPOUND HAVING ACIDIC GROUP WHICH MAY BE PROTECTED, AND USE THEREOF

TECHNICAL FIELD

The present invention relates to compounds having a basic group which is substituted with an acidic group which may have a substituent, which are useful as medicaments, and to use thereof.

More particularly, the present invention relates to (1) compounds represented by formula (I):

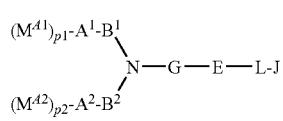

(wherein all symbols are as defined hereinafter), salts thereof, N-oxides thereof or solvates thereof, or prodrugs thereof, (2) use thereof, and (3) a method for producing the same.

BACKGROUND ART

Chemokine is known as a basic protein which has chemotaxis and an activating activity against endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, in addition to differentiation, proliferation and death of cells, cell migration is also an essential phenomenon to an immune system.

In the living body, migration of blood cells start with sifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is closely associated with such a migration of the various cells. For example, SDF-1 (Stromal cell derived factor-1) and its receptor, CXCR4 also act on various immune- and inflammatory reactions. For example, they have been reported to be associated with accumulation and activation of CD4+T cells in a synovial membrane from a human patient suffering from rheumatoid arthritis (J. Immunol., 165, 6590-6598 (2000)). In addition, in a CIA model mouse, CXCR4 inhibitor inhibited accumulation of leucocytes in a joint and dramatically reduced arthritis score (J. Immunol., 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (J. Immunol., 165, 499-508 (2000)). In a mouse bleomycin-created pulmonary disorder models, an anti-SDF-1 antibody inhibited invasion of fibrocytes to the lung and inhibited fibrosis of the lung (J. Cli. Invest., 114, 438-446 (2004)). In a mouse retinopathy model, an anti-SDF-1 antibody inhibited vascular endothelial progenitor cell invasion to the retina and inhibited neovascularisation at the retina (J. Cli. Invest., 115, 86-93 (2005)).

There has been reported that SDF-1 and its receptor, CXCR4 play an important role in maintaining hemopoietic stem cells in bone marrow J. Exp. Med., 185, 111-120 (1997), Blood, 97, 3354-3360 (2001)). Accordingly, control of SDF-1 and CXCR4 is expected to modulate recruitment of hemopoietic stem cells to peripheral blood and are useful for peripheral blood stem cell transplantation and reproduction transplantation treatment.

SDF-1 and CXCR4 are associated with infiltration of various cancer cells such as breast cancer, prostate cancer, and ovarian cancer (Nature, 410, 50-56 (2001), Cancer Res., 62, 1832-1837 (2002), Cancer Res., 62, 5930-5938 (2002)). In a model of transferring a human breast cancer cell strain into a SCID mouse, an anti-CXCR4 antibody prevented metastasis of breast cancer cells to lung (Nature, 410, 50-56 (2001)). In human ovarian epithelial tumor, highly expression of SDF-1 promotes accumulation of plasmacytoid dendritic cells and inhibits the act of bone marrow dendritic cells associated with tumor immune and suppresses tumor immune (Nat. Med., 12, 1339 (2001)). Moreover, SDF-1 is associated with proliferation and migration of non-Hodgkin's lymphoma cells, and in a model of transferring a human non-Hodgkin's lymphoma cells into a NOD/SCID mouse, an anti-CXCR4 antibody inhibited proliferation of the tumor cells and improved mouse mortality (Cancer Res., 62, 3106-3112 (2002)). A low molecular weight CXCR4 antagonist increased apoptosis of medulloblastoma transplanted in the mouse skull and inhibited tumor proliferation (Proc. Nat. Acad. Sci. USA, 100, 13513-13518 (2003)). In a lung metastasis model using malignant melanoma, the low molecular weight CXCR4 antagonist enhanced the antitumor effect of an immunostimulant and an anticancer drug (Mol Cancer Ther., 5, 2592-9 (2006)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (Development, 129, 4249-4260 (2002), Trends in Neuroscience, 25, 548-549 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (Immunology, 107, 222-232 (2002)). In a human arteriosclerotic plaque, SDF-1 was highly expressed and activated blood platelets (Circ. Res., 86, 131-138 (2000)).

SDF-1 and CXCR4 are associated with residence of hemopoietic stem cells and hemopoietic precursor cells in bone marrow, and use of AMD3100 being CXCR4 antagonist in combination with G-CSF enabled an increase in the number of hemopoietic stem cells and hemopoietic precursor cells in peripheral blood (Journal Experimental Medicine, 2001, 1307-1318 (2005). It is known that the number of neutrophiles, lymphocytes and monocytes in peripheral blood are increased by administering a low molecular weight CXCR4 antagonist to human (Blood, 102, 2728-2730 (2003)). Therefore, the immunological enhancing effect is expected to the low molecular weight CXCR4 antagonist.

In addition, the results of SDF-1/CXCR4 knock-out mice showed that SDF-1 is essential for functions of central nervous system, heart and vessels of gastrointestinal tract in addition to lymphocytes (Nature, 382, 635-639 (1996), Nature, 393, 591-594 (1998), Nature, 393, 595-599 (1998)). Accordingly, it may be associated with a disease of these tissues.

Thus, chemokine receptors are expressed at various specific cells and at a specific time. They are largely associated with the control of inflammatory- and immune-responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+ cell, HIV repetitively proliferates in a patient's body and in the event deathly destroys T cells responsible for immunological functions by necrosis. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, there are tried various preventive and therapeutic treatments for AIDS as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (Cell, 52, 631 (1985)). CD4 molecule consists of 433 amino acid residues and is expressed in macrophages, some B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (Science, 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (Nature, 382, 829 (1996), Nature, 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (Science, 272, 1955 (1996)).

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (Nature Medicine, 4, 72 (1998)).

As described above, compounds having an antagonistic activity against CXCR4 are effective, such as, for prevention and/or treatment of inflammatory and immune diseases, allergic diseases, infections, particularly HIV infection, and diseases associated with the infection, psychoneurotic diseases, cerebral diseases, cardiovascular diseases, metabolic diseases, cancerous diseases and the like. Also, the compounds are useful for cell therapy and regeneration therapy.

Heretofore, some compounds having an antagonistic activity against CXCR4 have been reported. For example, it is disclosed that a compound represented by formula (X):

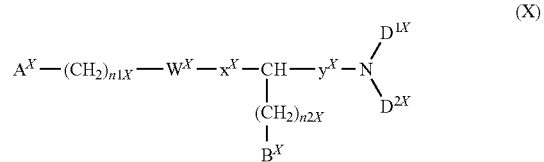

(wherein $A^X$ represents

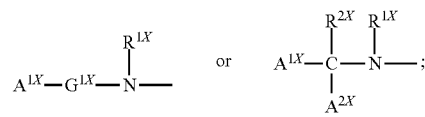

$A^{1X}$ and $A^{2X}$ each independently represents a hydrogen atom, an optionally substituted monocyclic or polycyclic heteroaromatic ring, or an optionally substituted monocyclic or polycyclic aromatic ring; $G^{1X}$ represents a single bond or $-CR^{2X}R^{3X}-$; $R^{1X}$, $R^{2X}$, and $R^{3X}$ represent an optionally substituted alkyl group having 1 to 6 carbon atom(s), etc.; $W^X$ represents an optionally substituted alkylene group having 1 to 7 carbon atom(s), an optionally substituted monocyclic or polycyclic heteroaromatic ring, an optionally substituted monocyclic or polycyclic aromatic ring, etc.; $x^X$ represents $-z^{1X}-CO-z^{2X}-$; $z^{1X}$ and $z^{2X}$ each independently represents a single bond or $NR^{13X}$, etc.; $y^X$ represents $-CO-$; $D^{1X}$ and $D^{2X}$ each independently represents a hydrogen atom or $-G^{2X}-R^{4X}$; $G^{2X}$ represents an optionally substituted alkylene group having 1 to 15 carbon atom(s), etc.; $R^{4X}$ represents a hydrogen atom, an optionally substituted monocyclic or polycyclic heteroaromatic ring, or an optionally substituted monocyclic or polycyclic aromatic ring; n2X represents 0 to 4; n1X represents 0 to 3; $B^X$ represents $-NR^{6X}R^{7X}$; and only required portions were extracted with respect to definition of each group), or a pharmaceutically acceptable salt thereof has an antagonistic activity against CXCR4 (see WO 2003/029218 pamphlet).

It is disclosed that a compound represented by formula (Y):

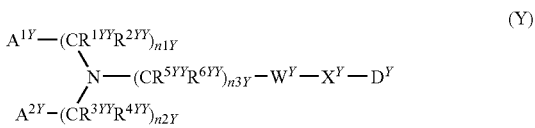

(wherein n1Y, n2Y, and n3Y represent 0 to 3; $R^{1YY}$, $R^{2YY}$, $R^{3YY}$, $R^{4YY}$, $R^{5YY}$, and $R^{6YY}$ each independently represents a hydrogen atom, or an optionally substituted alkyl group having 1 to 15 carbon atom(s), etc.; $A^{1Y}$ and $A^{2Y}$ each independently represents an optionally substituted monocyclic or polycyclic heteroaromatic ring, etc.; $W^Y$ represents an optionally substituted alkylene group having 1 to 15 carbon atom(s), etc.; $X^Y$ represents O, $CH_2$, or $NR^{11Y}$; and $D^Y$ represents -$Q^Y$-$Y^Y$—$B^Y$ and, $Q^Y$ represents a single bond or —CO— when $X^Y$ is $NR^{11Y}$, etc. and $Y^Y$ represents —$(CR^{18Y}R^{19Y})_{m3Y}$—, $R^{18Y}$ and $R^{19Y}$ each independently represents a hydrogen atom, or an optionally substituted alkyl group having 1 to 15 carbon atom(s), etc. m3Y represents 0 to 6, etc.; $B^Y$ represents —$NR^{25Y}R^{26Y}$; and $R^{25Y}$ and $R^{26Y}$ represent a hydrogen atom, an optionally substituted alkyl group having 1 to 15 carbon atom(s) when $X^Y$ is not $CH_2$, etc., and only required portions were extracted with respect to definition of each group), or a pharmaceutically acceptable salt thereof or a prodrug thereof has an antagonistic activity against CXCR4 (see WO 2004/024697 pamphlet).

It is also disclosed that a compound represented by formula (Z):

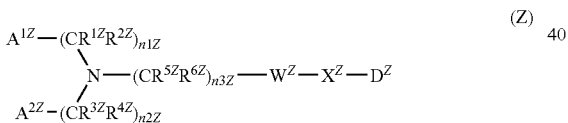

(wherein n1Z, n2Z and n3Z represent 0 to 3; $R^{1Z}$, $R^{2Z}$, $R^{3Z}$, $R^{4Z}$, $R^{5Z}$ and $R^{6Z}$ each independently represents a hydrogen atom, an optionally substituted alkyl group having 1 to 15 carbon atom(s), etc., and $R^{5Z}$ and $R^{6Z}$ may form a carbonyl group together with a carbon atom; $A^{1Z}$ and $A^{2Z}$ each independently represents an optionally substituted monocyclic or polycyclic heteroaromatic ring, etc.; $W^Z$ represents an optionally substituted benzene ring, etc.; $X^Z$ represents O, $CH_2$, or $NR^{11Z}$, etc.; $D^Z$ represents -$Q^Z$-$Y^Z$—$B^Z$; $Q^Z$ represents a single bond, —CO—, —CONH—, $NR^{12Z}$, etc. when $X^Z$ is $CH_2$; $Y^Z$ represents —$(CR^{18Z}R^{19Z})m^{3Z}$—, etc.; $R^{18Z}$ and $R^{19Z}$ each independently represents a hydrogen atom, or an optionally substituted alkyl group having 1 to 15 carbon atom(s), etc.; $m^{3Z}$ represents 0 to 6; $B^Z$ represents —$NR^{25Z}R^{26Z}$; and $R^{25Z}$ and $R^{26Z}$ represent a hydrogen atom, or an optionally substituted alkyl group having 1 to 15 carbon atom(s), etc. when $X^Z$ is not $CH_2$, and only required portions were extracted with respect to definition of each group), or a pharmaceutically acceptable salt or a prodrug thereof has an antagonistic activity against CXCR4 (see WO2005/085209 pamphlet).

It is also disclosed that a compound represented by formula (V):

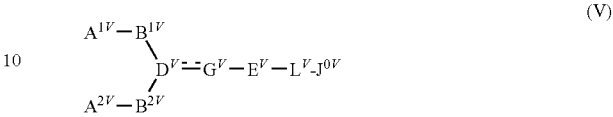

(wherein $A^{1V}$ and $A^{2V}$ each independently represents a group having a basic group; $B^{1V}$ and $B^{2V}$ each independently represents a bond or a spacer having a main chain of 1 to 4 atom(s); $E^V$ represents a spacer having a main chain of 1 to 10 atom(s); L represents a bond or a spacer having a main chain of 1 to 10 atom(s); $J^{0V}$ represents (1) an aliphatic hydrocarbon group which is substituted with a group having a basic group, and also may have a substituent(s), (2) a cyclic group which is substituted with a group having a basic group, and also may have a substituent(s), (3) a spiro-bound cyclic group which may be substituted with a group having a basic group, and also may have a substituent(s), or (4) a bridged cyclic group which may be substituted with a group having a basic group, and also may have a substituent(s), and only required portions were extracted with respect to definition of each group), or a pharmaceutically acceptable salt or a prodrug thereof has an antagonistic activity against CXCR4 (see WO 2006/022454 pamphlet).

Patent Literature 1 WO2003/029218
Patent Literature 2 WO2004/024697
Patent Literature 3 WO2005/085209
Patent Literature 4 WO2006/022454

DISCLOSURE OF THE INVENTION

Problems to be Solved by the Invention

It is earnestly desired to develop an antagonist of CXCR4, which is useful as a preventive and/or therapeutic agent for inflammatory and immune diseases (for example, rheumatoid arthritis, arthritis, systemic erythematosus, retinopathy, macular degeneration, pulmonary fibrosis, rejection of transplanted organ, etc.), allergic diseases, infections (for example, human immunodeficiency virus infection, acquired immunodeficiency syndrome, etc.), cancerous diseases (for example, cancer, cancer metastasis, etc.), cardiac/vascular diseases (for example, arteriosclerosis, myocardial infarction, stenocardia, cerebral infarction, chronic arterial occlusive disease, etc.), or an agent for regeneration therapy, and is also safe with less side effects.

Means for Solving the Problems

The present inventors have intensively studied so as to find a compound which has decreased risk of side effects and also has an anti-CXCR4 antagonic activity with excellent oral absorption and, surprisingly, have found a compound having an acidic group optionally protected by a protective group capable of decreasing a basic group introduced therein, namely, a below-described compound represented by formula (I) can attain the object of the present invention, and thus the present invention has been completed. Specifically, they have found that a compound having a basic group substituted with a group having an acidic group decreases a risk of side effects and attained the object of improving oral absorption by converting the compound into a prodrug.

Thus, the present invention relates to:

[1] A compound represented by formula (I):

$$(M^{A1})_{p1}-A^1-B^1$$
$$\phantom{(M^{A1})_{p1}-A^1-B^1}\diagdown$$
$$\phantom{(M^{A1})_{p1}-A^1-B^1xxxx}N-G-E-L-J \quad (I)$$
$$\phantom{(M^{A1})_{p1}-A^1-B^1}\diagup$$
$$(M^{A2})_{p2}-A^2-B^2$$

wherein $M^{A1}$ and $M^{A2}$ each independently represents a group having an acidic group which may be protected by a protective group;

$A^1$ and $A^2$ each independently represents a group having a basic group;

$B^1$ and $B^2$ each independently represents a bond or a spacer having a main chain of 1 to 4 atom(s);

E represents a spacer having a main chain of 1 to 10 atom(s);

L represents a bond or a spacer having a main chain of 1 to 4 atom(s);

J represents (1) an aliphatic hydrocarbon group which is substituted with a group having a basic group, and also may have a substituent(s), (2) a monocyclic or fused cyclic group which is substituted with a group having a basic group, and also may have a substituent(s), (3) a spiro-bound cyclic group which may be substituted with a group having a basic group, and also may have a substituent(s), or (4) a bridged cyclic group which may be substituted with a group having a basic group, and also may have a substituent(s);

G represents a bond, a carbon atom which may have a substituent(s), an oxygen atom, a nitrogen atom which may have a substituent(s), an optionally oxidized sulfur atom, or -(a carbon atom which may have a substituent(s))-(a nitrogen atom which may have a substituent(s))-; and p1 and p2 each independently represents 0 or 1, provided that the sum of p1 and p2 is 1 or more, a salt thereof, an N-oxide thereof or a solvate thereof, or a prodrug thereof;

[2] The compound according to the above [1], wherein $M^{A1}$ and $M^{A2}$ each independently represents a group having an acidic group which is protected by a protective group, a salt thereof, an N-oxide thereof or a solvate thereof, or a prodrug thereof;

[3] The compound according to the above [2], wherein a group having an acidic group which may be protected by a protective group is a group having an acidic group in a prodrug modification, a salt thereof, an N-oxide thereof or a solvate thereof, or a prodrug thereof;

[4] The compound according to the above [1], wherein $M^{A1}$ and $M^{A2}$ each independently represents:

$$-(Y^1)_q\text{-}Z^A \quad \text{or} \quad (a)$$

$$-(Y^2)_n-\!\!\!\overset{\frown}{\underset{\smile}{D}}\!\!\!-(Y^3)_m\text{-}Z^A \quad (b)$$

wherein $Y^1$ represents a methylene group which may have 1 to 2 substituent(s), an ethenylene group which may have 1 to 2 substituent(s), an ethynylene group, —C(O)—, —O—, —S—, —S(O)—, or —SO$_2$—;

$Y^2$ and $Y^3$ each independently represents a bond, a methylene group which may have 1 to 2 substituent(s), an ethenylene group which may have 1 to 2 substituent(s), an ethynylene group, —C(O)—, —O—, —S—, —S(O)—, or —SO$_2$—;

$Z^A$ represents (1) a carboxyl group which may be protected by a protective group, (2) a sulfo group which may be protected by a protective group, or (3) a phosphono group which may be protected by a protective group;

ring D represents a monocyclic cyclic group which may have a substituent(s);

q represents an integer of 1 to 6; and n and m each independently represents 0 or an integer of 1 to 4, provided that when q represents an integer of 2 or more, a plurality of $Y^1$ may be the same or different, when n represents an integer of 2 or more, a plurality of $Y^2$ may be the same or different, when m represents 2 or more, a plurality of $Y^3$ may be the same or different, and the sum of n and m is 4 or less;

a salt thereof, an N-oxide thereof or a solvate thereof, or a prodrug thereof;

[5] The compound according to the above [4], wherein $Y^1$ is a methylene group which may have 1 to 2 substituent(s), a salt thereof, an N-oxide thereof or a solvate thereof, or a prodrug thereof;

[6] The compound according to the above [4], wherein the ring D is C3-8 monocyclic carbocyclic ring which may have a substituent(s), a salt thereof, an N-oxide thereof or a solvate thereof, or a prodrug thereof;

[7] The compound according to the above [4], wherein $Z^A$ is a carboxyl group which may be protected by a protective group, a salt thereof, an N-oxide thereof or a solvate thereof, or a prodrug thereof;

[8] The compound according to the above [1], wherein $A^1$ and $A^2$ each independently represents a nitrogen-containing heterocyclic ring which may have a substituent(s), a salt thereof, an N-oxide thereof or a solvate thereof, or a prodrug thereof;

[9] The compound according to the above [8], wherein the nitrogen-containing heterocyclic ring is an imidazole, benzimidazole, or pyridine ring, a salt thereof, an N-oxide thereof or a solvate thereof, or a prodrug thereof;

[10] The compound according to the above [1], wherein $B^1$ and $B^2$ each independently represents —CO—, —SO$_2$—, or —CH$_2$—, a salt thereof, an N-oxide thereof or a solvate thereof, or a prodrug thereof;

[11] The compound according to the above [1], wherein G is —CO—, —SO$_2$—, or —CH$_2$—, a salt thereof, an N-oxide thereof or a solvate thereof, or a prodrug thereof;

[12] The compound according to the above [1], wherein E is a divalent 3- to 8-membered monocyclic cyclic group which may have a substituent(s), or a divalent 9- to 10-membered fused cyclic group which may have a substituent(s), a salt thereof, an N-oxide thereof or a solvate thereof, or a prodrug thereof;

[13] The compound according to the above [12], wherein the 3- to 8-membered monocyclic cyclic group is benzene, a salt thereof, an N-oxide thereof or a solvate thereof, or a prodrug thereof;

[14] The compound according to the above [1], wherein L is —CH$_2$—, or —CO—, a salt thereof, an N-oxide thereof or a solvate thereof, or a prodrug thereof;

[15] The compound according to the above [1], wherein

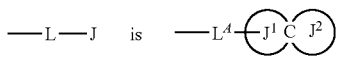

wherein ring $J^1$ and ring $J^2$ optionally have a substituent(s), $L^A$ represents -(an aliphatic hydrocarbon group having 1 to 3 carbon atom(s) which may have a substituent(s))-(a nitrogen atom which may have a substituent(s))- or a divalent aliphatic hydrocarbon group having 1 to 4 carbon atom(s) which may have a substituent(s), (a) when $L^A$ is -(aliphatic hydrocarbon group having 1 to 3 carbon atom(s) which may have a substituent(s))-(nitrogen atom which may have a substituent(s))-, ring $J^1$ represents (i) a C3-10 monocyclic or bicyclic carbocyclic ring, or (ii) a 3- to 10-membered monocyclic or bicyclic heterocyclic ring consisting of a carbon atom, an oxygen atom and/or an optionally oxidized sulfur atom, (b) when $L^A$ is a divalent aliphatic hydrocarbon group having 1 to 4 carbon atom(s) which may have a substituent(s), ring $J^1$ represents a 3- to 10-membered monocyclic or bicyclic heterocyclic ring which has at least one nitrogen atom and also optionally has an oxygen atom and/or an optionally oxidized sulfur atom, and ring $J^2$ represents (i) a C3-10 monocyclic or bicyclic carbocyclic ring substituted with a group having a basic group, (ii) 3- to 10-membered monocyclic or bicyclic heterocyclic ring consisting of a carbon atom, an oxygen atom and/or an optionally oxidized sulfur atom which is substituted with a group having a basic group, or (iii) a 3- to 10-membered monocyclic or bicyclic heterocyclic ring which has at least one nitrogen atom and also optionally has an oxygen atom, or an optionally oxidized sulfur atom which is optionally substituted with a group having a basic group, a salt thereof, an N-oxide thereof or a solvate thereof, or a prodrug thereof;

[16] The compound according to the above [15], wherein

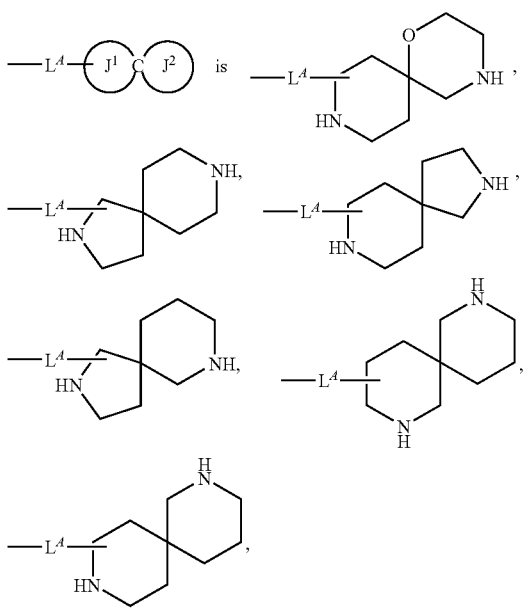

provided that $L^A$ optionally binds to a nitrogen atom of —NH— and the nitrogen atom of —NH— optionally has a substituent(s), a salt thereof, an N-oxide thereof or a solvate thereof, or a prodrug thereof;

[17] The compound according to the above [1], wherein formula (I) is formula (I-1):

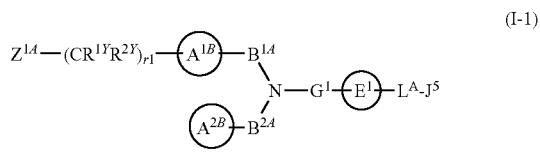

wherein ring $A^{1B}$ and ring $A^{2B}$ each independently represents an imidazole, benzimidazole, or pyridine ring which may have a substituent(s);

$B^{1A}$ and $B^{2A}$ each independently represents —CO—, —SO$_2$—, or —CH$_2$—; $G^1$ represents —CO—, —SO$_2$—, or —CH$_2$—;

ring $E^1$ represents a divalent 3- to 8-membered monocyclic cyclic group which may have a substituent(s), or a divalent 9- to 10-membered fused cyclic group which may have a substituent(s);

$L^A$ has the same meaning as described in the above [15];

$J^5$ represents a spiro-bound cyclic group which may be substituted with a group having a basic group, and also may have a substituent(s);

$Z^{1A}$ represents a carboxyl group which may be protected by a protective group;

$R^{1Y}$ and $R^{2Y}$ each independently represents a hydrogen atom or a substituent(s); and r1 represents an integer of 1 to 4, a salt thereof, an N-oxide thereof or a solvate thereof, or a prodrug thereof;

[18] The compound according to the above [17], wherein $Z^{1A}$ is a carboxyl group which may be protected by a hydrocarbon group which may have a substituent(s), a salt thereof, an N-oxide thereof or a solvate thereof, or a prodrug thereof;

[19] The compound according to the above [18], wherein the substituent(s) in $Z^{1A}$ is (1) absent, (2) an aminocarbonyl group substituted with a hydrocarbon group, or (3) a 5- or 6-membered heterocyclic group which may have a substituent(s) and also has, in addition to a carbon atom, 1 to 4 hetero atom(s) selected from an oxygen atom, a sulfur atom and/or a nitrogen atom, a salt thereof, an N-oxide thereof or a solvate thereof, or a prodrug thereof;

[20] The compound according to the above [17], wherein formula (I-1) is formula (I-1-1):

(I-1-1)

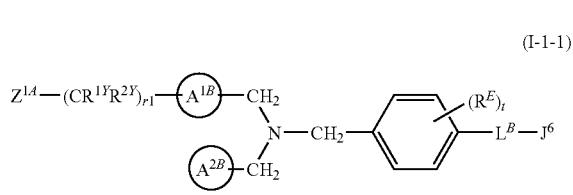

wherein $R^E$ represents a halogen atom, an —O-aliphatic hydrocarbon group, or an aliphatic hydrocarbon group, t represents 0 or an integer of 1 to 2 and, when t represents 2, two $R^E$ may be the same or different, $L^B$ represents —CO—, —CH$_2$—, —CO—CO—, —CO—CH$_2$—, —CH$_2$—CO—, or —CH$_2$—CH$_2$—, $J^6$ represents:

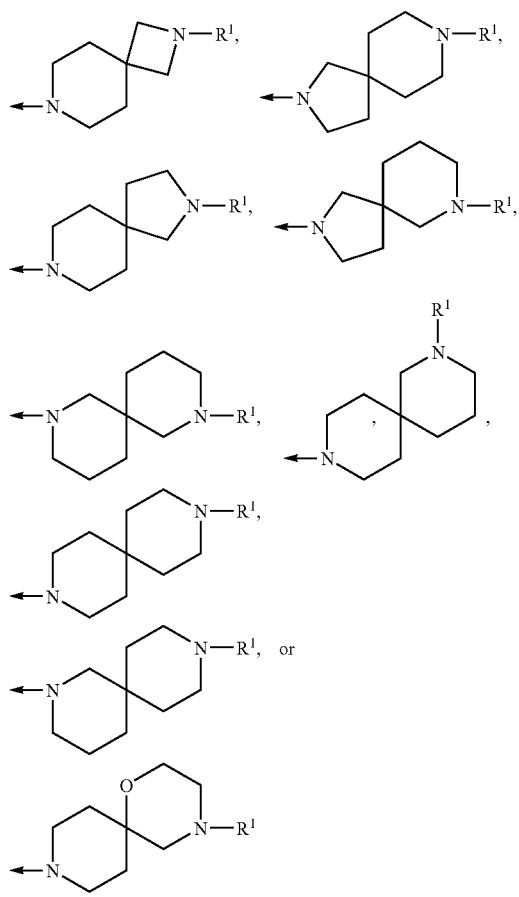

wherein an arrow binds to $L^B$, $R^1$ represents a hydrogen atom or, substituent(s), and other symbols are as defined in the above 17, a salt thereof, an N-oxide thereof or a solvate thereof, or a prodrug thereof;

[21] The compound according to the above [20], wherein $R^1$ is a C4-7 monocyclic carbocyclic ring or a C1-8 alkyl group, a salt thereof, an N-oxide thereof or a solvate thereof, or a prodrug thereof;

[22] The compound according to the above [20], wherein $Z^{1A}$ is a carboxyl group optionally protected by a C1-8 alkyl group, a salt thereof, an N-oxide thereof or a solvate thereof, or a prodrug thereof;

[23] The compound according to the above [1], which is (2-{[{4-[(8-cyclohexyl-2,8-diazaspiro[4.5]dec-2-yl)methyl] benzyl}(1H-imidazol-2-ylmethyl)amino]methyl}-1H-imidazol-1-yl)acetic acid,
ethyl (2-{[{4-[(8-cyclohexyl-2,8-diazaspiro[4.5]dec-2-yl) methyl]benzyl}(1H-imidazol-2-ylmethyl)amino]methyl}-1H-imidazol-1-yl)acetate,
ethyl 3-(2-{[{4-[(8-cyclohexyl-2,8-diazaspiro[4.5]dec-2-yl) methyl]benzyl}(1H-imidazol-2-ylmethyl)amino]methyl}-1H-imidazol-1-yl)propanoate,
3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic acid,
1-{[(cyclohexyloxy)carbonyl]oxy}ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate,
ethyl 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoate,
4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoic acid,
ethyl 4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoate, or
4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoic acid,
a salt thereof, an N-oxide thereof or a solvate thereof, or a prodrug thereof;

[24] A pharmaceutical composition comprising the compound represented by formula (I) according to the above [1], a salt thereof, an N-oxide thereof or a solvate thereof, or a prodrug thereof;

[25] The pharmaceutical composition according to the above [24], which is a CXCR4 antagonist;

[26] The pharmaceutical composition according to the above [24], which is preventive and/or therapeutic agent for CXCR4-mediated diseases, or an agent for regeneration therapy;

[27] The pharmaceutical composition according to the above [26], wherein the CXCR4-mediated disease is human immunodeficiency virus infection, acquired immunodeficiency syndrome, cancer, cancer metastasis, rheumatoid arthritis, arthritis, retinopathy, macular degeneration, pulmonary fibrosis, asthma, ischemic diseases, systemic erythematosus or transplanted organ rejection, or the agent for regeneration therapy is an agent for a transplantation medical treatment, or an agent for recruitment of hemopoietic stem cells to peripheral blood;

[28] The pharmaceutical composition according to the above [27], wherein the CXCR4-mediated disease is human immunodeficiency virus infection;

[29] A pharmaceutical comprising the compound represented by formula (I) according to the above [1], a salt thereof, an N-oxide thereof or a solvate thereof, or a prodrug thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, short interfering RNA targeting a HIV-related factor, vaccine of HIV, and immunostimulant:

[30] The pharmaceutical composition according to the above [25], which is preventive and/or therapeutic agent for cancerous diseases;

[31] A pharmaceutical comprising a compound represented by formula (I) according to the above [1], a salt thereof, an N-oxide thereof or a solvate thereof, or a prodrug thereof, and one or more kinds selected from anticancer drug, antimetabolite, antibiotic, antimitotic drug, platinum complex, plant-derived antineoplastic drug, anticancerous hormone, immunostimulant, interferon, biologics capable of performing T cell activation, and neovascularisation inhibitor;

[32] A method for antagonizing CXCR4 in a mammal, comprising administering an effective dosage of a compound represented by formula (I) according to the above [1], a salt thereof, an N-oxide thereof or a solvate thereof, or a prodrug thereof to the mammal;

[33] A method of prevention and/or treatment for CXCR4-mediated diseases in a mammal, comprising administering an effective dosage of a compound represented by formula (I) according to the above [1], a salt thereof, an N-oxide thereof or a solvate thereof, or a prodrug thereof to the mammal;

[34] Use of a compound represented by formula (I) according to the above [1], a salt thereof, an N-oxide thereof or a solvate thereof or a prodrug thereof for the preparation of a CXCR4 antagonist; and

[35] Use of a compound represented by formula (I) according to the above [1], a salt thereof, an N-oxide thereof or a solvate thereof or a prodrug thereof for the preparation of preventive and/or therapeutic agent for CXCR4-mediated diseases.

Effect of the Invention

The compound of the present invention has an antagonistic activity against CXCR4 and is therefore useful as a preventive and/or therapeutic agent for diseases mediated by CXCR4, namely, CXCR4-mediated diseases.

BEST MODE FOR CARRYING OUT THE INVENTION

In the present specification, "bond" means to directly bind without mediating the other atom therebetween.

In the present specification, "cyclic group" includes, for example, a monocyclic or fused cyclic group, a bridged cyclic group, a spiro-bound cyclic group and the like. The "monocyclic or fused cyclic group" herein includes, for example, a monocyclic or fused carbocyclic ring, a monocyclic or fused heterocyclic ring and the like. The "monocyclic or fused carbocyclic ring" includes a C3-15 monocyclic or fused carbocyclic ring. The "C3-15 monocyclic or fused carbocyclic ring" includes a C3-15 monocyclic or fused unsaturated carbocyclic ring, or partially or completely saturated one thereof. Examples of the "C3-15 monocyclic or fused unsaturated carbocyclic ring, or partially or completely saturated one thereof" include, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, and 1,2,3,5,6,7-hexahydro-s-indacene rings. Among these, examples of the "C3-15 monocyclic or fused aromatic carbocyclic ring" include benzene, azulene, naphthalene, phenanthrene, anthracene rings and the like.

The "monocyclic or fused heterocyclic ring" includes, for example, a 3- to 15-membered monocyclic or fused heterocyclic ring having, as a hetero atom, 1 to 4 nitrogen atom(s), 1 to 2 oxygen atom(s) and/or 1 to 2 sulfur atom(s). Examples of the "3- to 15-membered monocyclic or fused heterocyclic ring having, as a hetero atom, 1 to 4 nitrogen atom(s), 1 to 2 oxygen atom(s) and/or 1 to 2 sulfur atom(s)" include a 3- to 15-membered monocyclic or fused unsaturated heterocyclic ring having, as a hetero atom, 1 to 4 nitrogen atom(s), 1 to 2 oxygen atom(s) and/or 1 to 2 sulfur atom(s), or partially or completely saturated one thereof. Examples of the "3- to 15-membered monocyclic or fused unsaturated heterocyclic ring having, as a hetero atom, 1 to 4 nitrogen atom(s), 1 to 2 oxygen atom(s) and/or 1 to 2 sulfur atom(s), or partially or completely saturated one thereof" include, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydro benzoazepin, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole, pyrido[2,3-b]pyrazine, pyrido[3,4-b]pyrazine, [1,3]thiazolo[4,5-b]pyrazine, thieno[2,3-b]pyrazine, 3,4-dihydro-2H-pyrazino[2,3-b][1,4]oxazine, 6,7-dihydro-5H-cyclopenta[b]pyrazine, imidazo[1,2-a]pyrazine, 6,7-dihydro-5H-cyclopenta[b]pyridine, furo[3,2-b]pyridine, pyrido[2,3-d]pyrimidine, 2,3-dihydro-1H-pyrrolo[2,3-b]pyridine, 5,6,7,8-tetrahydro-1,6-naphthylidine, 6,7,8,9-tetrahydro-5H-pyrido[2,3-d]azepine, 3,4-dihydro-2H-pyrano[3,2-c]pyridine, 2,3-dihydrofuro[3,2-c]pyridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine rings and the like. Among these, examples of the "3- to 15-membered monocyclic or fused heterocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine rings and the like.

The "bridged cyclic group" includes a bridged carbocyclic ring and a bridged heterocyclic ring. The "bridged carbocyclic ring" includes, for example, a C4-15 bridged carbocyclic ring. Examples of the "C4-15 bridged carbocyclic ring" include bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane, bicyclo[2.1.1]hexane, bicyclo[3.3.1]nonane, bicyclo[3.2.1]octane, bicyclo[3.3.2]decane ring and the like.

The "bridged heterocyclic ring" include, for example, a heterocyclic bridged ring having, as a hetero atom, 1 to 4 nitrogen atom(s), 1 to 2 oxygen atom(s) and/or 1 to 2 sulfur atom(s). Examples of the "heterocyclic bridged ring having, as a hetero atom, 1 to 4 nitrogen atom(s), 1 to 2 oxygen atom(s) and/or 1 to 2 sulfur atom(s)" include, for example, a "4- to 15-membered heterocyclic bridged ring having, as a hetero atom, 1 to 4 nitrogen atom(s), 1 to 2 oxygen atom(s) and/or 1 to 2 sulfur atom(s)". Examples of the "4- to 15-membered heterocyclic bridged ring having, as a hetero atom, 1 to 4 nitrogen atom(s), 1 to 2 oxygen atom(s) and/or 1 to 2 sulfur atom(s)" include azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, and 3,7-diazabicyclo[3.3.1]nonane rings and the like.

The "spiro-bound cyclic group" includes a spiro-bound carbocyclic ring and a spiro-bound heterocyclic ring. The "spiro-bound carbocyclic ring" includes, for example, a C7-15 spiro-bound carbocyclic ring. Examples of the "C7-15 spiro-bound carbocyclic ring" include spiro[4.4]nonane, spiro[4.5]decane, spiro[5.5]undecane, spiro[3.4]octane, spiro[3.5]nonane rings and the like.

The "spiro-bound heterocyclic ring" includes, for example, a spiro-bound heterocyclic ring having, as a hetero atom, 1 to 4 nitrogen atom(s), 1 to 2 oxygen atom(s) and/or 1 to 2 sulfur atom(s). The "spiro-bound heterocyclic ring having, as a hetero atom, 1 to 4 nitrogen atom(s), 1 to 2 oxygen atom(s) and/or 1 to 2 sulfur atom(s)" include a 7- to 15-membered spiro-bound heterocyclic ring having, as a hetero atom, 1 to 4 nitrogen atom(s), 1 to 2 oxygen atom(s) and/or 1 to 2 sulfur atom(s). Examples of the "7- to 15-membered spiro-bound heterocyclic ring having, as a hetero atom, 1 to 4 nitrogen atom(s), 1 to 2 oxygen atom(s) and/or 1 to 2 sulfur atom(s)" herein include azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane rings and the like.

In the present specification, "aliphatic hydrocarbon group" includes, for example, "linear or branched aliphatic hydrocarbon group". Examples of the "linear or branched aliphatic hydrocarbon group" include "aliphatic hydrocarbon group having 1 to 8 carbon atom(s)", and examples of "aliphatic hydrocarbon group having 1 to 8 carbon atom(s)" include C1-8 alkyl group, C2-8 alkenyl group, and C2-8 alkynyl group.

Examples of the C1-8 alkyl group include methyl, ethyl, propyl, butyl, pentyl, hexyl, heptyl, and octyl groups, and isomer groups thereof.

Examples of the C2-8 alkenyl group include vinyl, propenyl, butenyl, pentenyl, hexenyl, heptenyl, octenyl, butadienyl, pentadienyl, hexadienyl, heptadienyl, octadienyl, hexatrienyl, heptatrienyl, and octatrienyl groups, and isomer groups thereof.

Examples of the C2-8 alkynyl group include ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, and octatriynyl groups, and isomer groups thereof.

In the present specification, the "group having a basic group" represented by $A^1$ and $A^2$ is not specifically limited as long as it has a basic group. Examples thereof include (1) basic group, (2) aliphatic hydrocarbon group which is substituted with a basic group, and also may have a substituent(s), and (3) cyclic group which is substituted with a basic group, and also may have a substituent(s).

The "aliphatic hydrocarbon group" in the "aliphatic hydrocarbon group which is substituted with a basic group, and also may have a substituent(s)" has the same meaning in the above aliphatic hydrocarbon group.

The "cyclic group" in the "cyclic group which is substituted with a basic group, and also may have a substituent(s)" has the same meaning in the above cyclic group.

The "substituent" in the "aliphatic hydrocarbon group which is substituted with a basic group, and also may have a substituent(s)" or the "cyclic group which is substituted with a basic group, and also may have a substituent(s)" is not specifically limited as long as it is a substituent. Examples thereof include the following substituents defined as T.

Examples of T include:
(1) aliphatic hydrocarbon group,
(2) C1-8 alkylidene group (for example, methylidene, ethylidene, propylidene, butylidene, pentylidene, hexylidene, heptylidene, or octylidene group, and isomer thereof, etc.),
(3) cyclic group,
(4) aliphatic hydrocarbon group substituted with a cyclic group (for example, cyclopropylmethyl, cyclopentylmethyl, cyclohexylmethyl, phenylmethyl, naphthylmethyl, pyridinylmethyl, cyclopropylethyl, cyclopentylethyl, cyclohexylethyl, phenylethyl, naphthylethyl, pyridinylethyl, cyclopropylpropyl, cyclopentylpropyl, cyclohexylpropyl, phenylmethyl, phenylpropyl, naphthylpropyl, pyridinylpropyl, etc.),
(5) hydroxyl group,
(6) —O-aliphatic hydrocarbon group (for example, methoxy, ethoxy, propoxy, isopropoxy, butoxy, isobutoxy, tert-butoxy, pentoxy, hexyloxy, heptyloxy, octyloxy, propenyloxy, butenyloxy, pentenyloxy, hexenyloxy, propynyloxy, butynyloxy, pentynyloxy, hexynyloxy, etc.),
(7) —O-cyclic group (for example, cyclopropyloxy, cyclopentyloxy, cyclohexyloxy, phenoxy, naphthyloxy, pyridinyloxy, etc.),
(8) —O-aliphatic hydrocarbon-cyclic group (for example, cyclopentylmethoxy, cyclohexylmethoxy, phenylmethoxy, etc.),
(9) mercapto group,
(10) —S-aliphatic hydrocarbon group (for example, methylthio, ethylthio, propylthio, isopropylthio, butylthio, isobutylthio, tert-butylthio, pentylthio, hexylthio, heptylthio, octylthio, propenylthio, butenylthio, pentenylthio, hexenylthio, propynylthio, butynylthio, pentynylthio, hexynylthio, etc.),
(11) —S-cyclic group (for example, cyclopropylthio, cyclopentylthio, cyclohexylthio, phenylthio, naphthylthio, pyridinylthio, etc.),
(12) —S-aliphatic hydrocarbon-cyclic group (for example, cyclopentylmethylthio, cyclohexylmethylthio, phenylmethylthio, etc.),
(13) —S(O)-aliphatic hydrocarbon group (for example, methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, heptylsulfinyl, octylsulfinyl, propenylsulfinyl, butenylsulfinyl, pentenylsulfinyl, hexenylsulfinyl, propynylsulfinyl, butynylsulfinyl, pentynylsulfinyl, hexynylsulfinyl, etc.),
(14) —S(O)-cyclic group (for example, cyclopropylsulfinyl, cyclopentylsulfinyl, cyclohexylsulfinyl, phenylsulfinyl, naphthylsulfinyl, pyridinylsulfinyl, etc.),
(15) —S(O)-aliphatic hydrocarbon-cyclic group (for example, cyclopentylmethylsulfinyl, cyclohexylmethylsulfinyl, phenylmethylsulfinyl, etc.),
(16) —$SO_2$-aliphatic hydrocarbon group (for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl, etc.),
(17) —$SO_2$-cyclic group (for example, cyclopropylsulfonyl, cyclopentylsulfonyl, cyclohexylsulfonyl, phenylsulfonyl, naphthylsulfonyl, pyridinylsulfonyl, etc.),
(18) —$SO_2$-aliphatic hydrocarbon-cyclic group (for example, cyclopentylmethylsulfonyl, cyclohexylmethylsulfonyl, phenylmethylsulfonyl, etc.),
(19) —O—CO-aliphatic hydrocarbon group (for example, methanoyloxy, ethanoyloxy, propanoyloxy, isopropanoyloxy, butanoyloxy, isobutanoyloxy, tert-butanoyloxy, pentanoyloxy, hexanoyloxy, heptanoyloxy, octanoyloxy, propenoyloxy, butenoyloxy, pentenoyloxy, hexenoyloxy, propynoyloxy, butynoyloxy, pentynoyloxy, hexynoyloxy, etc.),
(20) —O—CO-cyclic group (for example, cyclopropylcarbonyloxy, cyclopentylcarbonyloxy, cyclohexylcarbonyloxy, phenylcarbonyloxy, naphthylcarbonyloxy, pyridinylcarbonyloxy, etc.),
(21) —O—CO-aliphatic hydrocarbon-cyclic group (for example, cyclopentylmethanoyloxy, cyclohexylmethanoyloxy, phenylmethanoyloxy, etc.),
(22) —CO-aliphatic hydrocarbon group (for example, methanoyl, ethanoyl, propanoyl, isopropanoyl, butanoyl, isobutanoyl, tert-butanoyl, pentanoyl, hexanoyl, heptanoyl, octanoyl, propenoyl, butenoyl, pentenoyl, hexenoyl, propynoyl, butynoyl, pentynoyl, hexynoyl, etc.),
(23) —CO-cyclic group (for example, cyclopropylcarbonyl, cyclopentylcarbonyl, cyclohexylcarbonyl, phenylcarbonyl, naphthylcarbonyl, pyridinylcarbonyl, etc.),
(24) —CO-aliphatic hydrocarbon-cyclic group (for example, cyclopentylmethanoyl, cyclohexylmethanoyl, phenylmethanoyl, etc.),

(25) oxo group,
(26) thioxo group,
(27) sulfino group,
(28) sulfo group,
(29) amino group,
(30) mono- or di-substituted amino group ("substituent" in "mono- or di-substituted amino group" herein includes, for example, (i) aliphatic hydrocarbon group, (ii) cyclic group, and (iii) aliphatic hydrocarbon group substituted with a cyclic group. Examples of "mono- or di-substituted amino group" include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-cyclohexyl-N-propylamino, etc.),
(31) sulfamoyl group,
(32) mono- or di-substituted sulfamoyl group ("substituent" in "mono- or di-substituted sulfamoyl group" include, for example, (i) aliphatic hydrocarbon group, (ii) cyclic group, and (iii) aliphatic hydrocarbon group substituted with a cyclic group. Examples of "mono- or di-substituted sulfamoyl group" include N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, N-heptylsulfamoyl, N-octylsulfamoyl, N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, N-cyclopropylsulfamoyl, N-cyclopentylsulfamoyl, N-cyclohexylsulfamoyl, N-phenylsulfamoyl, N,N-diphenylsulfamoyl, N,N-dibenzylsulfamoyl, N-phenyl-N-methylsulfamoyl, N-phenyl-N-ethylsulfamoyl, N-benzyl-N-methylsulfamoyl, N-benzyl-N-ethylsulfamoyl, N-cyclohexyl-N-propylsulfamoyl, etc.),
(33) carboxyl group,
(34) —COO-aliphatic hydrocarbon group (for example, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, heptyloxycarbonyl, octyloxycarbonyl, propenyloxycarbonyl, butenyloxycarbonyl, pentenyloxycarbonyl, hexenyloxycarbonyl, propynyloxycarbonyl, butynyloxycarbonyl, pentynyloxycarbonyl, hexynyloxycarbonyl, etc.),
(35) —COO-cyclic group (for example, cyclopropyloxycarbonyl, cyclopentyloxycarbonyl, cyclohexyloxycarbonyl, phenoxycarbonyl, naphthyloxycarbonyl, pyridinyloxycarbonyl, etc.),
(36) —COO-aliphatic hydrocarbon-cyclic group (for example, cyclopentylmethoxycarbonyl, cyclohexylmethoxycarbonyl, phenylmethoxycarbonyl, etc.),
(37) carbamoyl group,
(38) mono- or di-substituted carbamoyl group ("substituent" in "mono- or di-substituted carbamoyl group" herein includes, for example, (i) aliphatic hydrocarbon group, (ii) cyclic group, and (iii) aliphatic hydrocarbon group substituted with a cyclic group. Examples of "mono- or di-substituted carbamoyl group" include N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, N-heptylcarbamoyl, N-octylcarbamoyl, N-cyclopropylcarbamoyl, N-cyclopentylcarbamoyl, N-cyclohexylcarbamoyl, N-phenylcarbamoyl, N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, N,N-diphenylcarbamoyl, N,N-dibenzylcarbamoyl, N-phenyl-N-methylcarbamoyl, N-phenyl-N-ethylcarbamoyl, N-benzyl-N-methylcarbamoyl, N-benzyl-N-ethylcarbamoyl, etc.),
(39) —NH—CO-aliphatic hydrocarbon group (for example, methanoylamino, ethanoylamino, propanoylamino, isopropanoylamino, butanoylamino, isobutanoylamino, tert-butanoylamino, pentanoylamino, hexanoylamino, heptanoylamino, octanoylamino, propenoylamino, butenoylamino, pentenoylamino, hexenoylamino, propynoylamino, butynoylamino, pentynoylamino, hexynoylamino, etc.),
(40) —NH—CO-cyclic group (for example, cyclopropylcarbonylamino, cyclopentylcarbonylamino, cyclohexylcarbonylamino, phenylcarbonylamino, naphthylcarbonylamino, pyridinylcarbonylamino, etc.),
(41) —NH—CO-aliphatic hydrocarbon-cyclic group (for example, cyclopentylmethanoylamino, cyclohexylmethanoylamino, phenylmethanoylamino, etc.),
(42) —NH—SO$_2$-aliphatic hydrocarbon group (for example, methylsulfonylamino, ethylsulfonylamino, propylsulfonylamino, isopropylsulfonylamino, butylsulfonylamino, isobutylsulfonylamino, tert-butylsulfonylamino, pentylsulfonylamino, hexylsulfonylamino, heptylsulfonylamino, octylsulfonylamino, propenylsulfonylamino, butenylsulfonylamino, pentenylsulfonylamino, hexenylsulfonylamino, propynylsulfonylamino, butynylsulfonylamino, pentynylsulfonylamino, hexynylsulfonyl, etc.),
(43) —NH—SO$_2$-cyclic group (for example, cyclopropylsulfonylamino, cyclopentylsulfonylamino, cyclohexylsulfonylamino, phenylsulfonylamino, naphthylsulfonylamino, pyridinylsulfonyl, etc.),
(44) —NH—SO$_2$-aliphatic hydrocarbon-cyclic group (for example, cyclopentylmethylsulfonylamino, cyclohexylmethylsulfonylamino, phenylmethylsulfonyl, etc.),
(45) cyano group,
(46) hydrazino group,
(47) nitro group,
(48) nitroso group,
(49) imino group,
(50) mono-substituted imino group ("substituent" in the mono-substituted imino group includes, for example, (i) aliphatic hydrocarbon group, (ii) cyclic group, (iii) aliphatic hydrocarbon group substituted with a cyclic group, (iv) hydroxyl group, (v) —O-aliphatic hydrocarbon group, (vi) —O-cyclic group, and (vii) —O-aliphatic hydrocarbon-cyclic group. Examples of "mono-substituted imino group" include methylimino, ethylimino, propylimino, isopropylimino, butylimino, isobutylimino, (tert-butyl)imino, pentylimino, hexylimino, heptylimino, octylimino, cyclopropylimino, cyclopentylimino, cyclohexylimino, phenylimino, benzylimino, hydroxyimino, ethoxyimino, propoxyimino, isopropoxyimino, butoxyimino, cyclopentoxyimino, cyclohexyloxyimino, phenoxyimino, benzyloxyimino, etc.),
(51) halogen atom (for example, fluorine atom, chlorine atom, bromine atom, iodine atom, etc.),
(52) methyl group substituted with 1 to 3 halogen atom(s) (for example, fluoromethyl, difluoromethyl, trifluoromethyl, trichloromethyl, etc.), and

(53) methoxy group substituted with 1 to 3 halogen atom(s) (for example, fluoromethoxy, difluoromethoxy, trifluoromethoxy, trichloromethoxy, etc.). These optional substituents may be substituted on the optional substitutable position in optional substitutable number. The number of substituents is preferably from 1 to 8, and more preferably from 1 to 5. The "aliphatic hydrocarbon group" and the "cyclic group" in T are as defined above. Also, "-aliphatic hydrocarbon-" means a divalent aliphatic hydrocarbon group and includes, for example, a divalent group in which one optional hydrogen atom is further removed from the "aliphatic hydrocarbon group".

(54) formyloxy group, and

(55) formyl group.

These optional substituents may be substituted on the optional substitutable position in optional substitutable number. The number of substituents is preferably from 1 to 8, and more preferably from 1 to 5. The "aliphatic hydrocarbon group" and the "cyclic group" in T are as defined above. Also, "-aliphatic hydrocarbon-" means a divalent aliphatic hydrocarbon group and includes, for example, a divalent group in which one optional hydrogen atom is further removed from the "aliphatic hydrocarbon group".

The "basic group" of "(1) basic group", "(2) aliphatic hydrocarbon group which is substituted with a basic group, and also may have a substituent(s)", and "(3) cyclic group which is substituted with a basic group, and also may have a substituent(s)" defined as the "group having a basic group" is not specifically limited as long as it has a basic nitrogen atom. Examples thereof include (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent (s). Examples of the "substituent" in the "mono- or di-substituted amino group" herein include (1) aliphatic hydrocarbon group (which is as defined above), (2) cyclic group (which is as defined above), (3) aliphatic hydrocarbon group substituted with a cyclic group (aliphatic hydrocarbon and cyclic group are as defined above), (4) cyclic group substituted with a substituent(s) (substituent has the same meaning as in T, and cyclic group is as defined above), (5) aliphatic hydrocarbon group substituted with a substituent(s) (substituent has the same meaning as in T, and aliphatic hydrocarbon is as defined above), (6) aliphatic hydrocarbon group substituted with a cyclic group substituted with a substituent(s) (substituent has the same meaning as in T, and aliphatic hydrocarbon and cyclic groups are as defined above), and (7) substituent exemplified as the above T, and examples of the "substituent" in the "mono-, or di-substituted amino group" include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-benzyl-N-cyclohexylamino, N-cyclohexyl-N-propylamino, N-cyclohexyl-N-(3-hydroxypropyl)amino, N-(4-hydroxycyclohexyl)-N-propylamino, N-(4-hydroxycyclohexyl)-N-(3-hydroxypropyl)amino, N-(4-hydroxycyclohexyl)methyl-N-propylamino, N-cyclohexyl-N-acetylamino, N-(3-methoxypropyl)-N-propylamino, N-(2-carboxyethyl)-N-propylamino, N-(2-ethylpropyl)-N-propylamino, N-cyclohexyl-N-(methylsulfonyl)amino, N-(tetrahydropyran-4-yl)-N-propylamino, and N-(indan-2-yl)-N-propylamino.

Examples of the "substituent" in the "mono-, di- or tri-substituted amidino group" include (1) aliphatic hydrocarbon group (which is as defined above), (2) cyclic group (which is as defined above), (3) aliphatic hydrocarbon group substituted with a cyclic group (aliphatic hydrocarbon and cyclic groups are as defined above). Examples of the "mono-, di- or tri-substituted amidino group" include methylamidino, ethylamidino, propylamidino, isopropylamidino, butylamidino, isobutylamidino, tert-butylamidino, pentylamidino, hexylamidino, heptylamidino, octylamidino, N,N-dimethylamidino, N,N'-dimethylamidino, N,N,N'-trimethylamidino, N,N-diethylamidino, N,N'-diethylamidino, N,N,N'-triethylamidino, N,N-dipropylamidino, N,N'-dipropylamidino, N,N,N'-tripropylamidino, N,N-dibutylamidino, N,N'-dibutylamidino, N,N,N'-tributylamidino, N,N-dipentylamidino, N,N'-dipentylamidino, N,N,N'-tripentylamidino, N,N-dihexylamidino, N,N'-dihexylamidino, N,N,N'-trihexylamidino, N,N-diheptylamidino, N,N'-diheptylamidino, N,N,N'-triheptylamidino, N,N-dioctylamidino, N,N'-dioctylamidino, N,N,N'-trioctylamidino, N-methyl-N-ethylamidino, N-methyl-N'-ethylamidino, cyclopropylamidino, cyclopentylamidino, cyclohexylamidino, phenylamidino, N,N-diphenylamidino, N,N'-diphenylamidino, N,N,N'-triphenylamidino, N,N-dibenzylamidino, N,N'-dibenzylamidino, N,N,N'-tribenzylamidino, N-phenyl-N'-methylamidino, N-phenyl-N'-ethylamidino, N-benzyl-N-methylamidino, N-benzyl-N-ethylamidino and the like.

Examples of the "substituent" in the "mono-, di-, tri- or tetra-substituted guanidino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di-, tri- or tetra-substituted guanidino group" include, for example, methylguanidino, ethylguanidino, propylguanidino, isopropylguanidino, butylguanidino, isobutylguanidino, tert-butylguanidino, pentylguanidino, hexylguanidino, heptylguanidino, octylguanidino, N,N-dimethylguanidino, N,N'-dimethylguanidino, N,N,N'-trimethylguanidino, N,N,N',N''-tetramethylguanidino, N,N-diethylguanidino, N,N'-diethylguanidino, N,N,N'-triethylguanidino, N,N,N',N''-tetraethylguanidino, N,N-dipropylguanidino, N,N'-dipropylguanidino, N,N,N'-tripropylguanidino, N,N,N',N''-tetrapropylguanidino, N,N-dibutylguanidino, N,N'-dibutylguanidino, N,N,N'-tributylguanidino, N,N,N',N''-tetrabutylguanidino, N,N-dipentylguanidino, N,N'-dipentylguanidino, N,N,N'-tripentylguanidino, N,N,N',N''-tetrapentylguanidino, N,N-dihexylguanidino, N,N'-dihexylguanidino, N,N,N'-trihexylguanidino, N,N,N',N''-tetrahexylguanidino, N,N-diheptylguanidino, N,N'-diheptylguanidino, N,N,N'-triheptylguanidino, N,N,N',N''-tetraheptylguanidino, N,N-dioctylguanidino, N,N'-dioctylguanidino, N,N,N'-trioctylguanidino, N,N,N',N''-tetraoctylguanidino, N-methyl-N-ethylguanidino, N-methyl-N'-ethylguanidino, cyclopropylguanidino, cyclopentylguanidino, cyclohexylguanidino, phenylguanidino, N,N-diphenylguanidino, N,N'-diphenylguanidino, N,N,N'-triphenylguanidino, N,N,N',N''-tetraphenylguanidino, N,N-dibenzylguanidino, N,N'-dibenzylguanidino, N,N,N'-tribenzylguanidino, N,N,N',N''-tetrabenzylguanidino, N-phenyl-N'-methylguanidino, N-phenyl-N'-ethylguanidino, N-benzyl-N-methylguanidino, N-benzyl-N-ethylguanidino and the like.

Examples of the "substituent" in the "mono-, di- or tri-substituted hydrazino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di- or tri-substituted hydrazino group" include, for example, methylhydrazino, ethylhydrazino, propylhydrazino, isopropylhydrazino, butylhydrazino, isobutylhydrazino, tert-butylhydrazino, pentylhydrazino, hexylhydrazino, heptylhydrazino, octylhydrazino, N,N-dimethylhydrazino, N,N'-dimethylhydrazino, N,N,N'-trimethylhydrazino, N,N-diethylhydrazino, N,N'-diethylhydrazino, N,N,N'-triethylhydrazino, N,N-dipropylhydrazino, N,N'-dipropylhydrazino, N,N,N'-tripropylhydrazino, N,N-dibutylhydrazino, N,N'-dibutylhydrazino, N,N,N'-tributylhydrazino, N,N-dipentylhydrazino, N,N'-dipentylhydrazino, N,N,N'-tripentylhydrazino, N,N-dihexylhydrazino, N,N'-dihexylhydrazino, N,N,N'-trihexylhydrazino, N,N-diheptylhydrazino, N,N'-diheptylhydrazino, N,N,N'-triheptylhydrazino, N,N-dioctylhydrazino, N,N'-dioctylhydrazino, N,N,N'-trioctylhydrazino, N-methyl-N-ethylhydrazino, N-methyl-N'-ethylhydrazino, cyclopropylhydrazino, cyclopentylhydrazino, cyclohexylhydrazino, phenylhydrazino, N,N-diphenylhydrazino, N,N'-diphenylhydrazino, N,N,N'-triphenylhydrazino, N,N-dibenzylhydrazino, N,N'-dibenzylhydrazino, N,N,N'-tribenzylhydrazino, N-phenyl-N'-methylhydrazino, N-phenyl-N'-ethylhydrazino, N-benzyl-N-methylhydrazino, N-benzyl-N-ethylhydrazino and the like.

The "nitrogen-containing heterocyclic ring" in the "nitrogen-containing heterocyclic ring which may have a substituent(s)" include, for example, a heterocyclic ring which is a 3- to 15-membered monocyclic or fused heterocyclic ring having at least one nitrogen atom, a bridged heterocyclic ring, a spiro-bound heterocuclic ring and the like. Examples thereof include pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane ring and the like.

The "substituent" in the "nitrogen-containing heterocyclic ring which may have a substituent(s)" includes, other than those exemplified as for the above T, (a) aliphatic hydrocarbon group substituted with 1 to 5 substituent(s) selected from those exemplified in (5) to (26), (29) to (32) and (37) to (55) of the above T (aliphatic hydrocarbon is as defined above), (b) cyclic group substituted with 1 to 5 substituent(s) selected from those exemplified in (5) to (26), (29) to (32) and (37) to (55) of the above T (cyclic group is as defined above), (c) aliphatic hydrocarbon group substituted with "cyclic group substituted with 1 to 5 substituent(s) selected from those exemplified in (5) to (26), (29) to (32) and (37) to (55) of the above T" (aliphatic hydrocarbon is as defined above). These optional substituents may be substituted on the optional substitutable position in optional substitutable number. The number of substituents is preferably from 1 to 8, and more preferably from 1 to 5.

In the present specification, p1 and p2 each independently represent 0 or 1.

In the present specification, when p1 represents 0, $(M^{41})_{p1}$-$A^1$- represents $A^1$-.

In the present specification, when p2 represents 0, $(M^{42})_{p2}$-$A^2$- represents $A^2$-.

In the present specification, the "group having an acidic group" in the "group having an acidic group which may be protected by a protective group" represented by $M^{41}$ and $M^{42}$ is not specifically limited as long as it has an acidic group. Examples thereof include (1) acidic group, (2) aliphatic hydrocarbon group which is substituted with an acidic group, and also may have a substituent(s), (3) cyclic group which is substituted with an acidic group, and also may have a substituent(s), (4) cyclic group which is substituted with the "aliphatic hydrocarbon group which is substituted with an acidic group, and also may have a substituent(s)" described in the above (2), and also may have a substituent(s), (5) aliphatic hydrocarbon group which is substituted with the "cyclic group which is substituted with an acidic group, and also may have a substituent(s)" described in the above (3), and also may have a substituent(s)", and (6) aliphatic hydrocarbon group which is substituted with the "cyclic group which is substituted with an acidic group substituted with the "aliphatic hydrocarbon group which is substituted with an acidic group, and also may have a substituent(s)" described in the above (4), and also may have a substituent(s)".

The "aliphatic hydrocarbon group" in the "aliphatic hydrocarbon group which is substituted with an acidic group, and also may have a substituent(s)", "cyclic group which is substituted with the "aliphatic hydrocarbon group which is substituted with an acidic group, and also may have a substituent(s)", "aliphatic hydrocarbon group which is substituted with the "cyclic group which is substituted with an acidic group, and also may have a substituent(s)", and also may have a substituent(s)", and "aliphatic hydrocarbon group which is substituted with the "cyclic group which is substituted with the "aliphatic hydrocarbon group which is substituted with an acidic group, and also may have a substituent(s)" has the same meaning as described in the aliphatic hydrocarbon group, or a group in which, among carbon atoms of the main chain of the aliphatic hydrocarbon group, optional carbon atoms are substituted with an oxygen atom, a sulfur atom, a phosphorus atom and/or a nitrogen atom which may have a substituent(s) (examples of the substituent here include the substituents exemplified as for T). These optional carbon atoms may be substituted with 1 to 3 oxygen atom(s), a sulfur atom, a phosphorus atom and/or a nitrogen atom which may have a substituent(s) at the substitutable position.

The "cyclic group" in the "cyclic group which is substituted by an acidic group, and also may have a substituent(s)", "cyclic group which is substituted by an acidic group, and also may have a substituent(s) which is substituted by the aliphatic hydrocarbon group which may have a substituent(s)", "aliphatic hydrocarbon group which is substituted by an acidic group, and also is substituted by the cyclic group which may have a substituent(s), and also may have a substituent(s)", and "aliphatic hydrocarbon group which is substituted by an acidic group, and also is substituted by the aliphatic hydrocarbon group which may have a substituent(s) and also is substituted by the cyclic group which may have a substituent(s), and also may have a substituent(s) has the same meaning as described in the cyclic group.

The "substituent" in the "cyclic group which is substituted by an acidic group, and also may have a substituent(s)", "cyclic group which is substituted by an acidic group, and also may have a substituent(s) which is substituted by the aliphatic hydrocarbon group which may have a substituent(s)", "aliphatic hydrocarbon group which is substituted by an acidic group, and also is substituted by the cyclic group which may have a substituent(s), and also may have a substituent(s)", and "aliphatic hydrocarbon group which is substituted by an acidic group, and also is substituted by the aliphatic hydrocarbon group which may have a substituent(s) and also is substituted by the cyclic group which may have a substituent(s), and also may have a substituent(s)" is not specifically limited. Examples thereof include those exemplified as for T. These optional substituents may be substituted on the substitutable position in substitutable number of 1 to 5, and preferably 1 to 2.

In the present specification, the "acidic group" includes, for example, the following first and second groups.

<First Group>

Carboxyl group (—COOH), sulfo group (—SO$_3$H), sulfino group (—SO$_2$H), hydroxysulfonylamino group (—NR$^{101}$SO$_3$H(R$^{101}$ represents a hydrogen atom, or a hydrocarbon group which may have a substituent(s)), phosphono group (—P(=O)(OH)$_2$);

<Second Group>

Various Broensted acids such as phenolic hydroxyl group (—C$_6$H$_4$OH), or nitrogen-containing ring residue having a deprotonizable hydrogen atom In the present specification, "Broensted acid" in "various Broensted acids such as nitrogen-containing ring residue having a deprotonizable hydrogen atom" means a substance which gives hydrogen ion to other substances. The "nitrogen-containing ring residue having a deprotonizable hydrogen atom" in the "various Broensted acids such as nitrogen-containing ring residue having a deprotonizable hydrogen atom" includes, for example,

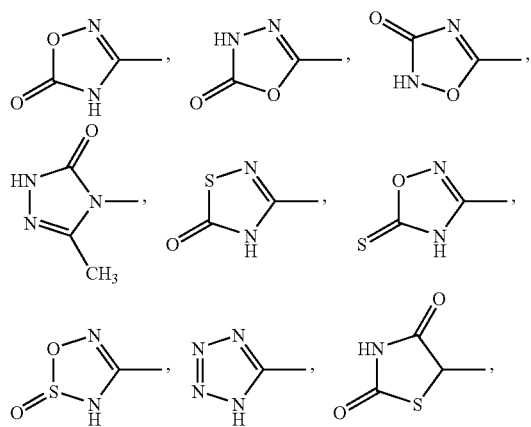

-continued

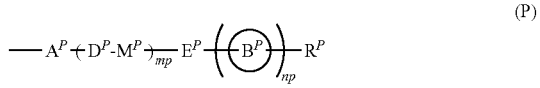

In the present specification, the "protective group" in the "group having an acidic group which may be protected by a protective group" represented by M$^{41}$ and M$^{42}$ is not specifically limited as long as it protects a group having an acidic group. Examples of the protective group of the group having an acidic group exemplified as for the first group include hydrocarbon group which may have a substituent(s), amino group which may have a substituent(s), C1-6 alkoxy group, and group represented by the following formula (P), and examples of the protective group of the group having an acidic group exemplified as for the second group include hydrocarbon group which may have a substituent (s). When the acidic group is a phosphono group, and also two hydrogen atoms of the phosphono group are protected by a hydrocarbon group which may have a substituent(s), two hydrocarbon group which may have a substituent(s) may be combined to form a C2-4 alkylene group.

Formula (P)

$$—A^P\!\!-\!\!(D^P\!-\!M^P)_{mp}\!-\!E^P\!-\!(\!(B^P)\!)_{np}\!-\!R^P \quad\quad (P)$$

(wherein A$^P$ represents an oxygen atom or an optionally substituted nitrogen atom; ring B$^P$ represents a cyclic group which may have a substituent(s); D$^P$ and E$^P$ each independently represent an optionally substituted C1-8 alkylene group, an optionally substituted C2-8 alkenylene group, an optionally substituted C2-8 alkynylene group, or a bond; M$^P$ represents a bond or a spacer having an oxygen atom, a nitrogen atom, a sulfur atom and/or a phosphorus atom in its main chain; R$^P$ represents a hydrogen atom or a substituent(s); mp represents an integer of 1 to 3 and, when mp represents 2 or more, a plurality of D$^P$ and a plurality of M$^P$ may be the same or different; and np represents 0 or an integer of 1 to 2 and, when np is 2, a plurality of rings B$^P$ may be the same or different.

In the present specification, examples of the "hydrocarbon group" in the "hydrocarbon group which may have a substituent(s)" include C1-15 alkyl group such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl group, etc.; C3-8 cycloalkyl group such as cyclopropyl, cyclobutyl, cyclopentyl, cyclohexyl group, etc.; C2-10 alkenyl group such as vinyl, allyl, 2-methylallyl, 2-butenyl, 3-butenyl, 3-octenyl group, etc.; C2-10 alkynyl group such as ethynyl, 2-propynyl, 3-hexynyl group, etc.; C3-10 cycloalkenyl group such as cyclopropenyl, cyclopentenyl, cyclohexenyl group, etc.; C6-14 aryl group such as phenyl, naphthyl group, etc.; C7-16 aralkyl group such as benzyl, phenylethyl group, etc.; and (C3-8 cycloalkyl group)-

(C1-4 alkyl group) such as cyclohexylmethyl, cyclohexylethyl, cyclohexylpropyl, 1-methyl-1-cyclohexylmethyl, cyclopropylethyl group, etc. The "substituent" in the "hydrocarbon group which may have a substituent(s)" include, for example, (1) nitro group, (2) hydroxyl group, (3) oxo group, (4) thioxo group, (5) cyano group, (6) carbamoyl group, (7) aminocarbonyl group substituted with C1-8 hydrocarbon, such as N-butylaminocarbonyl, N-cyclohexylmethylaminocarbonyl, N-butyl-N-cyclohexylmethylaminocarbonyl, N-cyclohexylaminocarbonyl, phenylaminocarbonyl group, etc., (8) carboxyl group, (9) C1-4 alkoxycarbonyl group such as methoxycarbonyl, ethoxycarbonyl group, etc., (10) sulfo group, (11) halogen atom such as fluorine atom, chlorine atom, bromine atom, iodine atom, etc., (12) C1-4 lower alkoxy group which may be substituted with a halogen atom, such as methoxy, ethoxy, propoxy, isopropoxy, butoxy, isobutoxy, sec-butoxy, tert-butoxy, difluoromethoxy, trifluoromethoxy group, etc., (13) phenoxy group, (14) halogenophenoxy group such as o-, m- or p-chlorophenoxy group, o-, m- or p-bromophenoxy, etc., (15) C1-4 lower alkylthio group such as methylthio, ethylthio, n-propylthio, isopropylthio, n-butylthio, tert-butylthio group, etc., (16) phenylthio group, (17) C1-4 lower alkylsulfinyl group such as methylsulfinyl, ethylsulfinyl group, etc., (18) C1-4 lower alkylsulfonyl group such as methylsulfonyl, ethylsulfonyl group, etc., (19) C1-4 lower acyl group such as formyl, acetyl group, etc., (20) benzoyl group, (21) 5- or 6-membered heterocyclic group which may have, in addition to a carbon atom, 1 to 4 hetero atom(s) selected from an oxygen atom, a sulfur atom and/or a nitrogen atom such as (a) halogen atom such as bromine atom, chlorine atom, fluorine atom, etc., (b) hydrocarbon group which may be substituted with an oxo or hydroxy group, such as methyl, ethyl, propyl, isopropyl, benzyl, cyclohexyl, cyclohexylmethyl, cyclohexylethyl group, etc. (the "hydrocarbon group" has the same meaning as described in the "hydrocarbon group"), (c) halogenophenoxy group such as o-, m- or p-chlorophenoxy group, o-, m- or p-bromophenoxy, etc., and (d) oxo group, for example, 2- or 3-thienyl, 2- or 3-furyl, 3-, 4- or 5-pyrazolyl, 4-tetrahydropyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl group, etc., and (22) C1-10 haloalkyl group such as difluoromethyl, trifluoromethyl, trifluoroethyl, trichloroethyl group, etc. The "hydrocarbon group which may have a substituent(s)" may have 1 to 10 substituent(s) selected from (1) to (22) in the "substituets" of the "hydrocarbon group which may have a substituent(s)". When the "hydrocarbon group" is a cycloalkyl, cycloalkenyl, aryl or aralkyl group, the hydrocarbon group may also have 1 to 4 C1-4 lower alkyl groups such as methyl, ethyl, propyl, isopropyl, butyl, etc. as substituents. When the number of substituents is 2 or more, the substituents may be the same or different.

In the present specification, examples of the "substituent" of the amino group in the "amino group which may have a substituent(s)" include those exemplified in the "hydrocarbon group which may have a substituent(s)".

In the present specification, examples of the "C1-6 alkoxy group" include methoxy, ethoxy, propoxy, butoxy, pentyloxy, hexyloxy group, etc.

In the present specification, the "cyclic group" in the "cyclic group which may have a substituent(s)" represented by ring $B^P$ includes, for example, divalent group which can be obtained by removing optional two hydrogen atoms from the "carbocyclic ring", "heterocyclic ring", or "steroid framework".

The "carbocyclic ring" as the "cyclic group" in the "cyclic group which may have a substituent(s)" represented by ring $B^P$ includes, for example, "C3-15 carbocyclic ring". The "C3-15 carbocyclic ring" includes "C3-15 monocyclic, bicyclic or tricyclic carbocyclic ring" and "C3-15 spiro-bound bicyclic carbocyclic ring and bridged bicyclic carbocyclic ring". Examples of the "C3-15 monocyclic, bicyclic or tricyclic carbocyclic ring" include cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7]annulene, heptalene, perhydroheptalene, biphenylene, as-indacene, s-indacene, acenaphthylene, acenaphthene, fluorene, phenalene, phenanthrene, anthracene rings and the like. Examples of the "C3-15 spiro-bound bicyclic carbocyclic ring and bridged bicyclic carbocyclic ring" include spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane rings and the like.

The "heterocyclic ring" as the "cyclic group" in the "cyclic group which may have a substituent(s)" represented by ring $B^P$ includes, for example, "3- to 15-membered heterocyclic ring having 1 to 5 nitrogen atom(s), 1 to 2 oxygen atom(s) and/or one sulfur atom" and the like. The "3- to 15-membered heterocyclic ring having 1 to 5 nitrogen atom(s), 1 to 2 oxygen atom(s) and/or one sulfur atom" includes "3- to 15-membered monocyclic, bicyclic or tricyclic heterocyclic ring having 1 to 5 nitrogen atom(s), 1 to 2 oxygen atom(s) and/or one sulfur atom" and "3- to 15-membered spiro-bound bicyclic heterocyclic ring and bridged bicyclic heterocyclic ring having 1 to 5 nitrogen atom(s), 1 to 2 oxygen atom(s) and/or one sulfur atom" and the like.

The "3- to 15-membered monocyclic, bicyclic or tricyclic heterocyclic ring having 1 to 5 nitrogen atom(s), 1 to 2 oxygen atom(s) and/or one sulfur atom" include, for example, pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolidine, purine, phthalazine, pteridine, naphthylidine, quinoxaline, quinazoline, cinnoline, benzoxazole, benzothiazole, benzimidazole, chromene, benzoxepin, benzoxazepine, benzoxadiazepine, benzothiepine, benzothiazepine, benzothiadiazepine, benzoazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzoazepine, tetrahydrobenzoazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chromene, chroman, benzodithiolane, benzodithiane rings and the like.

The "3- to 15-membered spiro-bound bicyclic heterocyclic ring and bridged bicyclic heterocyclic ring having 1 to 5 nitrogen atom(s), 1 to 2 oxygen atom(s) and/or one sulfur atom" include, for example, azaspiro[4.4]nonane, oxazaspiro[4.4]nonane, oxazaspiro[2.5]octane, azaspiro[4.5]decane, 1,3,8-triazaspiro[4.5]decane, 2,7-diazaspiro[4.5]decane, 1,4,9-triazaspiro[5.5]undecane, oxazaspiro[4.5]decane, azaspiro[5.5]undecane, azabicyclo[2.2.1]heptane, azabicyclo[3.1.1]heptane, azabicyclo[3.2.1]octane(8-azabicyclo[3.2.1]octane ring, etc.), azabicyclo[2.2.2]octane(2-azabicyclo[2.2.2]octane ring, etc.), azabicyclo[2.1.1]hexane(5-azabicyclo[2.1.1]hexane ring, etc.) rings and the like.

In the present specification, the "steroid framework" in the "steroid framework which may have a substituent(s)" represented by ring $B^P$ may be any one as long as it is generally called a steroid framework, and usually means a perhydro-1H-cyclopenta[a]phenanthrene framework. The "steroid framework which may have a substituent(s)" includes, for example, structures derived from cholic acid, deoxycholic acid, chenodeoxycholic acid, ursocholic acid, and ursodeoxycholic acid represented by formula ($S^P$).

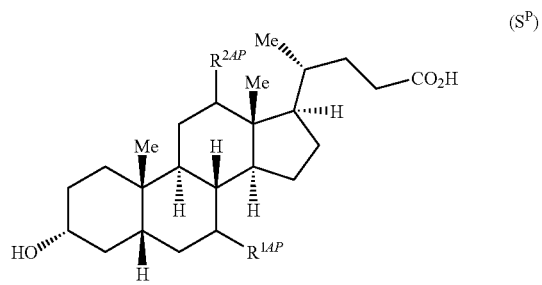

$R^{1AP}$=α-OH, $R^{2AP}$=α-OH: Cholic acid
$R^{1AP}$=H, $R^{2AP}$=α-OH: Deoxycholic acid
$R^{1AP}$=α-OH, $R^{2AP}$=H: Chenodeoxycholic acid
$R^{1AP}$=β-OH, $R^{2AP}$=α-OH: Ursocholic acid
$R^{1AP}$=β-OH, $R^{2AP}$=H: Ursodeoxycholic acid In the present specification, the "substituent" in the "cyclic group which may have a substituent(s)" represented by ring $B^P$ is not specifically limited as long as it is a substituent. The "substituent" include, for example, (1) optionally substituted C1-20 alkyl group, (2) optionally substituted C2-20 alkenyl group, (3) optionally substituted C2-20 alkynyl group, (4) optionally substituted C1-20 alkylidene group, (5) optionally substituted cyclic group, (6) oxo group, (7) hydroxyl group, (8) optionally substituted C1-20 alkyloxy group, (9) optionally substituted C2-20 alkenyloxy group, (10) optionally substituted C2-20 alkynyloxy group, (11) hydroxyl group which may be protected by an optionally substituted cyclic group, (12) optionally substituted C1-20 acyloxy group, (13) thioxo group, (14) mercapto group, (15) optionally substituted C1-20 alkylthio group, (16) optionally substituted C2-20 alkenylthio group, (17) optionally substituted C2-20 alkynylthio group, (18) mercapto group substituted with an optionally substituted cyclic group, (19) optionally substituted C1-20 alkylsulfinyl group (for example, methylsulfinyl group, ethylsulfinyl group, etc.), (20) optionally substituted C2-20 alkenylsulfinyl group, (21) optionally substituted C2-20 alkynylsulfinyl group, (22) sulfinyl group substituted with an optionally substituted cyclic group (for example, phenylsulfinyl group, etc.), (23) optionally substituted C1-20 alkylsulfonyl group (for example, methylsulfonyl group, ethylsulfonyl group, etc.), (24) optionally substituted C2-20 alkenylsulfonyl group, (25) optionally substituted C2-20 alkynylsulfonyl group, (26) sulfonyl group substituted with an optionally substituted cyclic group (for example, phenylsulfonyl group, etc.), (27) optionally substituted sulfino group, (28) optionally substituted sulfo group, (29) optionally substituted sulfamoyl group (for example, non-substituted sulfamoyl group, N-mono- or di-(optionally substituted C1-20 alkyl) sulfamoyl group (for example, N-mono-C1-6 alkylsulfamoyl group (for example, N-methylsulfamoyl group, N-ethylsulfamoyl group, N-propylsulfamoyl group, N-isopropylsulfamoyl group, N-butylsulfamoyl group, N-isobutylsulfamoyl group, N-(tert-butyl) a sulfamoyl group, N-pentylsulfamoyl group, N-hexylsulfamoyl group, etc.), N,N-di-C1-6 alkylsulfamoyl group (for example, N,N-dimethylsulfamoyl group, N,N-diethylsulfamoyl group, N,N-dipropylsulfamoyl group, N,N-dibutylsulfamoyl group, N,N-dipentylsulfamoyl group, N,N-dihexylsulfamoyl group, N-methyl-N-ethylsulfamoyl group, etc.), etc.), etc.), (30) optionally substituted carbonyl group (for example, C1-6 alkoxycarbonyl group such as methoxycarbonyl group, ethoxycarbonyl group, t-butoxycarbonyl group, etc.; C3-8 cycloalkanoyl group such as cyclopentylcarbonyl group, cyclohexylcarbonyl group, etc.; C6-10 arylcarbonyl group such as benzoyl group, etc.; heterocyclic ring carbonyl group which may have a substituent(s) such as morpholin-4-ylcarbonyl group, piperidin-1-ylcarbonyl group, 1-methylpiperazin-4-ylcarbonyl group, etc.), (31) optionally substituted C1-20 acyl group (for example, formyl group, acetyl group, propanoyl group, pivaloyl group, etc.), (32) optionally substituted carbamoyl group (for example, non-substituted carbamoyl group, N-mono- or di-(optionally substituted C1-20 alkyl)carbamoyl group (for example, N-mono-C1-6 alkylcarbamoyl group (for example, N-methylcarbamoyl group, N-ethylcarbamoyl group, N-propylcarbamoyl group, N-isopropylcarbamoyl group, N-butylcarbamoyl group, N-isobutylcarbamoyl group, N-(tert-butyl)carbamoyl group, N-pentylcarbamoyl group, N-hexylcarbamoyl group, etc.), N-mono-C1-6 alkylcarbamoyl group substituted with a hydroxyl group (for example, N-hydroxymethylcarbamoyl group, N-(2-hydroxyethyl)carbamoyl group, N-(3-hydroxypropyl)carbamoyl group, N-(4-hydroxybutyl)carbamoyl group, etc.), N-mono-C1-6 alkylcarbamoyl group substituted with an amino group or a dimethylamino group (for example, N-aminomethylcarbamoyl group, N-(2-aminoethyl)carbamoyl group, N-(3-aminopropyl)carbamoyl group, N-(4-aminobutyl)carbamoyl group, N-(dimethylamino)methylcarbamoyl group, N-(2-dimethylaminoethyl)carbamoyl group, N-(3-dimethylaminopropyl) carbamoyl group, N-(4-dimethylaminobutyl)carbamoyl group, etc.), N,N-di-C1-6 alkylcarbamoyl group (for example, N,N-dimethylcarbamoyl group, N,N-diethylcarbamoyl group, N,N-dipropylcarbamoyl group, N,N-dibutylcarbamoyl group, N,N-dipentylcarbamoyl group, N,N-dihexylcarbamoyl group, N-methyl-N-ethylcarbamoyl group, etc.), etc.), N-mono- or di-(optionally substituted carbocyclic ring or heterocyclic ring) carbamoyl group (for example, N-mono(an optionally substituted carbocyclic ring) carbamoyl group (for example, N-cyclopropylcarbamoyl group, N-cyclopentylcarbamoyl group, N-cyclohexylcarbamoyl group, N-phenylcarbamoyl group, etc.), etc.), etc.), (33) cyano group, (34) optionally substituted amidino group, (35) nitro group, (36) nitroso group, (37) optionally substituted imino group (for example, non-substituted imino group, imino group substituted with C1-6 alkyl group (for example, methylimino group, ethylimino group, etc.), imino group substituted with a C6-10 aryl group which may have a substituent(s) (for example, phenylimino group, p-fluorophenylimino group, p-chlorophenylimino group, etc.), imino group substituted with a hydroxyl group such as hydroxyimino group, etc.), (38) optionally substituted amino group (for example, mono- or di-C1-6 alkylamino group (for example, methylamino group, ethylamino group, propylamino group, dimethylamino group, diethylamino group, etc.), mono- or di-C6-10 arylamino group (for example, phenylamino group, diphenylamino group, etc.), mono-C1-6 alkyl-mono-C6-10 arylamino group (for example, N-phenyl-N-methylamino group, N-phenyl-N-ethylamino group, etc.), etc.), (39) halogen atom, (40) carboxyl group, (41) phosphono group (—PO(OH)$_2$), (42) dihydroxyboryl group (—B(OH)$_2$), (43) C1-20 alkylcarbonylhydazino group (for example, methylcarbonylhydazino group, ethylcarbonylhydazino group, etc.), and (44) C6-10 arylhydrazone group which may have a substituent(s), such as benzoaldehydehydrazone group, p-methoxybenzoaldehydehydrazone group, etc. . . . These optional substituents may be substituted on the optional substitutable position in optional substitutable number. When the number of substituents is 2, the "optionally substituted sulfamoyl group", "optionally substituted carbamoyl group", "optionally substituted amidino group" and "optionally substituted amino group" exemplified as for (29), (32), (34) and (38) of the "substituents" in the "cyclic group which may have a substituent(s)" represented by ring $B^P$ are combined together with nitrogen atoms to which they are attached to form a 5- to 7-membered monocyclic heterocyclic ring having 1 to 5 nitrogen atom(s), one oxygen atom and/or one sulfur atom, and the heterocyclic ring thus formed may be substituted with a C1-8 alkyl group, hydroxyl group or amino group.

The "cyclic group" in substituents exemplified in (1) to (44) as the substituent(s) of the ring $B^P$ has the same meaning as the "cyclic group" in the ring $B^P$.

The description "optionally substituted" in substituents exemplified in (1) to (44) as the substituent(s) of the ring $B^P$ means to be optionally substituted with a substituent(s). Examples of the "substituent" here include (1) C1-20 alkyl group, (2) C2-20 alkenyl group, (3) C2-20 alkynyl group, (4) C1-20 alkylidene group, (5) cyclic group, (6) C1-20 alkyl group substituted with a cyclic group, (7) oxo group, (8) hydroxyl group, (9) C1-20 alkyloxy group, (10) C2-20 alkenyloxy group, (11) C2-20 alkynyloxy group, (12) hydroxyl group which may be protected by a cyclic group, (13) C1-20 acyloxy group, (14) thioxo group, (15) mercapto group, (16) C1-20 alkylthio group, (17) C2-20 alkenylthio group, (18) C2-20 alkynylthio group, (19) mercapto group substituted with a cyclic group, (20) C1-20 alkylsulfinyl group, (21) C2-20 alkenylsulfinyl group, (22) C2-20 alkynylsulfinyl group, (23) sulfinyl group substituted with a cyclic group, (24) C1-20 alkylsulfonyl group, (25) C2-20 alkenylsulfonyl group, (26) C2-20 alkynylsulfonyl group, (27) sulfonyl group substituted with a cyclic group, (28) C1-20 alkylsulfonyl group substituted with a cyclic group, (29) sulfino group, (30) sulfo group, (31) sulfamoyl group, (32) C1-20 acyl group, (33) C1-20 acyl group substituted with a cyclic group, (34) carbonyl group substituted with a cyclic group, (35) carbamoyl group, (36) cyano group, (37) amidino group, (38) nitro group, (39) nitroso group, (40) imino group, (41) amino group, (42)halogen atom, (43) carboxyl group and the like. These optional substituents may be substituted on the optional substitutable position in optional substitutable number. The "cyclic group" in these substituents has the same meaning as the "cyclic group" in the ring $B^P$.

In the present specification, the "C1-20 alkyl group" means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl groups, and isomer groups thereof.

In the present specification, the "C2-20 alkenyl group" means ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and icosenyl groups, and isomer groups thereof.

In the present specification, the "C2-20 alkynyl group" means ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl and icosynyl groups, and isomer groups thereof.

In the present specification, the "C1-20 alkylidene group" means methylidene, ethylidene, propylidene, butylidene, pentylidene, hexylidene, heptylidene, octylidene, nonylidene, decylidene, undecylidene, dodecylidene, tridecylidene, tetradecylidene, pentadecylidene, hexadecylidene, heptadecylidene, octadecylidene, nonadecylidene and icosylidene groups, and isomer groups thereof.

In the present specification, the "C1-20 alkyloxy group" means methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy and icosyloxy groups, and isomer groups thereof.

In the present specification, the "C2-20 alkenyloxy group" means ethenyloxy, propenyloxy, butenyloxy, pentenyloxy, hexenyloxy, heptenyloxy, octenyloxy, nonenyloxy, decenyloxy, undecenyloxy, dodecenyloxy, tridecenyloxy, tetradecenyloxy, pentadecenyloxy, hexadecenyloxy, heptadecenyloxy, octadecenyloxy, nonadecenyloxy, icosenyloxy group, and isomer groups thereof.

In the present specification, the "C2-20 alkynyloxy group" means ethynyloxy, propynyloxy, butynyloxy, pentynyloxy, hexynyloxy, heptynyloxy, octynyloxy, nonyloxy, decynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy and icosynyloxy groups, and isomer groups thereof.

In the present specification, the "C1-20 alkylthio group" means methylthio, ethylthio, propylthio, butylthio, pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio and icosylthio groups, and isomer groups thereof.

In the present specification, the "C2-20 alkenylthio group" means ethenylthio, propenylthio, butenylthio, pentenylthio, hexenylthio, heptenylthio, octenylthio, nonenylthio, decenylthio, undecenylthio, dodecenylthio, tridecenylthio, tetradecenylthio, pentadecenylthio, hexadecenylthio, heptadecenylthio, octadecenylthio, nonadecenylthio and icosenylthio groups, and isomer groups thereof.

In the present specification, the "C2-20 alkynylthio group" means ethynylthio, propynylthio, butynylthio, pentynylthio, hexynylthio, heptynylthio, octynylthio, nonylthio, decynylthio, undecynylthio, dodecynylthio, tridecynylthio, tetradecynylthio, pentadecynylthio, hexadecynylthio, heptadecynylthio, octadecynylthio, nonadecynylthio and icosynylthio groups, and isomer groups thereof.

In the present specification, the "C1-20 alkylsulfinyl group" means methylsulfinyl, ethylsulfinyl, propylsulfinyl, butylsulfinyl, pentylsulfinyl, hexylsulfinyl, heptylsulfinyl, octylsulfinyl, nonylsulfinyl, decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl and icosylsulfinyl groups, and isomer groups thereof.

In the present specification, the "C2-20 alkenylsulfinyl group" means ethenylsulfinyl, propenylsulfinyl, butenylsulfinyl, pentenylsulfinyl, hexenylsulfinyl, heptenylsulfinyl, octenylsulfinyl, nonenylsulfinyl, decenylsulfinyl, undecenylsulfinyl, dodecenylsulfinyl, tridecenylsulfinyl, tetradecenylsulfinyl, pentadecenylsulfinyl, hexadecenylsulfinyl, heptadecenylsulfinyl, octadecenylsulfinyl, nonadecenylsulfinyl and icosenylsulfinyl groups, and isomer groups thereof.

In the present specification, the "C2-20 alkynylsulfinyl group" means ethynylsulfinyl, propynylsulfinyl, butynylsulfinyl, pentynylsulfinyl, hexynylsulfinyl, heptynylsulfinyl, octynylsulfinyl, nonylsulfinyl, decynylsulfinyl, undecynylsulfinyl, dodecynylsulfinyl, tridecynylsulfinyl, tetradecynylsulfinyl, pentadecynylsulfinyl, hexadecynylsulfinyl, heptadecynylsulfinyl, octadecynylsulfinyl, nonadecynylsulfinyl and icosynylsulfinyl groups, and isomer groups thereof.

In the present specification, the "C1-20 alkylsulfonyl group" means methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl and icosylsulfonyl groups, and isomer groups thereof.

In the present specification, the "C2-20 alkenylsulfonyl group" means ethenylsulfonyl, propenylsulfonyl, butenylsulfonyl, pentenylsulfonyl, hexenylsulfonyl, heptenylsulfonyl, octenylsulfonyl, nonenylsulfonyl, decenylsulfonyl, undecenylsulfonyl, dodecenylsulfonyl, tridecenylsulfonyl, tetradecenylsulfonyl, pentadecenylsulfonyl, hexadecenylsulfonyl, heptadecenylsulfonyl, octadecenylsulfonyl, nonadecenylsulfonyl and icosenylsulfonyl groups, and isomer groups thereof.

In the present specification, the "C2-20 alkynylsulfonyl group" means ethynylsulfonyl, propynylsulfonyl, butynylsulfonyl, pentynylsulfonyl, hexynylsulfonyl, heptynylsulfonyl, octynylsulfonyl, nonylsulfonyl, decynylsulfonyl, undecynylsulfonyl, dodecynylsulfonyl, tridecynylsulfonyl, tetradecynylsulfonyl, pentadecynylsulfonyl, hexadecynylsulfonyl, heptadecynylsulfonyl, octadecynylsulfonyl, nonadecynylsulfonyl and icosynylsulfonyl groups, and isomer groups thereof.

In the present specification, the "C1-20 acyl group" means methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl groups, and isomer groups thereof.

In the present specification, "C1-20 acyloxy group" means methanoyloxy, ethanoyloxy, propanoyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy and icosanoyloxy groups, and isomer groups thereof.

In the present specification, the "halogen atom" means fluorine atom, chlorine atom, bromine atom and iodine atom.

In the present specification, the "optionally substituted nitrogen atom" represented by $A^P$ has the same meaning as the "divalent nitrogen atom which may have a substituent(s)" in the "spacer having a main chain of 1 to 4 atom(s)" represented by $B^1$ and $B^2$ described hereinafter.

In the present specification, the "optionally substituted C1-8 alkylene group" represented by $D^P$ and $E^P$ means those in which optional substituents are combined with optional carbon atoms of a C1-8 alkylene group. The "substituent" includes, for example, substituents exemplified as "substituents" in the "cyclic group which may have a substituent(s)" represented by ring $B^P$.

In the present specification, the "optionally substituted C2-8 alkenylene group" represented by $D^P$ and $E^P$ means those in which optional substituents are combined with optional carbon atoms of a C2-8 alkylene group. The "substituent" includes, for example, substituents exemplified as "substituents" in the "cyclic group which may have a substituent(s)" represented by ring $B^P$.

In the present specification, the "optionally substituted C2-8 alkynylene group" represented by $D^P$ and $E^P$ means those in which optional substituents are combined with optional carbon atoms of a C2-8 alkylene group. The "substituent" includes, for example, substituents exemplified as "substituents" in the "cyclic group which may have a substituent(s)" represented by ring $B^P$.

In the present specification, the "spacer having a main chain of an oxygen atom, a nitrogen atom, a sulfur atom and/or a phosphorus atom" represented by $M^P$ means a spacer having at least one of an oxygen atom, a nitrogen atom, a sulfur atom and/or a phosphorus atom in its main chain, and the kind and number of other constituent atoms are not limited. The spacer having a main chain of an oxygen atom, a nitrogen atom, a sulfur atom and/or a phosphorus atom include, for example, —COO—, —COOCO—, —CONR$^{XP}$—, CONR$^{XP}$CO—, —O—, —OCO—, —OCOO—, —OCONR$^{XP}$—, NR$^{XP}$—, NR$^{XP}$CO—, NR$^{XP}$COO—, NR$^{XP}$CONR$^{YP}$—, —S—, —S(O)—, —SO$_2$—, —SO$_2$NR$^{XP}$—, —NR$^{XP}$SO$_2$—, —OSO$_3$—, and —OP(=O)(R$^{ZP}$)O—[wherein R$^{XP}$ and R$^{YP}$ each independently represents a hydrogen atom or a substituent, and R$^{ZP}$ represents an hydroxyl group which may be protected or "O$^-$"] and the like.

In the present specification, the "substituent" represented by R$^P$, R$^{XP}$ and R$^{YP}$ are not specifically limited as long as it is a substituent. The "substituent" includes, for example, substituents exemplified as "substituents" in the "cyclic group which may have a substituent(s)" represented by ring $B^P$.

In the present specification, the "protective" group in the "hydroxyl group which may be protected" represented by R$^{ZP}$ include, for example, the same substituents as those exemplified as the "substituents" in the "cyclic group which may have a substituent(s)" represented by ring $B^P$.

In the present specification, "O$^-$" represented by R$^{ZP}$ means an oxygen anion. When R$^{ZP}$ represents "O$^-$", a cation part (for example, quaternized nitrogen atom, etc.) necessarily exists in the molecule.

In the present specification, the "C1-8 alkylene group" means methylene, ethylene, trimethylene, tetramethylene, pentamethylene, hexamethylene, heptamethylene and octamethylene groups, and isomer groups thereof.

In the present specification, the "C2-8 alkenylene group" means ethenylene, propenylene, butenylene, butadienylene, pentenylene, pentadienylene, hexenylene, hexadienylene, heptenylene, heptadienylene, octenylene, and octadienylene groups, and isomer groups thereof.

In the present specification, the "C2-8 alkynylene group" means ethynylene, propynylene, butynylene, butadiynylene, pentynylene, pentadiynylene, hexynylene, hexadiynylene, heptynylene, heptadiynylene, octynylene and octadiynylene groups, and isomer groups thereof.

When the acidic group represents a carboxyl group of the first group and is also protected by a group represented by formula (P), the group represented by formula (P) is combined with a carboxyl group as shown in formula:

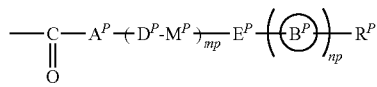

In the present specification, the "group having an acidic group" in the "group having an acidic group which is protected by a protective group" represented by M$^{41}$ and M$^{42}$ has the same meaning as described in the "group having an acidic group".

In the present specification, the "protective group" in the "group having an acidic group which is protected by a protective group" represented by M$^{41}$ and M$^{42}$ has the same meaning as described in the "protective group".

In the present specification, "in a prodrug modification" in the "group having an acidic group in a prodrug modification" means that the structure is chemically modified for the purpose of improving solubility, alimentary canal mucosa permeability, migration in blood, and tissue migration of the compound, thereby improving bioavailability as a drug, or improving properties as problems caused upon oral administration, such as bitterness and irritation of the compound.

In the present specification, the "group having an acidic group in a prodrug modification" may have any structure as long as it is converted into an original "group having an acidic group" by the reaction with an enzyme such as hydrolase or oxidoreductase, or gastric acid in the living body, or under physiological conditions. Specific examples thereof include "groups having an acidic group which is protected by a protective group" represented by M$^{41}$ and M$^{42}$.

In the present specification, the "substituent" in "methylene which may have 1 to 2 substituent(s)" and "ethenylene which may have 1 to 2 substituent(s)" represented by Y$^1$, Y$^2$ and Y$^3$ is not specifically limited. Examples thereof include substituents exemplified as for T.

In the present specification, the "protective group" in the "carboxyl group which may be protected by a protective group", "sulfo group which may be protected by a protective group", and "phosphono group which may be protected by a protective group" represented by Z$^A$ has the same meaning as described the "protective group" of the "group having an acidic group which may be protected by a protective group" represented by M$^{41}$ and M$^{42}$.

In the present specification, the "carboxyl group which may be protected by a protective group" represented by Z$^{1A}$ has the same meaning as described in the "carboxyl group which may be protected by a protective group" represented by Z$^A$.

In the present specification, the "hydrocarbon group which may have a substituent(s)" in the "carboxyl group which may be protected by a hydrocarbon group which may have a substituent(s)" represented by Z$^{1A}$ has the same meaning as described in the "hydrocarbon group which may have a substituent(s)".

In the present specification, the "hydrocarbon group" in the "aminocarbonyl group substituted with a hydrocarbon group" as the "substituent" in the "carboxyl group which may be protected by a hydrocarbon group which may have a substituent(s)" represented by Z$^{1A}$ has the same meaning as described in the "hydrocarbon group" in the "hydrocarbon group which may have a substituent(s)".

In the present specification, examples of the "5- or 6-membered heterocyclic group having, in addition to a carbon atom, 1 to 4 hetero atom(s) selected from an oxygen atom, a sulfur atom and/or a nitrogen atom" in the "5- or 6-membered heterocyclic group which may have a substituent(s) and has, in addition to a carbon atom, 1 to 4 hetero atom(s) selected from an oxygen atom, a sulfur atom and/or a nitrogen atom" as the "substituent" in the "carboxyl group which may be protected by a hydrocarbon group which may have a substituent(s)" represented by Z$^{1A}$ include pyrrole, imidazole, triazole, tetrazole, pyrazole, furan, thiophene, oxazole, isoxazole, thiazole, isothiazole, furazane, oxadiazole, thiadiazole, pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrothiadiazole, tetrahydrothiadiazole (thiadiazolidine), dioxolane, dithiolane, pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydroxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, dithiane ring and the like. The "substituent" includes, for example, substituents exemplified as the "substituents" of definition of "optionally substituted" among the substituents exemplified in (1) to (44) as the substituents of the ring $B^P$. The "substituents" here may be substituted on the substitutable position in substitutable number of 1 to 4. When the number of substituents is two or more, a plurality of substituent may be the same or different.

In the present specification, the "C1-8 alkyl group" in the "carboxyl group optionally protected by a C1-8 alkyl group" represented by $Z^{1A}$ has the same meaning as described in the "C1-8 alkyl group" in the "aliphatic hydrocarbon group".

In the present specification, the "substituents" represented by $R^{1Y}$ and $R^{2Y}$ are not specifically limited and examples thereof include substituents exemplified as for T. These optional substituents may be substituted on the substitutable position in substitutable number of 1 to 2.

In the present specification, the "imidazole, benzimidazole, or pyridine which may have a substituent(s)" represented by rings $A^{1B}$ and $A^{2B}$ means imidazole which may have a substituent(s), benzimidazole which may have a substituent(s), or pyridine which may have a substituent(s).

In the present specification, the "substituent" in the "imidazole, benzimidazole, or pyridine which may have a substituent(s)" represented by rings $A^{1B}$ and $A^{2B}$ has the same meaning as described in the "substituent" in the "nitrogen-containing heterocyclic ring which may have a substituent(s)" in $A^1$ and $A^2$.

In the present specification, "spacer having a main chain of 1 to 4 atom(s)" represented by $B^1$ and $B^2$ mean the space wherein 1 to 4 atom(s) of the main chain are arranged in a line. "Number of atoms of main chain" is counted so that the number of atoms of the main chain is minimized. For example, it is counted that the number of atoms of 1,2-cyclopentylene is 2 and the number of atoms of 1,3-cyclopentylene is 3. Examples of the "spacer having a main chain of 1 to 4 atom(s)" include divalent group composed of 1 to 4 group(s) selected optionally from —O—, —S—, —CO—, —SO—, —SO$_2$—, divalent nitrogen atom which may have a substituent, divalent aliphatic hydrocarbon group having 1 to 4 carbon atom(s) which may have a substituent(s), and divalent 3- to 8-membered monocyclic cyclic group which may have a substituent(s), wherein 1 to 4 atom(s) of the main chain are arranged in a line.

The "divalent nitrogen atom which may have a substituent" represents, in addition to —NH—, those wherein hydrogen atom in the "—NH—" group are optionally substituted with (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, (7) —O-aliphatic hydrocarbon-cyclic group, (8) —SO$_2$-aliphatic hydrocarbon group, (9) —SO$_2$-cyclic group, (10) —SO$_2$-aliphatic hydrocarbon-cyclic group, (11) —CO-aliphatic hydrocarbon, (12) —CO-cyclic group, (13) —CO-aliphatic hydrocarbon-cyclic group, (14) carboxyl group, (15) —COO-aliphatic hydrocarbon, (16) —COO-cyclic group, or (17) —COO-aliphatic hydrocarbon-cyclic group, among the substituents exemplified as for the above-described T.

Furthermore, the "substituent" in the "divalent nitrogen atom which may have a substituent" represents those wherein hydrogen atom in the "—NH—" group are optionally substituted with (a) aliphatic hydrocarbon group substituted with 1 to 5 substituent(s) selected from those exemplified in (5) to (55) of the above T, (b) cyclic group substituted with 1 to 5 substituent(s) selected from those exemplified in (5) to (55) of the above T, (c) cyclic group substituted with "aliphatic hydrocarbon group substituted with 1 to 5 substituent(s) selected from those exemplified in (5) to (55) of the above T", or (d) aliphatic hydrocarbon group substituted with "a cyclic group substituted with 1 to 5 substituent(s) selected from those exemplified in (5) to (55) of the above T". The "aliphatic hydrocarbon group", the "cyclic group" and the "-aliphatic hydrocarbon-" are as defined above.

Examples of the "divalent aliphatic hydrocarbon group having 1 to 4 carbon atom(s)" in the "divalent aliphatic hydrocarbon group having 1 to 4 carbon atom(s) which may have a substituent(s)" include C1-4 alkylene group (for example, —CH$_2$—, —(CH$_2$)$_2$—, —(CH$_2$)$_3$—, —(CH$_2$)$_4$—, etc.), C2-4 alkenylene group (for example, —CH=CH—, —CH$_2$—CH=CH—, —CH=CH—CH$_2$—, —(CH$_2$)$_2$—CH=CH—, —CH=CH—(CH$_2$)$_2$—, —CH$_2$—CH=CH—CH$_2$—, etc.), and C2-4 alkynylene group (for example, —C≡C—, —CH$_2$—C≡C—, —C≡C—CH$_2$—, —(CH$_2$)$_2$—C≡C—, —C≡C—(CH$_2$)$_2$—, —CH$_2$—C≡C—CH$_2$—, etc.). Examples of the "substituent" in the "divalent aliphatic hydrocarbon group having 1 to 4 carbon atom(s) which may have a substituent(s)" include those exemplified as for the above-described T, and these optional substituents may be substituted on the substitutable position and the number of substituents is from 1 to 5, and preferably from 1 to 2.

Examples of the "divalent 3- to 8-membered monocyclic cyclic group" in the "divalent 3- to 8-membered monocyclic cyclic group which may have a substituent(s)" include divalent group which can be obtained by eliminating optional two hydrogen atoms from the "C3-8 monocyclic cyclic group". The two hydrogen atoms may be the ones which bonds the same carbon atom or which bonds different carbon atoms, the latter is preferable. Examples of the "C3-8 monocyclic cyclic group" herein include "C3-8 monocyclic carbocyclic ring" and "3- to 8-membered monocyclic heterocyclic ring". The "C3-8 monocyclic carbocyclic ring" includes C3-8 monocyclic unsaturated carbocyclic ring, and partially or completely saturated one thereof. Examples of the "C3-8 monocyclic unsaturated carbocyclic ring, and partially or completely saturated one thereof" include cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, and benzene rings. Among these, the "C3-8 monocyclic aromatic carbocyclic ring" includes, for example, benzene ring.

Examples of the "3- to 8-membered monocyclic heterocyclic ring" include "3- to 8-membered monocyclic heterocyclic ring having, as a hetero atom, 1 to 4 nitrogen atom(s), 1 to 2 oxygen atom(s) and/or 1 to 2 sulfur atom(s)". The 3- to 8-membered monocyclic heterocyclic ring having, as a hetero atom, 1 to 4 nitrogen atom(s), 1 to 2 oxygen atom(s) and/or 1 to 2 sulfur atom(s)" herein includes 3- to 8-membered monocyclic unsaturated heterocyclic ring having, as a hetero atom, 1 to 4 nitrogen atom(s), 1 to 2 oxygen atom(s) and/or 1 to 2 sulfur atom(s), and partially or completely saturated one thereof. Examples of the "3- to 8-membered monocyclic unsaturated heterocyclic ring having, as a hetero atom, 1 to 4 nitrogen atom(s), 1 to 2 oxygen atom(s) and/or 1 to 2 sulfur atom(s), and partially or completely saturated one thereof" include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolysine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane rings and the like. Among these, examples of the "3- to 8-membered monocyclic aromatic heterocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like.

Examples of the "substituent" in the "divalent 3- to 8-membered monocyclic cyclic group which may have a substituent(s)" include, for example, substituents those exemplified as the above T. These optional substituents may be substituted on the optional substitutable position in optional substitutable number. The number of substituents is preferably from 1 to 8, and more preferably from 1 to 5.

In the present specification, "spacer having a main chain of 1 to 10 atom(s)" represented by E means the space wherein 1 to 10 atom(s) of the main chain are arranged in a line. "Number of atoms of main chain" is counted so that the number of atoms of the main chain is minimized. For example, it is counted that the number of atoms of

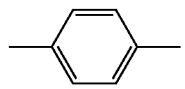

is 4, the number of atoms of

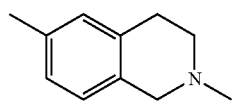

is 6 and the number of atoms of

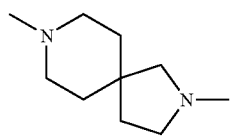

is 6.

Examples of the "spacer having a main chain of 1 to 10 atom(s)" include divalent group composed of 1 to 10 group(s) selected optionally from —O—, —S—, —CO—, —SO—, —SO₂—, divalent nitrogen atom which may have a substituent, divalent aliphatic hydrocarbon group having 1 to 10 carbon atom(s) which may have a substituent(s), and divalent 3- to 15-membered monocyclic cyclic group which may have a substituent(s), wherein 1 to 10 atom(s) of the main chain are arranged in a line. The "divalent nitrogen atom which may have a substituent" is as defined above. Examples of the "divalent aliphatic hydrocarbon group having 1 to 10 carbon atom(s)" in the "divalent aliphatic hydrocarbon group having 1 to 10 carbon atom(s) which may have a substituent(s)" include C1-10 alkylene group (methylene, ethylene, trimethylene, tetramethylene, pentamethylene, hexamethylene, heptamethylene, octamethylene, nonamethylene, decamethylene group, and isomers thereof), C2-10 alkenylene group (ethenylene, propenylene, butenylene, pentenylene, hexenylene, heptenylene, octenylene, nonenylene, decenylene group, and isomers thereof), and C2-10 alkynylene group (ethynylene, propynylene, butynylene, pentynylene, hexynylene, heptynylene, octynylene, nonynylene, decynylene group, and isomers thereof). Examples of the "substituent" in the "divalent aliphatic hydrocarbon group having 1 to 10 carbon atom(s) which may have a substituent(s)" include those exemplified as for T, and these optional substituents may be substituted on the substitutable position and the number of substituents is from 1 to 5, and preferably from 1 to 2.

The "divalent 3- to 15-membered cyclic group" in the "divalent 3- to 15-membered cyclic group which may have a substituent(s)" includes, for example, a divalent group which can be obtained by eliminating optional two hydrogen atoms from the "divalent 3- to 15-membered cyclic group". The "divalent 3- to 15-membered cyclic group" herein includes, for example, a C3-15 monocyclic or fused carbocyclic ring defined above, a C4-15 bridged ring, or a C7-15 spiro-bound carbocyclic ring, a 3- to 15-membered monocyclic or fused heterocyclic ring having, as a hetero atom, 1 to 4 nitrogen atom(s), 1 to 2 oxygen atom(s) and/or 1 to 2 sulfur atom(s), a 4- to 15-membered bridged heterocyclic ring having, as a hetero atom, 1 to 4 nitrogen atom(s), 1 to 2 oxygen atom(s) and/or 1 to 2 sulfur atom(s), and a 7- to 15-membered spiro-bound heterocyclic ring having, as a hetero atom, 1 to 4 nitrogen atom(s), 1 to 2 oxygen atom(s) and/or 1 to 2 sulfur atom(s). Examples of the "substituent" in the "divalent 3- to 15-membered cyclic group which may have a substituent(s)" include those exemplified as for T, and these optional substituents may be substituted on the substitutable position and the number of substituents may be from 1 to 5, and preferably from 1 to 2.

In the present specification, the "divalent 3- to 8-membered monocyclic group which may have a substituent(s)" represented by E has the same meaning as the "divalent 3- to 8-membered monocyclic group which may have a substituent(s)" defined in $B^1$ and $B^2$.

In the present specification, the "divalent 9- to 10-membered fused cyclic ring which may have a substituent(s)" in the "divalent 9- to 10-membered fused cyclic group" represented by E includes, for example, the divalent group which can be obtained by eliminating optional two hydrogen atoms from the "9- to 10-membered fused cyclic ring". The "9- to 10-membered fused cyclic group" herein includes a "9- to 10-membered fused carbocyclic ring" and a "9- to 10-membered fused heterocyclic ring". The "9- to 10-membered fused carbocyclic ring" includes a 9- to 10-membered fused unsaturated carbocyclic ring, and partially or completely saturated one thereof. Examples of the "9- to 10-membered fused unsaturated carbocyclic ring, and partially or completely saturated one thereof" include, for example, azulene, naphthalene, perhydroazulene, indene, perhydroindene, indan, dihydronaphthalene, teterahydronaphthalene, and perhydronaphthalene ring. The "9- to 10-membered fused heterocyclic ring" includes a 9- to 10-membered fused unsaturated heterocyclic ring having, as a hetero atom, 1 to 4 nitrogen atom(s), 1 to 2 oxygen atom(s) and/or 1 to 2 sulfur atom(s), and partially or completely saturated one thereof. Examples of the "9- to 10-membered fused unsaturated heterocyclic ring having, as a hetero atom, 1 to 4 nitrogen atom(s), 1 to 2 oxygen atom(s) and/or 1 to 2 sulfur atom(s), and partially or completely saturated one thereof" include, for example, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole ring.

Examples of the "substituent" in the "divalent 9- to 10-membered fused heterocyclic ring which may have a substituent(s)" represented by E include those exemplified as for T, and these optional substituents may be substituted on the substitutable position and the number of substituents may be from 1 to 5, and preferably from 1 to 2.

In the present specification, the "divalent 3- to 8-membered fused cyclic group which may have a substituent(s)" represented by ring $E^1$ has the same meaning as the "divalent 3- to 8-membered monocyclic cyclic group which may have a substituent(s)" in $B^1$ and $B^2$. The "divalent 9- to 10-membered fused cyclic group which may have a substituent(s)" represented by ring E1 has the same meaning as the "divalent 9- to 10-membered fused cyclic group which may have a substituent(s)" in E.

In the present specification, the "group having a basic group" in the "aliphatic hydrocarbon group which is substituted with a group having a basic group, and also may have a substituent(s)", the "monocyclic or fused cyclic group which is substituted with a group having a basic group, and also may have a substituent(s)", the "spiro-bound cyclic group which may be substituted with a group having a basic group, and also may have a substituent(s)", and the "bridged cyclic group which may be substituted with a group having a basic group, and also may have a substituent(s)" represented by J has the same meaning as the above "group having a basic group" defined in $A^1$ and $A^2$. The "aliphatic hydrocarbon group" in the "aliphatic hydrocarbon group which is substituted with a group having a basic group, and also may have a substituent(s)" herein has the same meaning as the "aliphatic hydrocarbon group". The "monocyclic or fused cyclic group" in the "monocyclic or fused cyclic group which is substituted with a group having a basic group, and also may have a substituent(s)" has the same meaning as the "monocyclic or fused cyclic group" in the above "cyclic group". The "spiro-bound cyclic group" in the "spiro-bound cyclic group which may be substituted with a group having a basic group, and also may have a substituent(s)" has the same meaning as the "spiro-bound cyclic group" in the above "cyclic group". The "bridged cyclic group" of the "bridged cyclic group which may be substituted with a group having a basic group, and also may have a substituent(s)" has the same meaning as the "bridged cyclic group" in the "cyclic group". The "substituent" herein is not specifically limited. Examples thereof include (1) an aliphatic hydrocarbon group which may have a substituent(s), (2) a cyclic group which may have a substituent(s), (3) an aliphatic hydrocarbon group substituted by a cyclic group which may have a substituent(s) and (4) substituent exemplified as the above T other than the above. The "aliphatic hydrocarbon group" and the "cyclic group" herein the "aliphatic hydrocarbon group which may have a substituent(s)", the "cyclic group which may have a substituent(s)" and the "aliphatic hydrocarbon group substituted by a cyclic group which may have a substituent(s)" have the same meaning as described above. The "substituent" in the above (1) to (3) includes those exemplified as for T, and these optional substituents may be substituted on the substitutable position and the number of substituents may be from 1 to 5.

In the present specification, the "spacer having a main chain of 1 to 4 atom(s)" represented by L has the same meaning as the "spacer having a main chain of 1 to 4 atom(s)" defined in $B^1$ and $B^2$.

In the present specification, regarding "-(aliphatic hydrocarbon group having 1 to 3 carbon atom(s) which may have a substituent(s))-(nitrogen atom which may have a substituent(s))-", either of two bonds may be combined with ring $J^1$ or $J^5$, and (nitrogen atom which may have a substituent(s)) is preferably combined with ring $J^1$ or $J^5$.

In the present specification, "-(nitrogen atom which may have a substituent)-" in "-(aliphatic hydrocarbon group having 1 to 3 carbon atom(s) which may have a substituent(s))-(nitrogen atom which may have a substituent)-" represented by $L^4$ has the same meaning as in the "divalent nitrogen atom which may have a substituent". Examples of the "aliphatic hydrocarbon group having 1 to 3 carbon atom(s)" in the "aliphatic hydrocarbon group having 1 to 3 carbon atom(s) which may have a substituent(s)" include C1 to 3 alkylene group (for example, methylene, ethylene, trimethylene, etc.), C2-3 alkenylene group (for example, ethenylene, propenylene, etc.), and C2-3 alkynylene group (for example, ethynylene, propynylene, etc.). Examples of the "substituent" in the "aliphatic hydrocarbon group having 1 to 3 carbon atom(s) which may have a substituent(s)" include those exemplified as for T, and these optional substituents may be substituted on the substitutable position and the number of substituents is from 1 to 3.

In the present specification, the "divalent aliphatic hydrocarbon group having 1 to 4 carbon atom(s) which may have a substituent(s)" represented by $L^A$ is as defined above.

In the present specification,

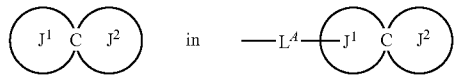

represents that rings $J^1$ and $J^2$ share only one carbon atom to form a spiro-bound cyclic group.

In the present specification, the "C3-10 monocyclic or bicyclic carbocyclic ring" represented by ring $J^1$ includes a C3-10 monocyclic or bicyclic unsaturated carbocyclic ring, and partially or completely saturated one thereof. Examples thereof include, for example, benzene, azulene, naphthalene, cyclopropane, cyclobutane, cyclopentane, cyclohexane, cycloheptane, cyclooctane, cyclononane, cyclodecane, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene and the like.

In the present specification, the "3- to 10-membered monocyclic or bicyclic heterocyclic ring composed of a carbon atom(s), an oxygen atom(s) and/or an optionally oxidized sulfur atom(s)" represented by ring $J^1$ includes a 3- to 10-membered monocyclic or bicyclic unsaturated heterocyclic ring composed of a carbon atom(s), an oxygen atom(s) and/or an optionally oxidized sulfur atom(s), and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dioxolane, dioxane, dithiolane, dithiane, dioxaindane, benzodioxane, chroman, benzodithiolane, benzodithiane and the like.

In the present specification, the "3- to 10-membered monocyclic or bicyclic heterocyclic ring which has at least one nitrogen atom and also may have an oxygen atom(s) or an optionally oxidized sulfur atom(s)" represented by ring $J^1$ includes a 3- to 10-membered monocyclic or bicyclic unsaturated heterocyclic ring which has at least one nitrogen atom and also may have an oxygen atom(s) or an optionally oxidized sulfur atom(s), and partially or completely saturated one thereof. Examples thereof include, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiepine, benzothiazepine, benzothiadiazepine, benzoazepine, benzodiazepine, benzofurazan, benzothiadiazole, benzotriazole and the like.

The "C3-10 monocyclic or bicyclic carbocyclic ring", "3- to 10-membered monocyclic or bicyclic heterocyclic ring composed of a carbon atom(s), an oxygen atom(s) and/or an optionally oxidized sulfur atom(s)", or "3- to 10-membered monocyclic or bicyclic heterocyclic ring which has at least one nitrogen atom and also may have an oxygen atom(s) or an optionally oxidized sulfur atom(s)" in the "C3-10 monocyclic or bicyclic carbocyclic ring, which is substituted with a group having a basic group", "3- to 10-membered monocyclic or bicyclic heterocyclic ring composed of a carbon atom(s), an oxygen atom(s) and/or an optionally oxidized sulfur atom(s), which is substituted with a group having a basic group", or "3- to 10-membered monocyclic or bicyclic heterocyclic ring which has at least one nitrogen atom and also may have an oxygen atom(s) or an optionally oxidized sulfur atom(s), and also which may be substituted with a group having a basic group" represented by ring $J^2$ is as defined above. The "group having a basic group" in ring $J^2$ has the same meaning as the "group having a basic group" defined in $A^1$ and $A^2$.

In the present specification, the "substituent" of the "optionally having a substituent(s)" of rings $J^1$ and $J^2$ is not specifically limited. Examples thereof include those exemplified as for T, and these optional substituents may be substituted on the substitutable position and the number of substituents is preferably from 1 to 8, and more preferably from 1 to 5.

In the present specification,

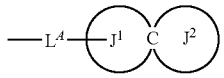

represents

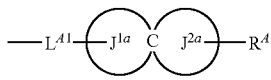

(in the group, $L^{A1}$ has the same meaning as described in -(aliphatic hydrocarbon group having 1 to 3 carbon atom(s) which may have a substituent(s))-(nitrogen atom which may have a substituent(s))- in $L^A$, ring $J^{1a}$ and ring $J^{2a}$ each independently represents (i) a C3-10 monocyclic or bicyclic carbocyclic ring, or (ii) a 3- to 10-membered monocyclic or bicyclic heterocyclic ring composed of a carbon atom(s), an oxygen atom(s) and/or an optionally oxidized sulfur atom(s), $R^A$ represents a group having a basic group, ring $J^{1a}$ and ring $J^{2a}$ may have 1 to 8 substituent(s) on the substitutable position, and when two or more substituents are present, plural substituents may be the same or different, wherein either of "aliphatic hydrocarbon group having 1 to 3 carbon atom(s) which may have a substituent(s)" and "nitrogen atom which may have a substituent(s)" in $L^{A1}$ may be bonded to ring $J^{1a}$, and the "nitrogen atom which may have a substituent(s)" is preferably bonded to ring $J^{1a}$)

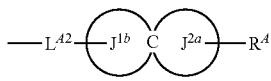

(in the group, $L^{A2}$ has the same meaning as described in a divalent aliphatic hydrocarbon group having 1 to 4 carbon atom(s) which may have a substituent(s) in $L^A$, ring $J^{1b}$ represents a 3- to 10-membered monocyclic or bicyclic heterocyclic ring which has at least one nitrogen atom and also may have an oxygen atom(s) and/or an optionally oxidized sulfur atom(s), ring $J^{1b}$ may have 1 to 8 substituent(s) on the substitutable position, and when two or more substituents are present, plural substituents may be the same or different, and other symbols are as defined above),

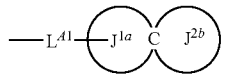

(in the group, ring $J^{2b}$ represents a 3- to 10-membered monocyclic or bicyclic heterocyclic ring which has at least one nitrogen atom and also may have an oxygen atom(s) or an optionally oxidized sulfur atom(s), and which may be substituted with a group having a basic group, ring $J^{2b}$ may have 1 to 8 substituent(s) on the substitutable position, and when two or more substituents are present, plural substituents may be the same or different, and other symbols are as defined above), or

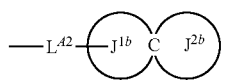

(in the group, all symbols are as defined above).

In the present specification, the "C3-10 monocyclic or bicyclic carbocyclic ring" represented by ring $J^{1a}$ has the same meaning in the "C3-10 monocyclic or bicyclic carbocyclic ring" in ring $J^1$.

In the present specification, the "3- to 10-membered monocyclic or bicyclic heterocyclic ring consisting of a carbon atom, an oxygen atom and/or an optionally oxidized sulfur atom" represented by ring $J^{1a}$ has the same meaning as described in the "3- to 10-membered monocyclic or bicyclic heterocyclic ring consisting of a carbon atom, an oxygen atom and/or an optionally oxidized sulfur atom" in ring $J^1$.

In the present specification, the "3- to 10-membered monocyclic or bicyclic heterocyclic ring which has at least one nitrogen atom and also may have an oxygen atom(s) or an optionally oxidized sulfur atom(s)" represented by ring $J^{1b}$ has the same meaning as described in the "3- to 10-membered monocyclic or bicyclic heterocyclic ring which has at least one nitrogen atom and also may have an oxygen atom(s) or an optionally oxidized sulfur atom(s)" in ring $J^1$.

The "C3-10 monocyclic or bicyclic carbocyclic ring" or "3- to 10-membered monocyclic or bicyclic heterocyclic ring consisting of a carbon atom, an oxygen atom and/or an optionally oxidized sulfur atom" in the "C3-10 monocyclic or bicyclic carbocyclic ring" or "3- to 10-membered monocyclic or bicyclic heterocyclic ring consisting of a carbon atom, an oxygen atom and/or an optionally oxidized sulfur atom" in ring $J^{2a}$ each has the same meaning as described above. The "3- to 10-membered monocyclic or bicyclic heterocyclic ring which has at least one nitrogen atom, and also may have an oxygen atom or an optionally oxidized sulfur atom" in the "3- to 10-membered monocyclic or bicyclic heterocyclic ring which may be substituted with a group having a basic group, and has at least one nitrogen atom and also may have an oxygen atom or an optionally oxidized sulfur atom" represented by ring $J^{2b}$ has the same meaning as described above. The "group having a basic group" in ring $J^{2a}$ has the same meaning as in the "group having a basic group" in $A^1$ and $A^2$.

In the present specification, the "group having a basic group" of $R^A$ has the same meaning as described in the "group having a basic group" in the "spiro-bound cyclic group which may be substituted with a group having a basic group, and also may have a substituent(s)".

In the present specification, the "substituent" of the "may have 1 to 8 substituent(s) on the substitutable position" of ring $J^{1a}$, ring $J^{1b}$, ring $J^{2a}$ and ring $J^{2b}$ is not specifically limited.

Examples thereof include those exemplified as for T, and these optional substituents may be substituted on the substitutable position and the number of substituents is preferably from 1 to 8, and more preferably from 1 to 5.

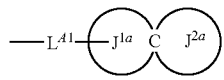

includes, for example,

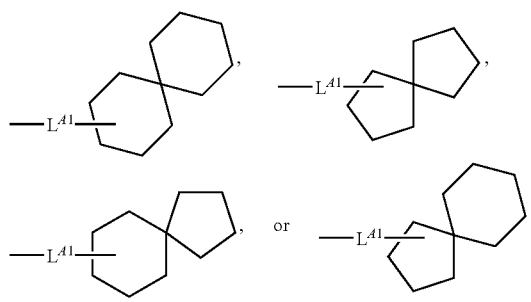

which may have a substituent(s), (wherein the "substituent" include substituents exemplified as for T)

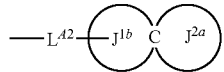

includes, for example,

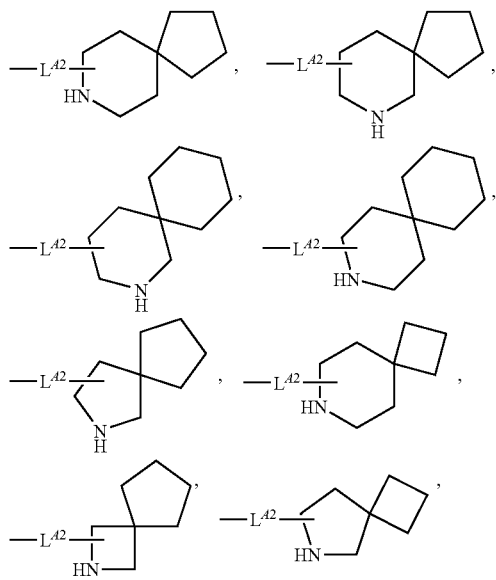

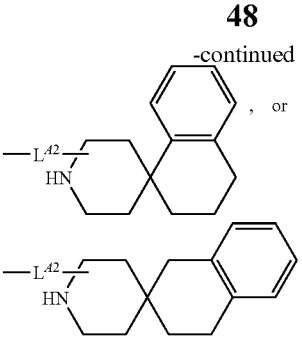

which may have a substituent(s), (wherein $L^{A2}$ may be bonded to a nitrogen atom of —NH—, and examples of the "substituent" include substituents exemplified as for T):

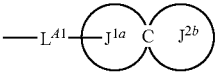

includes, for example,

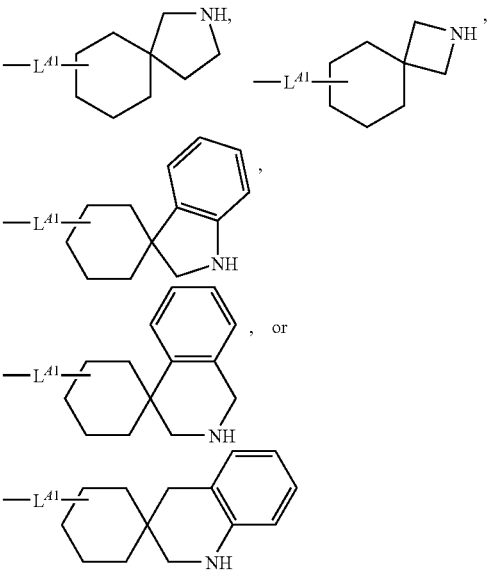

which may have a substituent(s), (wherein a nitrogen atom of —NH— may have a substituent(s), and examples of the "substituent" include substituents exemplified as for T)

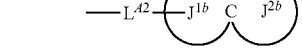

includes, for example,

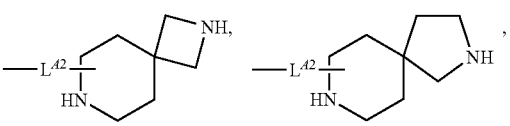

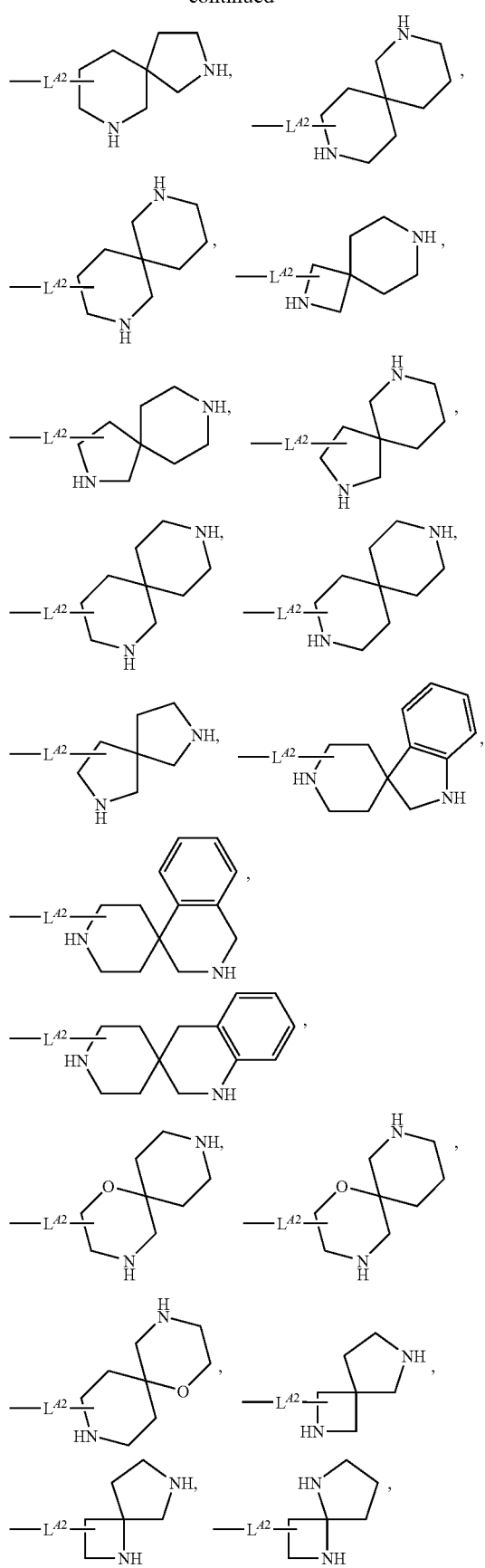
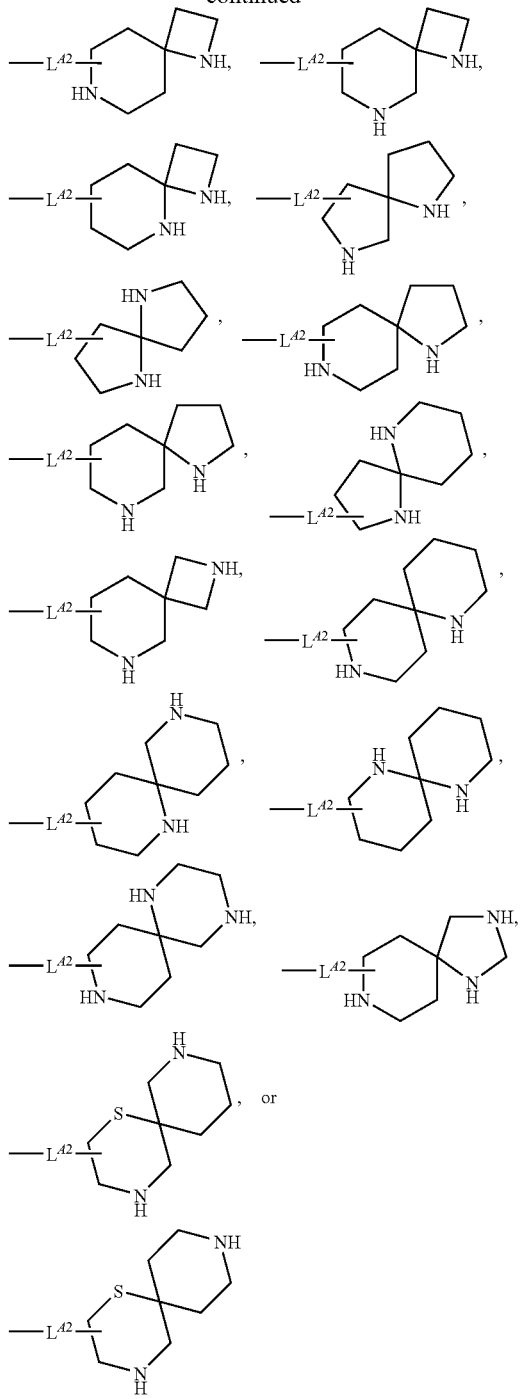

which may have a substituent(s), (wherein $L^{A2}$ may be bonded to a nitrogen atom of —NH—, the nitrogen atom of —NH— may have a substituent(s), and examples of the "substituent" include substituents exemplified as for T) which may have a substituent(s).

In the present specification, the "spiro-bound cyclic group which may be substituted with a group having a basic group, and also may have a substituent(s)" represented by $J^5$ has the same meaning as the "spiro-bound cyclic group which may be substituted with a group having a basic group, and also may have a substituent(s)" in the above-described J.

In the present specification, the "carbon atom which may have a substituent(s)" represented by G represents, in addition to —CH$_2$—, those wherein 1 to 2 hydrogen atoms in the "—CH$_2$-" group are, each independently, optionally substituted with an aliphatic hydrocarbon group, a C1-8 alkylidene group, an aliphatic hydrocarbon group substituted with a cyclic group, a hydroxyl group, an —O-aliphatic hydrocarbon group, a mercapto group, a —S-aliphatic hydrocarbon group, a —S(O)-aliphatic hydrocarbon-cyclic group, a —SO$_2$-aliphatic hydrocarbon group, a —CO-aliphatic hydrocarbon group, a carboxyl group, a —COO-aliphatic hydrocarbon group, a cyano group, a nitro group, a halogen atom, a methyl group which is substituted with 1 to 3 halogen atom(s), a methoxy group which is substituted with 1 to 3 halogen atom(s) or an oxo group. These substituents exemplified herein are the same meaning as the substituents exemplified in the above described T.

In the present specification, the "nitrogen atom which may have a substituent(s)" represented by G represents, in addition to —NH—, those wherein a hydrogen atom in the "—NH—" group are optionally substituted with an aliphatic hydrocarbon group, an aliphatic hydrocarbon group substituted with a cyclic group, an —O-aliphatic hydrocarbon group, a —SO$_2$-aliphatic hydrocarbon group, a —CO-aliphatic hydrocarbon group, a —COO-aliphatic hydrocarbon group, a nitro group, or a methyl group which is substituted with 1 to 3 halogen atom(s). These substituents exemplified herein are the same meaning as the substituents exemplified in the above described T.

In the present specification, "(carbon atom which may have a substituent(s))" of "-(carbon atom which may have a substituent(s))-(nitrogen atom which may have a substituent(s))-" represented by G has the same meaning as the "carbon atom which may have a substituent(s)". The "(nitrogen atom which may have a substituent(s))" of "-(carbon atom which may have a substituent(s))-(nitrogen atom which may have a substituent(s))-" has the same meaning as the "nitrogen atom which may have a substituent(s)".

In the present specification, the "optionally oxidized sulfur atom" means —S—, —SO— and —SO$_2$—.

In the present specification, the "monocyclic cyclic group" in the "monocyclic cyclic group which may have a substituent(s)" represented by ring D has the same meaning as the "3- to 8-membered monocyclic cyclic group" in the "divalent 3- to 8-membered monocyclic cyclic group which may have a substituent(s)" in the above-described B$^1$ and B$^2$.

In the present specification, examples of the "substituent" in the "monocyclic cyclic group which may have a substituent(s)" represented by ring D include those exemplified as for the above-described T, and substituents optional substituents may be substituted on the substitutable position and the number of substituents is from 1 to 5.

In the present specification, the "C3-8 monocyclic carbocyclic ring" in the "C3-8 monocyclic carbocyclic ring which may have a substituent(s)" represented by ring D has the same meaning as the "C3-8 monocyclic carbocyclic ring" in the "divalent 3- to 8-membered monocyclic cyclic group which may have a substituent(s)" in the above-described B$^1$ and B$^2$. Examples of the "substituent" in the "C3-8 monocyclic carbocyclic ring which may have a substituent(s)" include substituents exemplified as for T, and these optional substituents may be substituted on the substitutable position and the number of substituents is from 1 to 5.

In the present specification, the "substituent" represented by R$^1$ is not specifically limited. Examples thereof include (1) aliphatic hydrocarbon group which may have a substituent(s), (2) cyclic group which may have a substituent(s), (3) aliphatic hydrocarbon group substituted with a cyclic group which may have a substituent(s), and (4) substituents exemplified as the above T other than the above (1) to (3). The "aliphatic hydrocarbon group" and "cyclic group" herein the "aliphatic hydrocarbon group which may have a substituent(s)", "cyclic group which may have a substituent(s)" and "aliphatic hydrocarbon group substituted by a cyclic group which may have a substituent(s)" have the same meanings as described above. The "substituent" in (1) to (3) includes substituents exemplified as for T, and these optional substituents may be substituted on the substitutable position and the number of substituents may be from 1 to 5.

In the present specification, the "C4-7 monocyclic carbocyclic ring" represented by R$^1$ include cyclobutane, cyclopentane, cyclohexane, cycloheptane, and benzene and the like.

In the present specification, the "C1-8 alkyl group" represented by R$^1$ has the same meaning as the "C1-8 alkyl group" in the above-described aliphatic hydrocarbon group.

In the present specification, the "halogen atom", "—O-aliphatic hydrocarbon group" and "aliphatic hydrocarbon group" represented by R$^E$ are as defined above.

In the present invention, all isomers are included unless otherwise specified. For example, alkyl group, alkenyl group, alkynyl group, alkylene group, alkenylene group, alkynylene group, alkylidene group and the like include those which are linear and branched. Furthermore, all of isomers (E-, Z-, cis-, and trans-isomers) on the double bond, ring and fused ring, isomers (R-isomer, S-isomer, α,β configuration, enantiomer, and diastereomer) due to the presence of asymmetric carbon, optically active substances with optical rotation (D-, L-, d-, and l-compounds), polar compounds (high polar compound and low polar compound) generated by chromatographic separation, equilibrium compounds, rotational isomers, mixtures in an optional mixing ratio and racemic mixtures are included in the present invention.

In the present invention, as is apparent to those skilled in the art, the symbol  represents that it is bonded to the other side of the page (namely, α configuration), the symbol

 represents that it is bonded to this side of the page (namely, β configuration), the symbol  represents that it is a mixture of the α configuration and the β configuration.

[Salts and Solvates]

Salts of the compound represented by formula (I) include all of nontoxic salts and pharmaceutically acceptable salts. The pharmaceutically acceptable salt is preferably a water soluble salt which shows less toxicity. Examples of the suitable salt of the compound represented by formula (I) include salts of alkali metal (potassium, sodium, lithium, etc.), salts of alkali earth metal (calcium, magnesium, etc.), ammonium salts (tetramethylammonium salt, tetrabutylammonium salt, etc.), salts of organic amine (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)] and the like.

Furthermore, salts include quaternary ammonium salts. The quaternary ammonium salt is obtained by quaternizing a nitrogen atom of the compound represented by formula (I) with a $R^0$ group ($R^0$ group represents a C1-8 alkyl group, or a C1-8 alkyl group substituted with a phenyl group).

Also, salts include N-oxide. The compound of the present invention can be converted into N-oxide by an optional method. N-oxide is obtained by oxidizing a nitrogen atom of the compound represented by formula (I).

Examples of suitable solvate of the compound represented by formula (I) include solvates such as water, alcoholic solvent (for example, methanol, ethanol, etc.) and the like. The solvate is preferably nontoxic and water soluble. The solvate of the compound of the present invention also includes solvates of alkali (earth) metal salts, ammonium salts, salts of organic amine, and acid addition salts of the compound of the present invention.

The compound of the present invention can be converted into the above salts and solvates by a known method.

[Prodrugs]

A prodrug of the compound represented by formula (I), a salt thereof, an N-oxide thereof or a solvate thereof, or a prodrug thereof means a compound which is converted into the compound represented by formula (II):

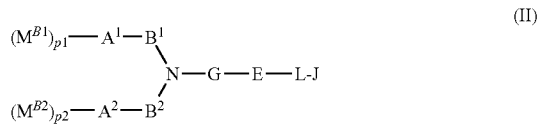

(wherein $M^{B1}$ and $M^{B2}$ each independently represents a group having an acidic group and other symbols are as defined above), in the living body by the reaction with an enzyme, gastric acid or the like. Examples of the prodrug of the compound represented by formula (I) include compound wherein $M^{B1}$ and $M^{B2}$ represent a group having an acidic group which is protected by the protect group in formula (I). In the present invention, Examples of the prodrug of the compound represented by formula (I) include compound wherein an amino group is acylated, alkylated, or phosphorylated (for example, compound wherein an amino group of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.) when the compound represented by formula (I) has an amino group; compound wherein a hydroxyl group is acylated, alkylated, phosphorylated, boricated or the like (for example, compound wherein a hydroxyl group of the compound represented by formula (I) is acetylated, palmitoylated, propanoylated, pivaloylated, succinylated, fumarylated, alanylated, dimethylaminomethylcarbonylated, etc.) when the compound represented by formula (I) has a hydroxyl group; and compound wherein a carboxy group is esterificated, amidated or the like (for example, compound wherein a carboxy group of the compound represented by formula (I) is ethylesterificated, phenylesterificated, carboxymethylesterificated, dimethylaminomethylesterificated, pivaloyloxymethylesterificated, 1-{(ethoxycarbonyl)oxy}ethylesterificated, phthalidylesterificated, (5-methyl-2-oxo-1,3-dioxolen-4-yl)methylesterificated, 1-{[(cyclohexyloxy)carbonyl]oxy}ethylesterificated, methylamidated, etc.) when the compound represented by formula (I) has a carboxy group. These compounds can be prepared by a per se known method. The prodrug of the compound represented by formula (I) may be either of a hydrate and a non-hydrate. These compounds can be prepared by a known method. The prodrug of the compound represented by formula (I) may be either of a hydrate and a non-hydrate. Also, the prodrug of the compound represented by formula (I) may be converted into the compound represented by formula (I) under physiological conditions described in "Development of Drug" published in 1990 by Hirokawa Shoten, Vol. 7, "Molecular Design", pp. 163-198. Furthermore, the compound represented by formula (I) may be labelled with isotope (for example, $^3H$, $^{14}C$, $^{35}S$, $^{125}I$, etc.) and the like.

The compound represented by formula (I) of the present invention, a salt thereof, a solvate thereof, or a prodrug thereof (hereinafter sometimes abbreviated to a compound of the present invention) is a compound which is excellent in solubility and oral absorption and maintains its pharmacological activity for a long period of time, and is also less likely to be inhibited by a drug metabolizing enzyme and has low toxicity. These properties are most important properties required when preparations are developed, and the inventive compound satisfies these conditions and is expected to be useful for developing extremely excellent (see The Merck Manual of Diagnosis and Therapy (17th Ed.), Merck & Co.).

In the formula (I) of the present invention, any of each definition by $M^{A1}$, $M^{A2}$, $A^1$, $B^1$, $B^2$, G, E, L, J, p1 and p2 is preferred. In the following, preferable groups will be listed. The symbols used herein have the same meaning as described above.

In the present specification, the "nitrogen-containing heterocyclic ring" in the "nitrogen-containing heterocyclic ring which may have a substituent(s)" represented by $A^1$ and $A^2$ is preferably, for example, imidazole, benzimidazole, or pyridine. Provided that $A^1$ and $A^2$ may be the same or different. The "substituent" in the "nitrogen-containing heterocyclic ring which may have a substituent(s)" represented by $A^1$ and $A^2$ is preferably, for example, absent, an aliphatic hydrocarbon group, or an aliphatic hydrocarbon group substituted by 1 to 5 substituent(s) selected from (5) to (26), (29) to (32) and (37) to (55) in the above T, more preferably, for example, absent, a C1-4 alkyl group (for example, methyl, ethyl, propyl, isopropyl, butyl, sec-butyl, tert-butyl group, etc.), an oxo group, or an aliphatic hydrocarbon group substituted by a mono- or di-substituted amino group, and still more preferably, for example, absent, a methyl or a dimethylacetamide group. $A^1$ and $A^2$ include preferably, for example, 1H-imidazol-2-yl, 1-methyl-1H-imidazol-2-yl, 2-(1H-imidazol-1-yl)-N,N-dimethyl acetamide, 1-isobutyl-1H-imidazol-2-yl, or 3-methyl-2-pyridinyl, and more preferably 1H-imidazol-2-yl or 1-methyl-1H-imidazol-2-yl.

In the present specification, the "substituent" of the "imidazole which may have a substituent(s), benzimidazole which may have a substituent(s), or pyridine which may have a substituent(s)" represented by rings $A^{1B}$ and $A^{2B}$ is preferably, for example, absent, an aliphatic hydrocarbon group, an oxo group, or an aliphatic hydrocarbon group substituted by a mono- or di-substituted amino group, and more preferably absent, a C1-4 alkyl group, or N,N-dimethylacetamide.

In the present specification, $B^1$ and $B^2$ preferably represent a spacer having one atom in its main chain, and more preferably, —CO—, —SO$_2$—, or a methylene group (—CH$_2$—) which may have a substituent(s). The "substituent" is preferably absent or a methyl group, and more preferably absent. $B^1$ and $B^2$ may be the same or different.

In the present specification, G is preferably, for example, a bond, a carbon atom which may have a substituent(s), an optionally oxidized sulfur atom, or -(carbon atom which may have a substituent(s))-(a nitrogen atom which may have a substituent (s)). The "substituent" is preferably, for example, absent, a methyl group or an oxo group, and more preferably, for example, absent or an oxo group. G is more preferably, for example, a bond, —CO—, —SO$_2$—, —CH$_2$—, or —CONH—, and most preferably —CH$_2$—.

In the present specification, E is preferably, for example, a divalent aliphatic hydrocarbon group having 1 to 4 carbon atom(s) which may have a substituent(s), a divalent 3- to 8-membered monocyclic cyclic group which may have a substituent(s), or a divalent 9- to 10-membered fused cyclic group which may have a substituent(s), and more preferably, a divalent 3- to 8-membered monocyclic cyclic group which may have a substituent(s), or, a divalent 9- to 10-membered fused cyclic group which may have a substituent(s). The "divalent 3- to 8-membered monocyclic cyclic group which may have a substituent(s)" has the same meaning as defined in B$^1$ and B$^2$. The "3- to 8-membered monocyclic cyclic group" is preferably a C5-7 monocyclic carbocyclic ring (those having 5 to 7 carbon atoms are selected from the above 3-8 monocyclic carbocyclic ring are selected) or a 5- to 7-membered monocyclic heterocyclic ring (those having 5 to 7 membered ring are selected from the above 3- to 8-membered monocyclic heterocyclic ring), still more preferably, for example, a cyclopentane, cyclohexane, cycloheptane, cyclohexene, cyclohexadiene, benzene, pyridine, pyrazine, pyrimidine, pyridazine, piperidine, or piperazine ring, and particularly preferably a benzene or cyclohexane ring. The "9- to 10-membered fused cyclic group" in the "divalent 9- to 10-membered fused cyclic group which may have a substituent(s)" is preferably a 9- to 10-membered fused heterocyclic ring, and more preferably, for example, a tetrahydroisoquinoline ring.

The "substituent" in the "divalent 3- to 8-membered monocyclic cyclic group which may have a substituent(s)" and the "divalent 9- to 10-membered fused cyclic group which may have a substituent(s)" is preferably, for example, absent, a halogen atom or an aliphatic hydrocarbon group, and more preferably absent. The "halogen atom" and "aliphatic hydrocarbon group" have the same meanings as described above.

In the present specification, the ring E$^1$ is preferably, for example, a divalent 3- to 8-membered monocyclic cyclic group which may have a substituent (s). The "monocyclic cyclic group" is preferably, for example, a cyclopentane, cyclohexane, benzene, pyrrolidine, or piperidine ring. The "substituent" is preferably absent, an aliphatic hydrocarbon group, or a halogen atom.

In the present specification, L is preferably, for example, a spacer having 1 a main chain of 1 to 2 atom(s) among spacers having a main chain of 1 to 4 atom(s). The "spacer having a main chain of 1 to 2 atom(s)" is preferably a divalent group composed of 1 to 2 groups selected optionally from —O—, —S—, —CO—, —SO—, —SO$_2$—, a divalent nitrogen atom which may have a substituent, and a divalent aliphatic hydrocarbon group having 1 to 2 carbon atom(s) which may have a substituent(s), wherein 1 to 2 atom(s) of the main chain are arranged in a line, more preferably, for example, —CH$_2$—, —O—CH$_2$—, —S—CH$_2$—, —NH—CH$_2$—, —CH$_2$—CH$_2$—, —CH═CH—, —C≡C—, —CH$_2$—O—, —CH$_2$—S—, —CH$_2$—NH—, —CONH—, —SO$_2$—NH—, —NH—CO—, —NH—SO$_2$—, —CO—, —CO—CO—, —CO—CH$_2$—, or —CH$_2$—CO—, particularly preferably —CO—, —CH$_2$—, —CONH—, —CH$_2$—NH—, —O—CH$_2$—, —S—CH$_2$—, —CH$_2$—CH$_2$—, —CO—CO—, —CO—CH$_2$—, or —CH$_2$—CO— (J is bonded to the right side), and most preferably —CO—, —CH$_2$—, —CO—CO—, —CO—CH$_2$—, —CH$_2$—CO—, or —CH$_2$—CH$_2$—. A bond is also preferred. The "substituent" of the "divalent nitrogen atom which may have a substituent(s)" is preferably, absent, or an aliphatic hydrocarbon group, an aliphatic hydrocarbon group substituted with a carboxyl group, an aliphatic hydrocarbon group substituted by a "—COO-aliphatic hydrocarbon group", an aliphatic hydrocarbon group substituted by a hydroxyl group, or a —CO-cyclic group.

In the present specification, J is preferably, "cyclic group which is substituted by a group having a basic group, and also may have a substituent(s)", or "spiro-bound cyclic group which may be substituted with a group having a basic group, and also may have a substituent(s)". The "cyclic group" is preferably a spiro-bound cyclic group. The "spiro-bound cyclic group" of the "spiro-bound cyclic group which is substituted with a group having a basic group, and also may have a substituent(s)" and the "spiro-bound cyclic group" in the "cyclic group" are preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane, spiro[4.4]nonane, spiro[4.5]decane, spiro[5.5]undecane, spiro[3.4]octane, and spiro[3.5]nonane. The "spiro-bound cyclic group" is more preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 1-oxa-4,8-diazaspiro[5.5]undecane, 1-oxa-4,9-diazaspiro[5.5]undecane, 3,4-dihydrospiro[chromene-2,4'-piperidine], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 1,7-diazaspiro[5.5]undecane, 1,4,9-triazaspiro[5.5]undecane, 1,3,8-triazaspiro

[4.5]decane, 1-thia-4,9-diazaspiro[5.5]undecane, or 1-thia-4,8-diazaspiro[5.5]undecane ring. The "spiro-bound cyclic group" is particularly preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane ring.

In the present specification, the "substituent" of "optionally substituted with a substituent(s)" of rings $J^1$, $J^2$ and $J^5$ is preferably, for example, an aliphatic hydrocarbon group, a cyclic group, an aliphatic hydrocarbon group substituted with a cyclic group, and more preferably an aliphatic hydrocarbon group having 1 to 8 carbon atom(s), or a C3-10 monocyclic or bicyclic carbocyclic ring.

In the present specification, the "substituent having a basic group" of the "substituted with a group having a basic group", or the "may be substituted with a group having a basic group" of rings $J^2$ and $J^5$ is preferably, for example, a mono- or di-substituted amino group or a nitrogen-containing heterocyclic ring which may have a substituent(s). The "mono- or di-substituted amino group" is preferably a di-substituted amino group, more preferably, for example, dimethylamino, diethylamino, dipropylamino, dibutylamino, or N-cyclohexyl-N-propylamino, and particularly preferably dipropylamino or N-cyclohexyl-N-propylamino. The "nitrogen-containing heterocyclic ring which may have a substituent(s)" is preferably piperidine, azetidine, morpholine, pyrrolidine or piperazine ring, and more preferably piperidine ring. The substituent of the "mono-substituted amino group" of the "mono- or di-substituted amino group" is preferably a cyclohexane or cycloheptane ring.

In the present specification, the "spiro-bound cyclic group" of the "spiro-bound cyclic group which may be substituted with a group having a basic group, and also may have a substituent(s)" represented by $J^5$ is preferably, for example, 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane or 1-oxa-4,9-diazaspiro[5.5]undecane ring.

In the present specification,

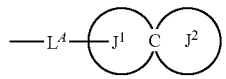

is preferably,

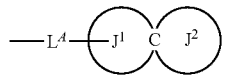

is

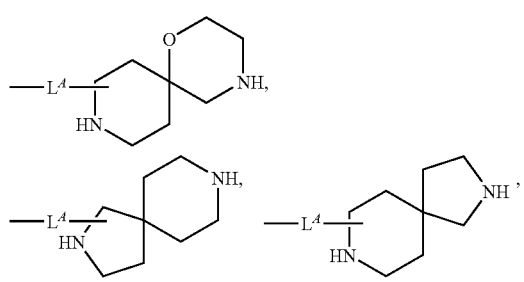

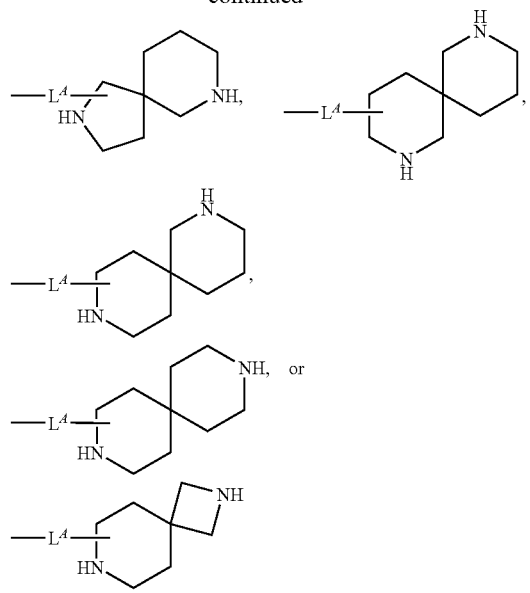

(wherein $L^A$ may be bonded to a nitrogen atom of —NH—, the nitrogen atom of —NH— may have a substituent(s), and the "substituent" includes substituents exemplified as for T) and is more preferably -$L^B$-$J^6$ (in the group, all symbols are defined above).

In the present specification, $J^6$ is preferably, for example,

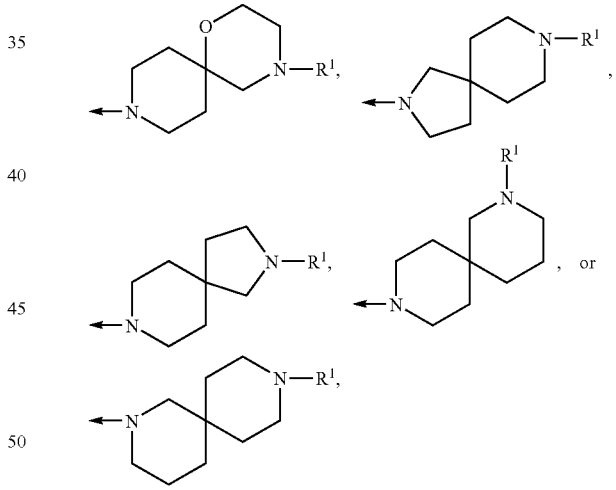

(in the group, the arrow is bonded to $L^{1B}$, and $R^1$ is as defined above).

$L^B$ is preferably, for example, —CO—, —CH$_2$—, or —CH$_2$—CH$_2$—.

$R^1$ is preferably an aliphatic hydrocarbon group which may have a substituent(s), an aliphatic hydrocarbon group substituted with a cyclic group which may have a substituent(s), or a cyclic group which may have a substituent(s). The "aliphatic hydrocarbon group" of the "aliphatic hydrocarbon group which may have a substituent(s)" and the "aliphatic hydrocarbon group substituted with a cyclic group which may have a substituent(s)" represented by $R^1$ is preferably, for example, C1-8 alkyl group, and more preferably, for example, sec-butyl, tert-butyl, or pentyl. The "cyclic group" of the "cyclic group which may have a substituent(s)" represented by $R^1$ is preferably, for example, a C3-15 monocyclic or fused unsaturated carbocyclic ring, or partially or completely saturated carbocyclic ring, more preferably, for example, a C3-8 monocyclic saturated carbocyclic ring, and particularly preferably, for example, a cyclopropane, cyclobutane, cyclopentane, cyclohexane, or cycloheptane ring. The "substituent" of the "aliphatic hydrocarbon group which may have a substituent(s)" is preferably a cyclopentane, cyclohexane, thiophene or benzene ring. The "cyclic group" of the "aliphatic hydrocarbon group substituted with a cyclic group which may have a substituent(s)" is preferably a thiophene ring.

In the present specification, $M^{A1}$ and $M^{A2}$ are preferably $-(Y^1)_q-Z^A$.

In the present specification, the "acidic group" of the "group having an acidic group which may be protected by a protective group" and the "group having an acidic group which is protected by a protective group" represented by $M^{A1}$ and $M^{A2}$ is preferably a carboxyl group, a sulfo group ($-SO_3H$), or a sulfino group ($-SO_2H$), and more preferably a carboxyl group.

In the present specification, the "protective group" of the "group having an acidic group which may be protected by a protective group" represented by $M^{A1}$ and $M^{A2}$ is preferably a hydrocarbon group which may have a substituent(s), more preferably a C1-8 alkyl group, a hydrocarbon group which is substituted with an aminocarbonyl group substituted with C1-8 hydrocarbon, or a hydrocarbon group substituted with a 5- or 6-membered heterocyclic group having, in addition to a carbon atom, 1 to 4 hetero atom(s) selected from an oxygen atom, a sulfur atom and/or a nitrogen atom, and still more preferably a C1-4 alkyl group.

In the present specification, for p1 and p2, it is preferred that p1 is 0 and also p2 is 1, or p1 is 1 and also p2 is 0.

In the present specification, $Y^1$ is preferably a methylene group which may have 1 to 2 substituent(s).

In the present specification, $R^{1Y}$ and $R^{2Y}$ each is preferably a hydrogen atom or an aliphatic hydrocarbon group.

In the present specification, $Y^2$ and $Y^3$ each is preferably a methylene group which may have 1 to 2 substituent(s).

In the present specification, q is preferably an integer of 1 to 4, and more preferably an integer of 1 to 2.

In the present specification, $Z^A$ is preferably a carboxyl group which may be protected by a protective group.

In the present specification, the "protective group" in the "carboxyl group which may be protected by a protective group" represented by $Z^{1A}$ is preferably a hydrocarbon group which may have a substituent (s). The "substituent" in the "hydrocarbon group which may have a substituent(s)" is preferably, (1) absent, (2) aminocarbonyl group substituted with a hydrocarbon group, or (3) 5- or 6-membered heterocyclic group which may have a substituent(s), and also have, in addition to a carbon atom, 1 to 4 hetero atom(s) selected from an oxygen atom, a sulfur atom and/or a nitrogen atom. The "hydrocarbon group" in (2) has the same meaning as described in the "hydrocarbon group" in the "hydrocarbon group which may have a substituent(s)". The "5- or 6-membered heterocyclic group having, in addition to a carbon atom, 1 to 4 hetero atom(s) selected from an oxygen atom, a sulfur atom and/or a nitrogen atom" in (3) is preferably 2- or 3-thienyl, 2- or 3-furyl, 3-, 4- or 5-pyrazolyl, 4-tetrahydropyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, or 2-, 3- or 4-morpholinyl, quinolyl, isoquinolyl, indolyl. The "substituent" is preferably an optionally substituted C1-20 alkyl group.

In the present specification, the "monocyclic cyclic group" in the "monocyclic cyclic group which may have a substituent(s)" represented by ring D is preferably a C3-8 monocyclic carbocyclic ring.

In the present specification, the "C3-8 monocyclic cyclic group" in the "C3-8 monocyclic cyclic group which may have a substituent(s)" represented by ring D is preferably a C3-8 saturated monocyclic group, and the 3-8 saturated monocyclic group is preferably cyclopentane, cyclohexane, or cycloheptane.

In the present specification, $R^E$ is preferably an aliphatic hydrocarbon group.

In the present specification, t is preferably 0 or 1.

In the present invention, a compound of formula (I) including a combination of preferable groups listed above is preferable.

Among the compound represented by formula (I), the preferred compound includes compounds represented by formula (I-1):

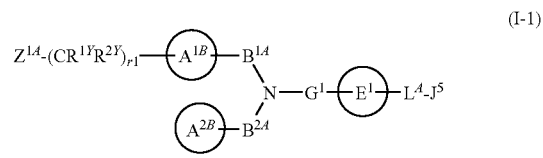

(I-1)

(wherein all symbols are as defined above), or formula (I-2):

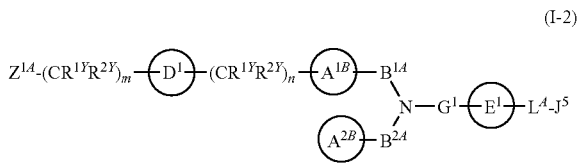

(I-2)

(wherein ring $D^1$ represents a C3-8 monocyclic carbocyclic ring, and other symbols are as defined above), a salt thereof, an N-oxide thereof or a solvate thereof, and a prodrug thereof.

Among the compound represented by formula (I), more preferred compound includes compounds represented by formula (I-1-1):

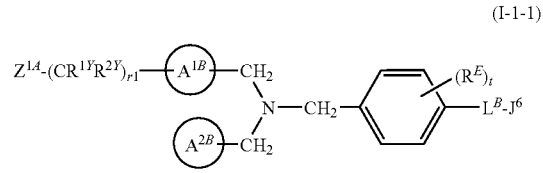

(I-1-1)

(wherein all symbols are as defined above), a salt thereof, an N-oxide thereof or a solvate thereof, and a prodrug thereof.

Examples of preferred compound among the compound represented by formula (I-1-1) include (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetic acid, ethyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate, ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate, 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic acid, ethyl 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoate, 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoic acid, ethyl 4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoate, and 4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoic acid.

Examples of preferred compound of the present invention include compounds described in Examples, salts thereof, N-oxides thereof or solvates thereof, or prodrugs thereof.

Examples of more preferred compound of the present invention include (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetic acid, ethyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate, ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate, 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic acid, 1-{[(cyclohexyloxy)carbonyl]oxy}ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate, ethyl 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoate, 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoic acid, ethyl 4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoate, and 4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoic acid, salts thereof, N-oxides thereof or solvates thereof, and prodrugs thereof.

[Method for Producing Compound of the Present Invention]

The compound of the present invention represented by formula (I) can be prepared by appropriately improving a known method, for example, methods shown below, methods described in Examples, and a method described in Comprehensive Organic Transformations: A Guide to Functional Group Preparations, Second edition (written by Richard C. Larch, John Wiley & Sons Inc, 1999) and using improved methods in combination. In the following production methods, starting compounds may be used in the form of a salt. As the salt, those described as a salt of the above described formula (I) are used.

Among the compound of the present invention represented by formula (I), a compound wherein G represents a carbon atom substituted with an oxo group, namely, a compound represented by formula (I-A):

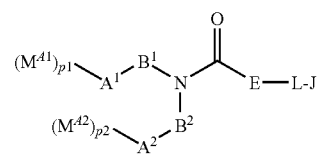

(wherein all symbols are as defined above), can be prepared by subjecting a compound represented by formula (2):

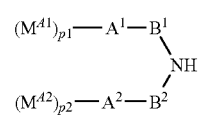

(wherein all symbols are as defined above), and a compound represented by formula (3):

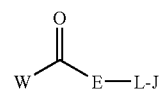

(wherein W represents a hydroxyl group or a chlorine atom and other symbols have the same meaning as described above), to the amidation reaction and optionally subjecting to the deprotection reaction of a protective group and/or the cleavage reaction from a resin.

This amidation reaction is known and examples thereof include:
(1) a method using an acyl halide,
(2) a method using a mixed acid anhydride, and
(3) a method using a condensing agent.

These methods are described in detail below.

(1) The method using an acyl halide is carried out, for example, by reacting carboxylic acid with an acid halogenating agent (oxalyl chloride, thionyl chloride, etc.) in an organic solvent (chloroform, dichloromethane, diethylether, tetrahydrofuran, etc.) or in the absence of the solvent at −20° C. to reflux temperature. Then the obtained acyl halide derivative may be with amine in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) at 0 to 40° C. Alternatively, the obtained acyl halide can be reacted with amine in an organic solvent (dioxane, tetrahydrofuran, etc.) at 0 to 40° C. using an aqueous alkali solution (sodium bicarbonate water or sodium hydroxide solution, etc.).

(2) The method using a mixed acid anhydride is carried out, for example, by reacting carboxylic acid with an acyl halide (pivaloyl chloride, tosyl chloride, mesyl chloride, etc.) or an acid derivative (ethyl chloroformate, butyl chloroformate, etc.) in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) or in the absence of the solvent at 0 to 40° C., and reacting the resulting mixed acid anhydride with amine in an organic solvent (chloroform, dichloromethane, diethylether, tetrahydrofuran, etc.) at 0 to 40° C.

(3) The method using a condensing agent is carried out, for example, by reacting carboxylic acid with amine in an organic solvent (chloroform, dichloromethane, dimethyl formamide, diethylether, tetrahydrofuran, etc.) or in the absence of the solvent at 0 to 40° C. in the presence or absence of a base (pyridine, triethylamine, diisopropylethylamine, N,N-dimethylaniline, N-methylmorpholine, 4-dimethylaminopyridine, etc.), using a condensing agent (1,3-dicyclohexylcarbodiimide (DCC), 1-ethyl-3-[3-(dimethylamino)propyl]carbodiimide (EDC), 1,1'-carbonyldiimidazole (CDI), O-(7-azabenzotriazol-1-yl)N,N,N',N'-tetramethyluronium hexafluorophosphate (HATU), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt)or 1-hydroxy-7-azabenzotriazole (HOAt).

The reactions described in (1), (2) and (3) are preferably carried out under an inert gas (argon, nitrogen, etc.) atmosphere on anhydrous condition.

The deprotection reaction of a protective group can be carried out by a known method, for example, a method described in Protective Groups in Organic Synthesis (written by T. W. Greene, John Wiley & Sons Inc, 1999).

If the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. using an acid (acetic acid, trifluoroacetic acid, hydrochloric acid, etc.).

If necessary, the procedure of converting into the objective salt may be carried out by a known method after this reaction.

A compound wherein G represents —SO$_2$— among the compounds of the present invention represented by formula (I), namely, a compound represented by formula (I-B):

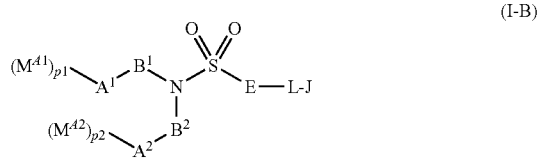

(I-B)

(wherein all symbols are as defined above), can be prepared by subjecting a compound represented by formula (2) and a compound represented by formula (4):

(4)

(wherein X represents a halogen atom and other symbols are as defined above), to the sulfonamidation reaction and optionally subjecting to the deprotection reaction of a protective group and/or the cleavage reaction from a resin.

The sulfonamidation reaction is known and can be carried out by the following method. For example, a sulfonyl halide can be synthesized by reacting a sulfonic acid with an acyl halide (oxalyl chloride, thionyl chloride, phosphorous pentachloride, phosphorus trichloride or phosphorus oxychloride, or a mixture thereof, etc.) in an organic solvent (chloroform, dichloromethane, dichloroethane, diethylether, tetrahydrofuran, methyl t-butyl ether, etc.) or in the absence of the solvent at −20° C. to reflux temperature in the presence or absence of dimethylformamide, or reacting a thiol with a chlorine gas in an aqueous acid solution (for example, hydrochloric acid, sulfuric acid, nitric acid, acetic acid, etc.) at 0° C. to reflux temperature. The sulfonyl halide thus synthesized can be reacted with amine in the presence of a base (diisopropylethylamine, pyridine, triethylamine, N,N-dimethylaniline, 4-dimethylaminopyridine, etc.) in an organic solvent (chloroform, dichloromethane, dichloroethane, diethylether, tetrahydrofuran, etc.) at 0 to 40° C. The deprotection reaction of a protective group or the cleavage reaction from the resin can be carried out by the same method as described above.

Among the compound of the present invention represented by formula (I), a compound wherein G represents -(carbon atom substituted with an oxo group) —NH—, namely, a compound represented by formula (I-N):

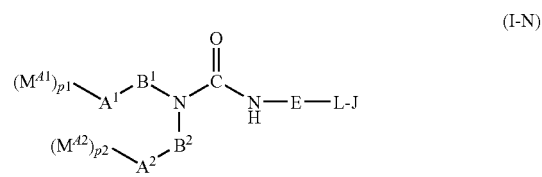

(I-N)

(wherein all symbols are as defined above), can be prepared by subjecting a compound represented by formula (2), a phosgene equivalent (phosgene, diphosgene, triphosgene, carbonyldiimidazole, etc.) and a compound represented by formula (5):

$H_2N$-E-L-J (5)

(wherein all symbols are as defined above), to the urea reaction and optionally subjecting to the deprotection reaction of a protective group and/or the cleavage reaction from a resin.

This urea reaction is known and is conducted, for example, by reacting a compound represented by formula (2) with a phosgene derivative (phosgene, diphosgene, triphosgene, carbonyldiimidazole, etc.) in an organic solvent (dichloromethane, chloroform, diethylether, tetrahydrofuran, etc.) or in the absence of the solvent at −78° C. to 40° C. in the presence of a base (pyridine, triethylamine, N,N-diisopropylethylamine, 4-dimethylaminopyridine, N-methylmorpholine, etc.), and reacting the compound thus obtained with a compound represented by formula (5) in an organic solvent (dichloromethane, chloroform, diethylether, tetrahydrofuran, etc.) or in the absence of a solvent at −78 to 40° C. in the presence of a base (pyridine, triethylamine, N, N-diisopropylethylamine, 4-dimethylaminopyridine, N-methylmorpholine, etc.).

The reaction is preferably carried out under an inert gas (argon, nitrogen, etc.) atmosphere under anhydrous conditions.

The deprotection reaction of a protective group or the cleavage reaction from a resin can be carried out the same manner as described above.

If necessary, the procedure of converting into the objective salt may be carried out by a known method after this reaction.

Among the compound of the present invention represented by formula (I), a compound wherein L represents an amide bond, namely, a compound represented by formula (I-C-1):

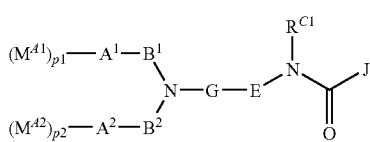
(I-C-1)

(wherein $R^{C1}$ represents a hydrogen atom, or a substituent or a hydrogen atom in the "divalent nitrogen atom which may have a substituent(s)" defined in L, and other symbols are as defined above),
or formula (I-C-2):

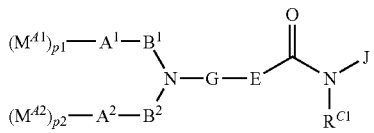
(I-C-2)

(wherein all symbols are as defined above), can be prepared by subjecting a compound represented by formula (6):

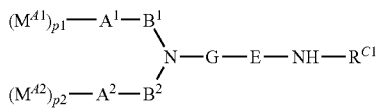
(6)

(wherein all symbols are as defined above), and a compound represented by formula (7):

(7)

(wherein all symbols are as defined above), to the amidation reaction and optionally subjecting to the deprotection reaction of a protective group and/or the cleavage reaction from a resin, or subjecting a compound represented by formula (8):

(8)

(wherein all symbols are as defined above), and a compound represented by formula (9):

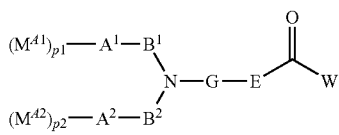
(9)

(wherein all symbols are as defined above), to the amidation reaction and optionally subjecting to the deprotection reaction of a protective group and/or the cleavage reaction from a resin.

The amidation reaction, the deprotection reaction of a protective group or the cleavage reaction from a resin can be carried out the same manner as described above.

Among the compound of the present invention represented by formula (I), a compound wherein L represents a sulfonamide bond, namely, a compound represented by formula (I-D-1):

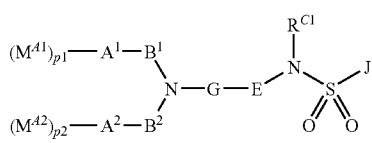
(I-D-1)

(wherein all symbols are as defined above), or formula (I-D-2):

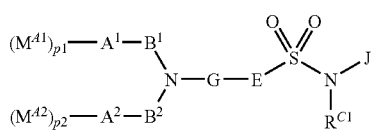
(I-D-2)

(wherein all symbols are as defined above), can be prepared by subjecting a compound represented by formula (6) and a compound represented by formula (10):

(10)

(wherein all symbols are as defined above), to the sulfonamidation reaction and optionally subjecting to the deprotection reaction of a protective group and/or the cleavage reaction from a resin, or subjecting a compound represented by formula (8) and a compound represented by formula (11):

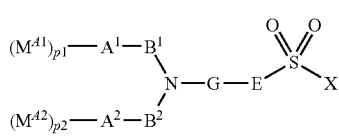
(11)

(wherein all symbols are as defined above), to the sulfonamidation reaction and optionally subjecting to the deprotection reaction of a protective group and/or the cleavage reaction from a resin.

The sulfonamidation reaction, the deprotection reaction of a protective group or the cleavage reaction from a resin can be carried out the same manner as described above.

Among the compound of the present invention represented by formula (I), a compound wherein a divalent group adjacent to a nitrogen atom in $B^1$ is —CO—, namely, a compound represented by formula (I-K):

$$(M^{41})_{p1} - A^1 - B^{1K} - C(=O) - N(G-E-L-J) - A^2 - B^2 - (M^{42})_{p2} \quad \text{(I-K)}$$

(wherein $B^{1K}$ represents a bond or a spacer having 1 to 3 atoms(s) in its main chain and other symbols have the same meaning as described above) can be prepared by subjecting a compound represented by formula (12):

$$(M^{42})_{p2}\text{-}A^2\text{-}B^2\text{—NH-G-E-L-J} \quad (12)$$

(wherein all symbols are as defined above), and a compound represented by formula (13):

$$(M^{41})_{p1} - A^1 - B^{1K} - C(=O) - W \quad (13)$$

(wherein all symbols are as defined above), to the amidation reaction and optionally subjecting to the deprotection reaction of a protective group and/or the cleavage reaction from a resin.

The amidation reaction, the deprotection reaction of a protective group or the cleavage reaction from a resin can be carried out the same manner as described above.

Among the compound of the present invention represented by formula (I), a compound wherein a divalent group adjacent to a nitrogen atom in $B^1$ is —$SO_2$—, namely, a compound represented by formula (I-L):

$$(M^{41})_{p1} - A^1 - B^{1L} - S(=O)_2 - N(G-E-L-J) - A^2 - B^2 - (M^{42})_{p2} \quad \text{(I-L)}$$

(wherein $B^{1L}$ represents a bond or a spacer having 1 to 3 atom(s) in its main chain and other symbols have the same meaning as described above), can be prepared by subjecting a compound represented by formula (12) and a compound represented by formula (14):

$$(M^{41})_{p1} - A^1 - B^{1L} - S(=O)_2 - X \quad (14)$$

(wherein all symbols are as defined above), to the sulfonamidation reaction and optionally subjecting to the deprotection reaction of a protective group and/or the cleavage reaction from a resin.

The sulfonamidation reaction, the deprotection reaction of a protective group or the cleavage reaction from a resin can be carried out the same manner as described above.

Among the compound represented by formula (I), a compound wherein G represents a carbon atom which may have one substituent and a divalent group adjacent to a nitrogen atom in $B^1$ and $B^2$ is —$CH_2$—, namely, a compound represented by formula (I-M):

$$(M^{41})_{p1} - A^1 - B^{1K} - CH_2 - N(H)(-C(R^{M1})(H)-E-L-J) - CH_2 - B^{2K} - A^2 - (M^{42})_{p2} \quad \text{(I-M)}$$

(wherein $B^{2K}$ represents a bond or a spacer having 1 to 3 atoms(s) in its main chain, and $R^{M1}$ represents a hydrogen atom, or a substituent in the "carbon atom which may have a substituent(s)" defined in G and other symbols have the same meaning as described above), can be prepared by subjecting a compound represented by formula (15):

$$(M^{41})_{p1} - A^1 - B^{1K} - CH_2 - NH - CH_2 - B^{2K} - A^2 - (M^{42})_{p2} \quad (15)$$

(wherein all symbols are as defined above), and a compound represented by formula (16):

$$R^{M1} - C(=O) - E - L - J \quad (16)$$

(wherein all symbols are as defined above), to the reductive amination reaction and optionally subjecting to the deprotection reaction of a protective group and/or the cleavage reaction from a resin.

The reductive amination reaction is known and can be carried out in an organic solvent (dichloroethane, dichloromethane, dimethylformamide, acetic acid, a mixture thereof, etc.) at 0 to 40° C. in the presence of a reducing agent (sodium triacetoxyborohydride, sodium cyanoborohydride, sodium borohydride, etc.). The deprotection reaction of a protective group or the cleavage reaction from the resin can be carried out by the same method as described above.

A compound represented by formula (I-M) can be prepared by subjecting a compound represented by formula (17):

$$H_2N - C(R^{M1})(H) - E - L - J \quad (17)$$

(wherein all symbols are as defined above), and a compound represented by formula (18):

$$(M^{41})_{p1}\text{-}A^1\text{-}B^{1K}\text{—CHO} \quad (18)$$

(wherein all symbols are as defined above), to the reductive amination reaction, and subjecting the compound thus obtained and a compound represented by formula (19):

$$[(M^{42})_{p2}\text{-}A^2\text{-}B^{2K}\text{—CHO}] \quad (19)$$

(wherein all symbols are as defined above), to the reductive amination reaction and optionally subjecting to the deprotection reaction of a protective group and/or the cleavage reaction from a resin.

The reductive amination reaction, the deprotection reaction of a protective group or the cleavage reaction from a resin can be carried out the same manner as described above.

A compound of formula (I-M) wherein a $(M^{A1})_{p1}$-$A^1$-$B^{1K}$—$CH_2$— group and a $(M^{A2})_{p2}$-$A^2$-$B^{2K}$—$CH_2$— group represent the same substituent can be prepared by subjecting a compound represented by formula (17) and 2 or more equivalents of a compound represented by formula (18) or formula (19) to the reductive amination reaction and optionally subjecting to the deprotection reaction of a protective group and/or the cleavage reaction from a resin.

The reductive amination reaction, the deprotection reaction of a protective group or the cleavage reaction from a resin can be carried out the same manner as described above.

Among the compound of the present invention represented by formula (I), a compound wherein $A^1$ and $A^2$ represent an imidazol-2-yl group and a divalent group adjacent to a nitrogen atom in $B^1$ and $B^2$ is —$CH_2$—, p1 is 1, p2 is 0, and $M^{A1}$ is a group substituted on the 1-position of imidazole, namely, a compound represented by formula (I-Q):

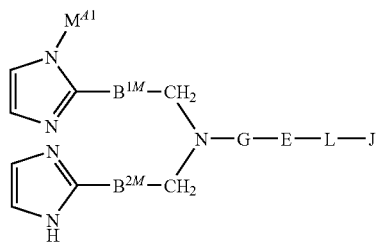

(wherein $B^{1M}$ and $B^{2M}$ represent a bond or a spacer having 1 to 3 atom(s) in its main chain, and other symbols have the same meaning as described above), can be prepared by subjecting a compound represented by formula (20):

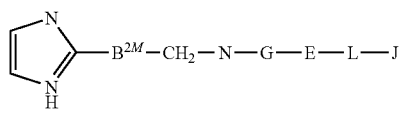

(wherein all symbols are as defined above), and a compound represented by formula (21):

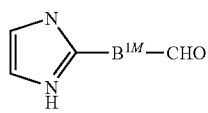

(wherein all symbols have the same meaning as described above), to the reductive amination reaction and optionally subjecting to the deprotection reaction of a protective group and/or the cleavage reaction from a resin.

The reductive amination reaction, the deprotection reaction of a protective group or the cleavage reaction from a resin can be carried out the same manner as described above.

Among the compound represented by formula (I) of the present invention, a compound wherein $M^{A1}$ is an acidic group which is protected by a protective group and the acidic group is —$(CR^{1Y}R^{Y2})_{r1}$—COOH, and p1 represents 1, namely, a compound represented by formula (I-R):

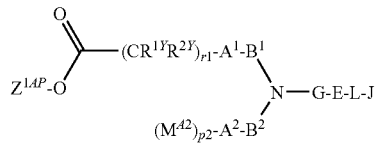

(wherein $Z^{1AP}$ represents a protective group in $M^{A1}$, and other symbols have the same meaning as described above) can be prepared by subjecting a compound represented by formula (22):

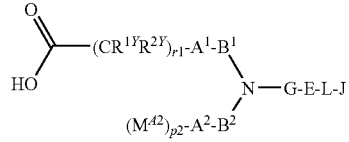

(wherein all symbols are as defined above), and a compound represented by formula (23):

$$Z^{1AP}—Cl \qquad (23)$$

(wherein all symbols are as defined above), to the alkylation reaction.

This alkylation reaction is known and is carried out in an organic solvent (for example, dimethylformamide, dimethyl sulfoxide, etc.) in the presence or absence of an alkali (potassium carbonate, sodium carbonate, triethylamine, etc.) and sodium iodide or potassium iodide at a temperature of about 0 to 150° C.

This reaction is preferably carried out under an inert gas (argon, nitrogen, etc.) under anhydrous conditions.

The compounds represented by formulas (2) to (21) and (23) used as other starting materials or reagents can be easily prepared by using per se known methods or known methods, for example, methods described in Comprehensive Organic Transformations: A Guide to Functional Group Preparations, Second edition (written by Richard C. Larock, John Wiley & Sons Inc, 1999) in combination.

In the respective reactions in the present specification, as is apparent to those skilled in the art, the reaction with heating can be carried out using a water bath, an oil bath, a sand bath, or microwave.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or column chromatography or washing, or recrystallization. The purification may be carried out for every reaction, or may be carried out after the completion of some reactions.

In the reaction using a polystyrene resin in the present specification, the reaction product can be purified by conventional purification methods, for example, washing plural times with a solvent (N,N-dimethylformamide, dichloromethane, methanol, tetrahydrofuran, toluene, acetic acid/toluene, etc.)

[Toxicity]

The compound of the present invention has very low toxicity and is considered to be safe enough for pharmaceutical use.

[Application to Pharmaceuticals]

The compound of the present invention has CXCR4 antagonistic activity in an animal including human, particularly human, and is therefore effective, for example, for a preventive and/or therapeutic agent for inflammatory and immune diseases, allergic diseases, infections, particularly HIV infection, and diseases associated with the infection, psychoneurotic diseases, cerebral diseases, cardiovascular diseases, metabolic diseases, and cancerous diseases. Also, the compound is useful as an agent for regeneration therapy for the purpose of in vitro or in vivo amplification of stem cells for gene therapy as well as peripheral blood stem cells mobilization and tissue repair. The compound is particularly useful as an agent for transplantation medical treatment used in organ transplantation including bone marrow transplantation, peripheral blood stem cell transplantation and tissue repair among in the regeneration therapy. Furthermore, the compound is useful as an antiangiogenic agent which is effective for prevention and/or treatment of diseases associated with neoangiogenesis, such as retinopathy (diabetic retinopathy, aged macular degeneration, glaucoma, etc.) and cancer proliferation.

Examples of the inflammatory and immune disease include rheumatoid arthritis, arthritis, retinopathy, systemic erythematosus, gout, rejection of transplanted organ, graft-versus-host disease (GVHD), nephritis, psoriasis, rhinitis, conjunctivitis, multiple sclerosis, ulcerative colitis, Crohn's disease, shock associated with bacterial infection, pulmonary fibrosis, systemic inflammatory response syndrome (SIRS), acute lung injury, diabetes and the like.

Examples of the allergic disease include asthma, atopic dermatitis, rhinitis, conjunctivitis and the like.

Examples of infections include caused by *streptococcus* (Group A β-hemolytic *streptococcus*, *Streptococcus pneumoniae*, etc.), *staphylococcus aureus* (MSSA, MRSA), *Staphylococcus epidermidis*, *enterococcus*, *Listeria*, *meningococcus*, *gonococcus*, *E. coli* bacteria (0157:H7, etc.), *klebsiella* (*Klebsiella pneumoniae*), *Proteus*, *tussis convulsiva*, *Pseudomonas aeruginosa*, *Serratia marcescens*, *Shiorobactar*, *Ashinetobactar*, *Enterobactar*, *mycoplasma*, *chlamydia*, and *Crostorigeum*, cholera, diphtheria, dysentery, scarlet fever, anthrax, trachoma, syphilis, tetanus, Hansen's disease, *legionella*, Reptospira, Lyme disease, tularaemia, Q fever, meningitis, encephalitis, rhinitis, sinusitis, pharyngitis, laryngitis, orbital cellulitis, thyroiditis, Lemierre syndrome, pneumonia, bronchitis, tuberculosis, infectious endocarditis, pericarditis, myocarditis, infectious aortitis, septicemia, cholecystitis, cholangitis, hepatitis, liver abscess, acute pancreatitis, splenic abscess, enteritis, iliopsoas abscess, pyelonephritis, cystitis, prostatitis, colpitis, Pelvic inflammatory disease, cellulitis, panniculitis, gas gangrene, furuncle, carbuncle, contagious impetigo, staphylococcal scalded skin syndrome, herpes zoster, varicella, measles, rubella, impetigo, scabies, infectious arthritis, osteomyelitis, fasciitis, myositis, and lymphadenitis.

Examples of the disease associated with HIV infection, particularly HIV infection, include acquired immunodeficiency syndrome (AIDS), candidiasis, *Pneumocystis carinii* pneumonia, Cytomegalovirus retinitis, Kaposi's sarcoma, malignant lymphoma, AIDS encephalopathy, and bacterial sepsis.

Examples of the psychoneurotic disease and cerebral disease include dementia including Alzheimer's disease, Parkinson's disease, stroke, cerebral infarction, cerebral hemorrhage, epilepsia, schizophrenia, peripheral nerve disorder and the like.

Examples of the cardiovascular disease include arteriosclerosis, ischemia reperfusion, hypertension, myocardial infarction, stenocardia, heart failure, chronic arterial occlusive disease and the like.

Examples of the metabolic diseases include diabetes, osteoporosis, enlarged prostate, frequent micturition and the like.

Macular degeneration is a disease wherein progressive disorder arises in macula lutea that is present in the center of retina and controls visual acuity, and age-related one is referred to as age-related macular degeneration. Macular degeneration includes atrophy type (dry type) macular degeneration wherein macula lutea tissue causes atrophy and exudation type (wet type) macular degeneration wherein new blood vessel are formed in the chorioidea of the macula lutea site.

Examples of the cancerous disease include malignant tumor such as breast cancer, brain cancer or malignant lymphoma, cancer metastasis, myelosuppression or thrombocytopenia after radiation therapy/chemotherapy and the like.

The compound of the present invention is effective for prevention and/or treatment of cancerous diseases or infections in animals including human, particulary human, and preferably cancerous diseases.

The fact that the compound of the present invention is useful as pharmaceuticals can be evaluated by methods described in various tests and biological examples described hereinafter, and methods which can be carried out by appropriately improving the above methods. The fact that the compound of the present invention is kinetically excellent in length of half-life in blood, stability in gastrointestinal tract, oral absorption and bioavailability can be easily evaluated by a known method, for example, a method described in "Drug Bioavailability (Science of Evaluation and Improvement)", Gendai Iryosha, published on Jul. 6, 1998.

(1) Evaluation Experiment of Inhibitory Activity of Compound of the Present Invention Against Drug-Metabolizing Enzyme (i) Inhibitory Activity Against Hman CYP2A9

An inhibitory activity against CYP2C9 of the compound of the present invention can be evaluated by improving accuracy and/or sensitivity of the measurement in accordance with the method of Sato et al. (Yakubutudotai, Xenobio. Metabol. and Dispos., 16(2), pp. 115-126 (2001)).

(ii) Inhibitory Activity Against Human CYP3A4

Inhibitory activity against CYP3A4 of the compound of the present invention can be evaluated by an improved method described in Drug Metabolism and Disposition, Vol. 28 (12), 1440-1448 (2000).

(2) Evaluation Experiment of Toxicity of Compound of Present Invention (i) Single Acute Toxicity Test in Rat The test compound is administered to six-week Crj:CD (SD) rat by single intravenous dose or single oral administration. Toxicity can be evaluated by contrast with value at no addition of the test compound. Basic evaluation of toxicity can be done by, for example, observation of performance status or locomotor activity, etc.

(ii) Evaluation of Activity of Compound of Present Invention Against hERG $I_{Kr}$ Current According to the report by Zou et al. (Biophys. J., Vol. 74, 230-241 (1998)), using HEK293 cell overexpressed of human ether-a-go-go-related gene (hERG), max tale current of hERG $I_{Kr}$ current induced by depolarization pulse followed by repolarization pulse is measured by patch-clamp recording. Rate of change (inhibition rate) is calculated by comparison max tale current between before addition of the test compound and 10 minutes after. The influence of the test compound against hERG $I_{Kr}$ current can be evaluated by the inhibition rate.

(iii) Evaluation of Action of Compound of Present Invention Against Phospholipidosis It is possible to easily evaluate in accordance with the report by Kasahara et al. (Toxicol. Sci., Vol. 90, pp. 1330-141 (2006)) and the report by Narita at al. (document "in vitro Phospholipidosis Detection System using Fluorescent-Labeled Phospholipids Analogue" distributed in presentation of results of research of Human Science Synthetic Research Promotion Business focusing on Drug Innovation in fisical year 2003).

The measuring methods (1) to (2) are not limited to the above methods and conventional methods can be utilized based on the basic technology. The measuring methods of the present invention can be modified to improve accuracy and/or sensitivity of the measurement for evaluating the compound of the present invention.

The compound of the present invention may be administered as a concomitant drug by using in combination with other drugs for the purpose of:
1) complementation and/or enhancement of the preventive and/or therapeutic effects of the compound,
2) improvement of pharmacokinetics and absorption of the compound and reduction of the dosage, and/or
3) reduction of side effects of the compound.

Also, the compound of the present invention may be administered as a concomitant drug by using in combination with other drugs the purpose of (1) complementation and/or enhancement of preventive and/or therapeutic effects, (2) improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separately. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not specifically limited, and may be any disease which complements and/or enhances the preventive and/or therapeutic effects of the compound of the present invention.

A mass ratio of the compound of the present invention drug to other drugs is not specifically limited.

A combination of any two or more kinds other drugs may be administered.

The other drugs, which complements and/or enhances the preventive and/or therapeutic effects of the compound of the present invention, includes not only those which have ever been found based on the above mechanism, but also those which may be found in future.

Examples of the preventive and/or therapeutic agents for HIV infection and acquired immunodeficiency syndrome, which is used in combination of the compound of the present invention, include reverse transcriptase inhibitors, protease inhibitors, chemokine (for example, CCR2, CCR3, CCR4, CCR5, CXCR4, etc.) antagonists, CD4 antagonists, antibody against surface antigen of HIV (for example, HIV-1, HIV-2, etc.), vaccine of HIV (for example, HIV-1, HIV-2, etc.), short-interfering RNAs targeting a HIV-related factor and the like.

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), didanosine (trade name: videx), adefovir, dipivoxil, emtricitabine (trade name: coviracil), tenofovir (trade name: viread), Combivir, Trizivir, truvada, epzicom, and the like, (2) non-nucleoside reverse transcriptase inhibitors such as nevirapine (trade name: viramune), delavirdine (trade name: Rescriptor), efavirenz (trade name: Sustiva, Stocrin), capravirine (AG1549), and the like.

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), atazanavir (trade name: Reyataz), fosamprenavir (trade name: lexiva), tipranavir and the like.

Examples of the chemokine antagonists include endogenous ligands of a chemokine receptor, or derivatives and nonpeptidic low molecular compounds thereof, an antibody against a chemokine receptor and the like.

Examples of the endogenous ligands of the chemokine receptor include MIP-1α, MIP-1β, RANTES, SDF-1α, SDF-1β, MCP-1, MCP-2, MCP-4, eotaxin, MDC and the like.

Examples of the derivative of the endogenous ligands include AOP-RANTES, Met-SDF-1α, Met-SDF-1β and the like.

Examples of the antibody of the chemokine receptor include Pro-140 and the like.

Examples of the CCR2 antagonists include compounds described in WO99/07351, WO99/40913, WO00/46195, WO00/46196, WO00/46197, WO00/46198, WO00/46199, WO00/69432, WO00/69815, and Bioorg. Med. Chem. Lett., 10, 1803 (2000), and the like.

Examples of the CCR3 antagonists include compounds described in DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327, and WO01/09088, and the like.

Examples of the CCR4 antagonists include compounds described in WO02/030357 and WO02/030358, and the like.

Examples of the CCR5 antagonists include compounds described in WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000-309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514 and Bioorg. Med. Chem. Lett., 10, 1803 (2000), TAK-779, SCH-351125 (SCH-C), SCH-417690 (SCH-D), UK-427857, GW 873140A (ONO-4128), TAK-220, TAK-652, and the like.

Examples of the CD4 antagonist include curdlansulfuric acid, TNX-355, BT-061, CD4 antagonist 802-2, 4162W94, PP-0102, anti-CD4 antibody, AD-519, TRX-1, and CD4-IgG, and the like.

Examples of the CXCR4 antagonist include MD-3100, AMD-070, T-22, KRH-1120, KRH-1636, KRH-2731, CS-3955, compounds described in WO 00/66112, WO 2004024697, WO 2004052862 WO 2006022454, WO 2006023400, WO 2006020415, WO 2006020891, WO 2006036816, US 2006069122A1, WO 2006034001 WO 2006028896, WO 2006048862, WO 2006074426, US 2006160860, WO 2006076131, JP 2006188445, WO 2006090853 WO 2006096444, US 2006281712A1, WO 2007008539, US 0060293324A1, WO 2006117011, WO 2007022385, and WO 2007027999.

Examples of the fusion inhibitor include T-20 (pentafuside, Enfuvirtide, Fuseon (trade names)), T-1249 and the like.

Examples of the HIV integrase inhibitor include Equisetin, Temacrazine, MK0518 (Raltegravir), PL-2500, V-165, NSC-618929, L-870810, and L-708906 analog, S-1360, 1838, and the like.

The Short Interfering short-interfering RNAs targeting a HIV-related factor include those which target a gene of a HIV-related factor. Examples of the HIV-related factors include reverse transcriptase, protease, chemokine (CCR2, CCR3, CCR4, CCR5, CXCR4, etc.), CD4, HIV (HIV1, HIV2, etc.) and the like. Examples of the HIV-associated short interfering RNA include GPs-0193, HGTV-43, GEM-132, GEM-92, GEM-93, HYB-0184, GEM-91, UL36ANTI, ISIS-2922, ISIS-14803, GPI-2A, R-95288, and VRX-496.

Examples of the vaccine of HIV include Inflexal V, Vacc-4x, Vacc-5q, Typhim Vi, HBV-ISS, EP-1043, Tat Toxoid, IR-103, Remune, Flumist, AIDSVAX, Therapore-P24, and the like.

The conventional clinical dosage of typical reverse transcriptase inhibitors and protease inhibitors is, for example, as described below, but is not limited thereto in the present invention.

Zidovudine: 100 mg capsule, three times per day in a dosage of 200 mg; 300 mg tablet, twice per day in a dosage of 300 mg;

Didanosine: 25 to 200 mg tablet, twice per day in a dosage of 125 to 200 mg;

Zalcitabine: 0.375 mg to 0.75 mg tablet, three times per day in a dosage of 0.75 mg;

Stavudine: 15 to 40 mg capsule, twice per day in a dosage of 30 to 40 mg;

Lamivudine: 150 mg tablet, twice per day in a dosage of 150 mg;

Abacavir: 300 mg tablet, twice per day in a dosage of 300 mg;

Nevirapine: 200 mg tablet, once per day for 14 days in a dosage of 200 mg, followed by twice per day;

Delavirdine: 100 mg tablet, three times per day in a dosage of 400 mg;

Efavirenz: 50 to 200 mg capsule, once per day in a dosage of 600 mg;

Indinavir: 200 to 400 mg capsule, three times per day in a dosage of 800 mg;

Ritonavir: 100 mg capsule, twice per day in a dosage of 600 mg;

Nelfinavir: 250 mg tablet, three times per day in a dosage of 750 mg;

Saquinavir: 200 mg capsule, three times per day in a dosage of 1,200 mg;

Amprenavir: 50 to 150 mg tablet, twice per day in a dosage of 1,200 mg.

Examples of the other drugs for complementation and/or enhancement of the preventive and/or therapeutic effects of the compound of the present invention against asthma include antihistaminic agents, antiallergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants, and the like.

Examples of the antihistaminic agents include diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine and the like.

Examples of the chemical mediator release inhibitors include disodium cromoglycate, tranilast, amlexanox, repirinast, ibudilast, pemirolast potassium, tazanolast, nedocromil, cromoglicate, israpafant and the like.

Examples of the histamine antagonists include ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine and the like.

Examples of the thromboxane synthetase inhibitors include ozagrel hydrochloride imitrodast sodium and the like.

Examples of the thromboxane antagonists include seratrodast, ramatroban, domitroban calcium hydrate, KT-2-962 and the like.

Examples of the Th2 cytokine inhibitors include suplatast tosilate and the like.

Examples of the steroids include, for example, external medicine such as clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone propionate, clobetasone butyrate, prednisolone, beclomethasone propionate, fludroxycortide, and the like.

Examples of the xanthine derivative include aminophylline, theophylline, doxophylline, cipamfylline, diprophylline, proxyphylline, and choline theophylline.

Examples of the sympathomimetic agents include epinephrine, ephedrine hydrochloride, dl-methylephedrine hydrochloride, methoxyphenamine hydrochloride, isoproterenol sulfate, isoproterenol hydrochloride, orciprenaline sulfate, chloroprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromate, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319 and the like.

Examples of the parasympathomimetic agents include ipratropium bromide, flutropium bromide, oxitropium bromide, cimetropium bromide, temiverine, tiotropium bromide, revatropate (UK-112166) and the like.

Examples of the vaccinotherapeutic agents include paspat, asthremedin, Broncasma Berna, CS-560 and the like.

Examples of the gold preparations include gold sodium thiomalate and the like.

Examples of the basic nonsteroidal anti-inflammatory drugs include tiaramide hydrochloride, tinoridine hydrochloride, epirizole, emorfazone and the like.

Examples of the 5-lipoxygenase inhibitors include zyleuton, docebenone, piriprost, SCH-40120, WY-50295, E-6700, ML-3000, TMK-688, ZD-2138, dalbufelone mesilate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 and the like.

Examples of the 5-lipoxygenase activation protein antagonists include MK-591, MK-886 and the like.

Examples of the leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, Amlexanox, E-6700 and the like.

Examples of the prostaglandins (hereinafter abbreviated to as PG) include PG receptor agonists, PG receptor antagonists and the like.

Examples of the PG receptor include PGE receptor (EP1, EP2, EP3, and EP4), PGD receptor (DP, CRTH2), PGF receptor (FP), PGI receptor (IP), TX receptor (TP) and the like.

Examples of the antitussive drugs include codeine phosphate, dihydrocodeine phosphate, oxymetebanol, dextromethorphan hydrobromate, pentoxyverine citrate, dimemorfan phosphate, oxeladin citrate, cloperastine, benproperine phosphate, clofedanol hydrochloride, fominoben hydrochloride, noscapine, tipepidine hibenzate, eprazinone hydrochloride, plantago herb extract and the like.

Examples of the expectorants include foeniculated ammonia spirit, sodium hydrogencarbonate, potassium iodide, bromhexine hydrochloride, cherry bark extract, carbocysteine, fudosteine, ambroxol hydrochloride, ambroxol hydrochloride sustained-release tablet, methylcysteine hydrochloride, acetylcysteine, L-ethylcysteine hydrochloride, tyloxapol and the like.

Examples of the other drugs for complementation and/or enhancement of the preventive and/or therapeutic effects against atopic dermatitis (urticaria, etc.) of the compound of the present invention include steroids, non-steroid anti-inflammatory drug (NSAID), immune inhibitor, prostaglandins, antiallergic agent, mediator release inhibitor, antihistaminic agent, forskolin preparation, phosphodiesterase inhibitor, cannabinoid-2 receptor stimulant and the like.

Examples of the other drugs for complementation and/or enhancement of the preventive and/or therapeutic effects against allergic diseases (allergic bronchopulmonary aspergillosis, allergic eoisinophilic gastroenteritis, etc.) of the compound of the present invention include antiasthmatic drug, inhaled steroid drug, inhaled β2 stimulant, methylxanthine-based stimulant, antiallergic agent, anti-inflammatory agent, anticholinergic agent, thromboxane antagonist, leukotriene antagonist, LTD4 antagonist, PAF antagonist, phosphodiesterase inhibitor, β2 agonist, steroid drug, mediator release inhibitor, eosinophile leukocytechemotaxis inhibitor, macrolide-based antibiotic, immune inhibitor, hyposensitization (allergen) injection and the like.

Examples of the antiasthmatic drug include theophylline, procaterol, ketotifen, azelastine and the like.

Examples of the inhaled steriod drug include beclomethasone, fluticasone, budesonide and the like.

Examples of the inhaled β2 stimulant include fenoterol, salbutamol, formoterol, salmeterol and the like.

Examples of the methylxanthine-based stimulant include theophylline and the like.

Examples of the antiallergic agent include ketotifen, terfenadine, azelastine, epinastine, suplatast, disodium cromoglycate and the like.

Examples of the anti-inflammatory agent include dichlofenac sodium, ibuprofen, indomethacin and the like.

Examples of the anticholinergic agent include ipratropium bromide, flutropium bromide, oxitropium bromide, tiotropium bromide and the like.

Examples of the thromboxane antagonist include ozagrel, seratrodast and the like.

Examples of the macrolide-based antibiotic include erythromycin, roxithromycin and the like.

Examples of the leukotriene antagonist include pranlukast, montelukast, zafirlukast, zyleuton and the like.

Examples of the immune inhibitor include cyclosporine, tacrolimus, FTY720, and the like.

Examples of the other drug for complementation and/or enhancement of the preventive and/or therapeutic effects against hepatitis of the compound of the present invention include liver hydrolysate preparation, polyenephosphatidylcholine, glycyrrhizin preparation, protoporphyrin sodium, ursodeoxycholic acid, steroids, anticholinergic agent, gastric antiacid, propagermanium, lipid peroxidase inhibitor, and mitochondrial benzodiazepine receptor antagonist.

Examples of the other drug for complementation and/or enhancement of the preventive and/or therapeutic effects against arthritis and rheumatoid arthritis of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, IL-6 inhibitor, interferon γ agonist, IL-1 inhibitor and the like.

Examples of the other drug for complementation and/or enhancement of the preventive and/or therapeutic effects against psoriasis of the compound of the present invention include steroids, vitamin D derivative and the like.

Examples of the other drug for complementation and/or enhancement of the preventive and/or therapeutic effects against rhinitis of the compound of the present invention include antihistaminic agent, mediator release inhibitor, thromboxane synthetase inhibitor, thromboxane $A_2$ receptor antagonist, leukotriene receptor antagonist, steroids, α adrenalin receptor stimulant, xanthine derivative, anticholinergic agent, prostaglandins, nitrogen monoxide synthetase inhibitor, $β_2$ adrenalin receptor stimulant, phosphodiesterase inhibitor, cannabinoid-2 receptor stimulant and the like.

Examples of the other drug for complementation and/or enhancement of the preventive and/or therapeutic effects against conjunctivitis of the compound of the present invention include leukotriene receptor antagonist, antihistaminic agent, mediator release inhibitor, non-steroid anti-inflammatory drug, prostaglandins, steroid drug, nitrogen monoxide synthetase inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against ulcerative colitis of the compound of the present invention include mesalazine, salazosulfapyridine, digestive tract ulcer therapeutic substance, anticholinergic agent, steroid drug, 5-lipoxygenase inhibitor, antioxidant, LTB4 antagonist, local anesthetic, immune inhibitor, protection factor enhancer, MMP inhibitor, and mitochondrial benzodiazepine receptor antagonist.

Examples of the other drug for complementation and/or enhancement of the preventive and/or therapeutic effects against diabetic complication of the compound of the present invention include sulfonyl urea-based hypoglycemic agent, biguanide-based drug, α-glucosidase inhibitor, ultrashort-acting insulinotropic agent, insulin drug, PPAR agonist, insulin sensitive enhancer having no PPAR antagonism, β3 adrenalin receptor agonist, aldose reductase inhibitor, dipeptidyl peptidase IV inhibitor and the like.

Examples of the sulfonyl urea-based hypoglycemic agent include acetohexamide, glibenclamide, gliclazide, glyclopyramide, chlorpropamide, tolazamide, tolbutamide, Glimepiride and the like.

Examples of the biguanide-based drug include buformin hydrochloride, metformin hydrochloride and the like.

Examples of the α-glucosidase inhibitor include acarbose, voglibose and the like.

Examples of the ultrashort-acting insulinotropic agent include nateglinide, repaglinide and the like.

Examples of the PPAR agonist include pioglitazone, troglitazone, rosiglitazone, JTT-501, and the like.

Examples of the insulin sensitive enhancer having no PPAR antagonism include ONO-5816, YM-440 and the like.

Examples of the β3 adrenalin receptor agonist include AJ9677, L750355, CP331648 and the like.

Examples of the aldose reductase inhibitor include epalrestat, fidarestat, zenarestat and the like.

Examples of the other drug for complementation and/or enhancement of the preventive and/or therapeutic effects against cancer (malignant tumor) and cancer metastasis of the compound of the present invention include anticancer agent (for example, MMP inhibitor, alkylation agent (for example, cyclophosphamide, melphalan, thiotepa, mytomycin C, busulfan, procarbazine hydrochloride, etc.), antimetabolite (for example, methotrexate, mercaptpurine, azathiopurine, fluorouracil, tegafur, cytarabine, azaserine, etc.), antibiotic (for example, mytomycin C, bleomycin, Peplomycin, doxorubicin hydrochloride, aclarubicin, daunorubicin, actinomycin D, etc.), mitosis inhibitor, platinum complex (for example, Cisplatin), plant-derived antineoplastic agent (for example, vincristine sulfate, vinblastine sulfate, etc.), anticancerous hormone (for example, methyltestosterone, testosterone propionate, testosterone enanthate, mepitiostane, fosfestrol, chlormadinone acetate, etc.), immunostimulant (for example, picibanil, krestin, etc.), and interferon (for example, IFNα, IFNα-2a, IFNα-2b, IFNβ, IFNγ-1a, etc.). Examples thereof include biologics capable of conducting T cell activation (for example, anti-CTLA-4 antibody, anti-PD-1 antibody, etc.), antiangiogenic agent (for example, bevacizumab, pegaptanib, SU-6668, vatalanib, ranibizumab, sorafenib, SU-11248, neovastat), etc.), and the like.

Examples of the other drug for complementation and/or enhancement of the preventive and/or therapeutic effects against immune disease (for example, autoimmune disease, transplanted organ rejection, etc.) of the compound of the present invention include immune inhibitor (for example, cyclosporine, tacrolimus, FTY720, etc.) and the like.

Examples of the other drug for complementation and/or enhancement of the preventive and/or therapeutic effects against dementia such as Senile dementia with Alzheimer's type of the compound of the present invention include acetylcholine esterase inhibitor, nicotinic receptor modifier, cerebral ameliorator, monoamineoxidase inhibitor, vitamin E, aldose reductase inhibitor and the like.

Examples of the other drug for complementation and/or enhancement of the preventive and/or therapeutic effects against epilepsia of the compound of the present invention include phenyloin, trimethadione, ethosuximide, carbamazepine, phenobarbitone, primidone, acetazolamide, sultiame, sodium valproate, clonazepam, diazepam, nitrazepam and the like.

Examples of the other drug for complementation and/or enhancement of the preventive and/or therapeutic effects against arteriosclerosis of the compound of the present invention include HMG-CoA reductase inhibitor, fibrates, probucol preparation, anion-exchange resin, EPA preparation, nicotinic acid preparation, MTP inhibitor, other anti-high cholesterol agent, EDG-2 antagonist and the like.

Examples of the other drug for complementation and/or enhancement of the effects when the compound of the present invention is used in a regeneration therapy include cytokines and various growth factors, for example, various CSFs (for example, G-CSF, GM-CSF, etc.), various interleukins (for example, IL-3,6,7,11, 12, etc.), EPO, TPO, SCF, FLT3 ligand, MIP-1α and the like.

Examples of the other drug for complementation and/or enhancement of the preventive and/or therapeutic effects against retinopathy of the compound of the present invention include antiangiogenic agent (for example, bevacizumab, pegaptanib, SU-6668, vatalanib, ranibizumab, sorafenib, SU-11248, neovastat, etc.) and the like.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systematically or locally, in an oral or parenteral dosage form.

The dosage of the pharmaceutical preparation varies depending on the age, body weight, symptom, the desired therapeutic effect, the route of administration and duration of treatment. For the human adult, the dosage per person is between 1 ng and 1000 mg, by oral administration, up to several times per day, between 0.1 ng and 100 mg, by parenteral administration, or continuous administration 1 hour to 24 hours per day from vein.

As a matter of course, since the dosage varies under various conditions as is described above, the dosage may be sometimes sufficient which is smaller than the above range, or sometimes the dosage must be more than the above range.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants and the like for parenteral administration.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium carboxymethyl cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxylpropylmethy cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, and flavoring agent.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, and flavoring agents.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, and flavoring agent.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, and flavoring agent.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, and flavoring agent.

A propellant, an inhalant, and a spray may contain, in addition to a diluent used commonly, a stabilizer such as sodium hydrogensulfite and a buffer capable of imparting isotonicity, for example, an isotonicity such as sodium chloride, sodium citrate or citric acid.

An injection for parenteral administration includes all injections and also includes a drop. For example, it includes intramuscular injection, subcutaneous injection, endodermic injection, intraarterial injection, intravenous injection, intraperitoneal injection, intraspinal injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phosphoate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.) These ophthalmic solutions are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An inhalant for parenteral administration includes aerozol, inhalation powder, and inhalation solution, and the inhalation solution may be such a configuration that it is used after dissolving in water or other suitable medium at the point of use.

These inhalants are prepared according to a known method.

For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

Designation of the compound of the present invention is described below.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature. For example, a compound wherein $A^1$ and $A^2$ represent an imidazol-2-yl group, $M^{42}$ represents an ethoxycarbonylmethyl group, $B^1$ and $B^2$ represent a methylene group, G represents a carbon atom, E represents a 1,4-phenylene group, L represents —$CH_2$—, J represents 8-cyclohexyl-2,8-diazaspiro[4.5]dec-2-yl group, p1 represents 0, and p2 represents 1, namely, a compound represented by the following formula:

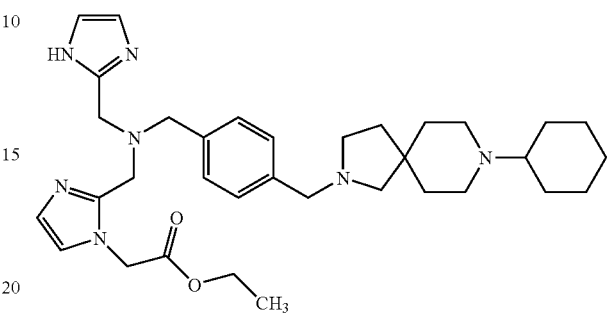

was designated as ethyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate.

EXAMPLES

The present invention is described in detail based on Examples, but the present invention is not limited thereto.

Crystallinity of the solid product was confirmed using a polarizing microscope.

The point of separation by chromatography and the solvent in the parentheses shown in TLC indicate a dissolution medium or an eluent used, and the proportion indicates a volume ratio.

NMR is a measured value of $^1$HNMR at 300 MHz and the solvent shown in the parentheses of NMR indicates a solvent used in the measurement.

Example 1 tert-butyl 8-cyclohexyl-2,8-diazaspiro[4.5]decane-2-carboxylate

Under an argon atmosphere, tert-butyl 2,8-diazaspiro[4.5]decane-2-carboxylate hydrochloride (3.2 g) and a 10% acetic acid-anhydrous N,N-dimethylformamide (50 mL) solution of cyclohexanone (1.9 mL) were stirred at room temperature for 4 hours. To the resultant solution, sodium tiacetoxy borohydride (5.2 g) was added. The reaction solution was stirred at room temperature for 15 hours. To the reaction solution, water (100 mL) and an aqueous 1N-sodium hydroxide solution (100 mL) were added. The aqueous layer was extracted twice with ethyl acetate. The organic layers were combined, washed with saturated saline and then dried over anhydrous sodium sulfate. The anhydrous sodium sulfate was removed by filtration and the solvent was concentrated under reduced pressure. The residue was purified by silica gel chromatography (ethyl acetate:methanol=1:0→8:2) to obtain the title compound having the following physical properties (3.7 g).

Rf 0.80 (chloroform:methanol: 28% ammonia water=40: 10:2);

NMR (CDCl$_3$): δ 1.00-1.38 (m, 6H), 1.46 (s, 9H), 1.48-1.96 (m, 10H), 2.24 (m, 1H), 2.20-2.48 (m, 2H), 2.52-2.64 (m, 2H), 3.08-3.22 m, 2H), 3.30-3.42 (m, 2H).

Example 2

8-cyclohexyl-2,8-diazaspiro[4.5]decane Dihydrochloride

To a methanol (10 mL) solution of the compound (3.7 g) obtained in Example 1, a 4N-hydrogen chloride-1,4-dioxane solution (10 mL) was added. The reaction solution was stirred at room temperature for 17 hours. The reaction solution was concentrated under reduced pressure and the residue was washed with tert-butylmethylether to obtain the title compound having the following physical properties (3.3 g).

Rf 0.39 (chloroform:methanol:28% ammonia water=40:10:2);

NMR (CD$_3$OD): δ 1.18-1.58 (m, 6H), 1.64-2.20 (m, 10H), 3.04-3.50 (m, 9H).

Example 3 tert-butyl (4-formylbenzyl)carbamate

To an ethyl acetate (50 mL) solution of tert-butyl [4-(hydroxymethyl)benzyl]carbamate (3.0 g), manganese dioxide (20.0 g) was added. The reaction solution was stirred at room temperature for one hour. The reaction solution was filtered through celite (trade name). The filtrate was concentrated under reduced pressure. The residue was purified by silica gel chromatography (n-hexane:ethyl acetate=8:2→7:3) to obtain the title compound having the following physical properties (2.3 g).

Rf 0.83 (chloroform:methanol=9:1);

NMR (CDCl$_3$): δ 1.47 (s, 9H), 4.40 (m, 2H), 4.95 (m, 1H), 7.45 (d, J=7.8 Hz, 2H), 7.86 (d, J=7.8 Hz, 2H), 10.00 (s, 1H).

Example 4 tert-butyl {4-[(8-cyclohexyl-2,8-diazaspiro[4.5]dec-2-yl)methyl]benzyl}carbamate The same procedure as in Example 1 was carried out, except that the compound obtained in Example 2 was used in place of tert-butyl diazaspiro[4.5]decane-2-carboxylate hydrochloride and the compound obtained in Example 3 was used in place of cyclohexanone in Example 1, the title compound having the following physical properties (2.4 g) was obtained.

Rf 0.17 (chloroform:methanol:28% ammonia water=90:10:1);

NMR (CD$_3$OD): δ 1.08-1.28 (m, 6H), 1.45 (s, 9H), 1.50-1.68 (m, 6H), 1.70-2.00 (m, 4H), 2.24 (m, 1H), 2.38 (s, 2H), 2.40-2.68 (m, 6H), 3.57 (s, 2H), 4.20 (s, 2H), 7.16-7.32 (m, 4H).

Example 5

1-{4-[(8-cyclohexyl-2,8-diazaspiro[4.5]dec-2-yl)methyl]phenyl}methaneamine Trihydrochloride The same procedure as in Example 2 was carried out, except that the compound obtained in Example 4 was used in place of the compound obtained in Example 1 in Example 2, the title compound having the following physical properties (349 mg) was obtained.

Rf 0.32 (chloroform:methanol:28% ammonia water=40:10:2);

NMR (CD$_3$OD): δ 1.18-1.58 (m, 6H), 1.60-1.22 (m, 10H), 3.00-3.56 (m, 7H), 3.65 (s, 2H), 4.16 (s, 2H), 4.42 (m, 2H), 7.52-7.62 (m, 2H), 7.66-7.80 (m, 2H).

Example 6

1-{4-[(8-cyclohexyl-2,8-diazaspiro[4.5]dec-2-yl)methyl]phenyl}-N-(1H-imidazol-2-ylmethyl)methaneamine To an anhydrous methanol (20 mL) solution of the compound (1.0 g) obtained in Example 5 and 1H-imidazole-2-carboaldehyde (401 mg), methyl orthoformate (0.46 mL) was added under an argon atmosphere. The reaction solution was stirred at room temperature for 15 hours. To the reaction solution, sodium borohydride (237 mg) and water (0.5 mL) were added, followed by stirring at room temperature for one hour. To the reaction solution, an aqueous 1N-sodium hydroxide solution (20 mL) was added. The solvent was concentrated under reduced pressure. The aqueous layer was extracted twice with dichloromethane. The organic layers were combined, washed with saturated saline and then dried over anhydrous magnesium sulfate. The anhydrous magnesium sulfate was removed by filtration and the filtrate was concentrated under reduced pressure. The residue was purified by silica gel chromatography (ethyl acetate:10% ammonia water-methanol=1:0→6:4) to obtain the title compound having the following physical properties (639 mg).

Rf 0.63 (chloroform:methanol:28% ammonia water=40:10:2);

NMR (CDCl$_3$): δ 1.00-1.28 (m, 6H), 1.48-1.90 (m, 10H), 2.22 (m, 1H), 2.35 (s, 2H), 2.40-2.60 (m, 6H), 3.49 (s, 2H), 3.79 (s, 2H), 3.95 (s, 2H), 6.99 (brs, 1H), 7.01 (brs, 1H), 7.20-7.38 (m, 4H).

Example 7

Ethyl (2-formyl-1H-imidazol-1-yl)acetate

To 1H-imidazole-2-carboaldehyde (2.0 g), N-methylpyrrolidone (25 mL) was added, followed by dissolution with heating. To the resultant solution, ethyl chloroacetate (11.1 mL) and potassium carbonate (2.9 g) were added. The reaction solution was stirred at room temperature for 14 hours. To the reaction solution, water (30 mL) was added. The aqueous layer was extracted twice with ethyl acetate. The organic layers were combined, washed with saturated saline and then dried over anhydrous sodium sulfate. The anhydrous sodium sulfate was removed by filtration and the solvent was concentrated under reduced pressure. The residue was purified by silica gel chromatography (dichloromethane) to obtain the title compound having the following physical properties (1.3 g).

Rf 0.63 (chloroform:methanol:28% ammonia water=90:10:1);

NMR (CDCl$_3$): δ 1.29 (t, J=7.2 Hz, 3H), 4.23 (q, J=7.2 Hz, 2H), 5.14 (s, 2H), 7.15 (d, J=0.9 Hz, 1H), 7.33 (d, J=0.9 Hz, 1H), 9.79 (s, 1H).

Example 8

Ethyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate

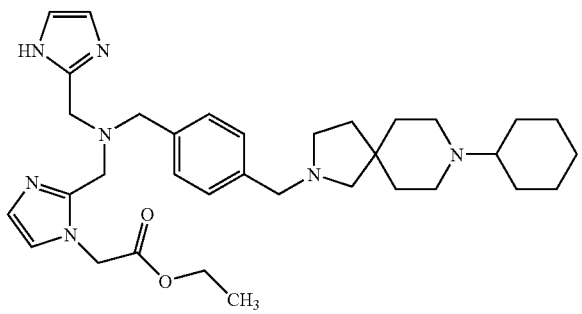 [SMILES: CCOC(=O)Cn1ccnc1CN(Cc1ccc(CN2CCC3(CCN(C4CCCCC4)CC3)C2)cc1)Cc1ncc[nH]1]

To a dichloromethane (5 mL) solution of the compound (98 mg) obtained in Example 6 and the compound (63 mg) obtained in Example 7, a triacetoxy borohydride resin (manufactured by ARGONUT Inc., product number 800414, 2.07 mmol/g, 224 mg) was added. The reaction solution was stirred at room temperature for 16 hours. The resin was removed by filtration and the filtrate was concentrated under reduced pressure. The residue was purified by silica gel column chromatography (dichloromethane) to obtain the title compound having the following physical properties (60.0 mg).

Description: amorphous;
Rf 0.82 (chloroform:methanol:28% ammonia water=40:10:2);
NMR (CD$_3$OD): δ 1.08-1.37 (m, 6 H), 1.23 (t, J=7.2 Hz, 3 H), 1.56-1.72 (m, 6 H), 1.75-1.95 (m, 4 H), 2.25-2.35 (m, 1 H), 2.39 (s, 2 H), 2.52-2.65 (m, 6 H), 3.50 (s, 2 H), 3.57 (s, 2 H), 3.58 (s, 2 H), 3.59 (s, 2 H), 4.11 (q, J=7.2 Hz, 2 H), 4.83 (s, 2 H), 6.88 (d, J=1.2 Hz, 1 H), 6.97-7.01 (m, 2 H), 7.02 (d, J=1.2 Hz, 1 H), 7.15-7.36 (m, 4 H).

Example 8(1) to Example 8(7)

The same procedure as in Example 7→Example 8 was carried out, except that the corresponding chloride was used in place of ethyl chloroacetate in Example 7, the following compounds were obtained.

Example 8(1)

Ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate

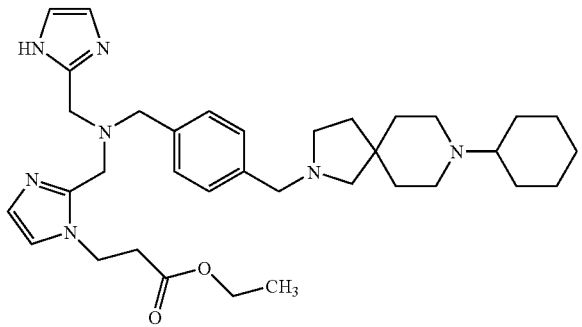 [SMILES: CCOC(=O)CCn1ccnc1CN(Cc1ccc(CN2CCC3(CCN(C4CCCCC4)CC3)C2)cc1)Cc1ncc[nH]1]

Description: amorphous;
Rf 0.71 (chloroform:methanol:28% ammonia water=40:10:2);
NMR (CD$_3$OD): δ 1.19 (t, J=7.2 Hz, 3 H), 1.23-1.35 (m, 6 H), 1.62-1.70 (m, 6 H), 1.77-1.97 (m, 4 H), 2.42 (s, 2 H), 2.43-2.51 (m, 1 H), 2.62 (t, J=6.9 Hz, 2 H), 2.65-2.74 (m, 6 H), 3.53 (s, 2 H), 3.58 (s, 2 H), 3.64 (s, 2 H), 3.65 (s, 2 H), 4.08 (q, J=7.2 Hz, 2 H), 4.15 (t, J=6.6 Hz, 2 H), 6.85 (d, J=1.5 Hz, 1 H), 6.98-7.02 (m, 2 H), 7.03 (d, J=1.5 Hz, 1 H), 7.13-7.35 (m, 4 H).

Example 8(2)

Ethyl 4-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)butanoate Description: amorphous;
Rf 0.77 (chloroform:methanol:28% ammonia water=40:10:2);
NMR (CD$_3$OD): δ 1.22 (t, J=7.2 Hz, 3 H), 1.21-1.33 (m, 6 H), 1.60-1.70 (m, 6 H), 1.77-1.97 (m, 6 H), 2.16 (t, J=7.2 Hz, 2 H), 2.41 (s, 2 H), 2.42-2.51 (m, 1 H), 2.61 (t, J=6.9 Hz, 2 H), 2.65-2.73 (m, 4 H), 3.52 (s, 2 H), 3.58 (s, 2 H), 3.62 (s, 2 H), 3.63-3.63 (m, 2 H), 3.91 (t, J=7.5 Hz, 2 H), 4.07 (q, J=7.2 Hz, 2 H), 6.87 (d, J=1.2 Hz, 1 H), 7.00-7.02 (m, 2 H), 7.03 (d, J=1.2 Hz, 1 H), 7.18-7.36 (m, 4 H).

Example 8(3)

Ethyl 2-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate Description: amorphous;
Rf 0.42 (chloroform:methanol: 28% ammonia water=90:10:1);
NMR (CDCl$_3$): δ 1.12-1.32 (m, 9 H), 1.51-1.90 (m, 13 H), 2.18-2.30 (m, 1 H), 2.36 (s, 2 H), 2.43-2.61 (m, 6 H), 3.39-3.73 (m, 8 H), 4.18 (q, J=7.2 Hz, 2 H), 4.96 (q, J=7.2 Hz, 1 H), 7.03-7.13 (m, 4 H), 7.21-7.34 (m, 4 H).

Example 8(4)

tert-butyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate Description: amorphous;
Rf 0.79 (chloroform:methanol:28% ammonia water=40:10:2);
NMR (CD$_3$OD): δ 1.05-1.36 (m, 6 H), 1.41 (s, 9 H), 1.53-1.69 (m, 6 H), 1.73-1.95 (m, 4 H), 2.25-2.35 (m, 1 H), 2.39 (s, 2 H), 2.50-2.64 (m, 6 H), 3.51 (s, 2 H), 3.56 (s, 2 H), 3.57 (s, 2 H), 3.60 (s, 2 H), 4.70 (s, 2 H), 6.89 (d, J=1.5 Hz, 1 H), 6.98-7.01 (m, 2 H), 7.01 (d, J=1.5 Hz, 1 H), 7.16-7.45 (m, 4 H).

Example 8(5)

Methyl 4-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)butanoate Rf 0.25 (dichloromethane:methanol:28% ammonia water=90:10:1);

NMR (CDCl₃): δ 1.00-1.31 (m, 6H), 1.50-1.90 (m, 10H), 1.95-2.08 (m, 2H), 2.16-2.30 (m, 3H), 2.35 (s, 2H), 2.40-2.52 (m, 4H), 2.54 (t, J=6.6 Hz, 2H), 3.44 (s, 2H), 3.56 (s, 2H), 3.62 (s, 2H), 3.65 (s, 2H), 3.68 (s, 3H), 3.85 (t, J=7.5 Hz, 2H), 6.90 (d, J=1.5 Hz, 1H), 7.00 (d, J=1.5 Hz, 1H), 7.07 (s, 1H), 7.11 (s, 1H), 7.23-7.34 (m, 4H).

Example 8(6)

Propyl 4-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)butanoate Rf 0.64 (ethyl acetate:methanol:28% ammonia water=80:20:2);
NMR (CDCl₃): δ 0.95 (t, J=7.5 Hz, 3H), 1.00-1.96 (m, 18H), 1.96-2.62 (m, 13H), 3.45 (s, 2H), 3.56 (s, 2H), 3.62 (s, 2H), 3.65 (s, 2H), 3.85 (t, J=7.2 Hz, 2H), 4.04 (t, J=6.9 Hz, 2H), 6.90 (d, J=1.2 Hz, 1H), 7.00 (d, J=1.2 Hz, 1H), 7.07 (s, 1H), 7.24 (s, 1H), 7.20-7.38 (m, 4H), 12.3 (s, 1H)

Example 8(7)

Isopropyl 4-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)butanoate Rf 0.64 (ethyl acetate:methanol:28% ammonia water=80:20:2);
NMR (CDCl₃): δ 1.00-1.92 (m, 16H), 1.24 (d, J=6.6 Hz, 6H), 1.94-2.60 (m, 13H), 3.45 (s, 2H), 3.56 (s, 2H), 3.62 (s, 2H), 3.65 (s, 2H), 3.85 (t, J=7.2 Hz, 2H), 5.01 (m, 1H), 6.90 (d, J=1.2 Hz, 1H), 7.00 (d, J=1.2 Hz, 1H), 7.07 (s, 1H), 7.25 (s, 1H), 7.20-7.38 (m, 4H), 12.3 (s, 1H).

Example 9

(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetic Acid

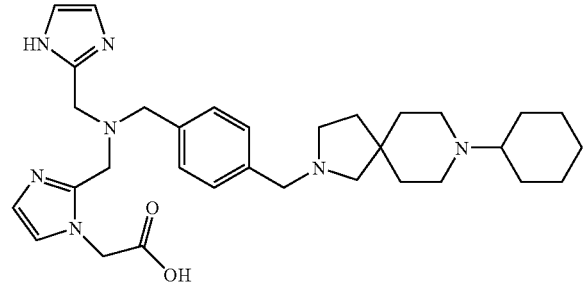 [SMILES: O=C(O)Cn1ccnc1CN(Cc1ccc(CN2CCC3(CCN(C4CCCCC4)CC3)C2)cc1)Cc1ncc[nH]1]

To an ethanol (7.6 mL) solution of the compound (50 mg) obtained in Example 8, an aqueous 2N-sodium hydroxide solution (1.0 mL) was added. The reaction solution was stirred at room temperature for 30 minutes. The reaction solution was neutralized with 2N-hydrochloric acid (1.0 mL) added thereto and the solvent was concentrated under reduced pressure. The residue was purified by silica gel column chromatography (dichloromethane:methanol=7:3) to obtain the title compound having the following physical properties (38 mg).
Description: amorphous;
Rf 0.28 (chloroform:methanol: 28% ammonia water=40:10:2);
NMR (CD₃OD): δ 1.11-1.50 (m, 6 H), 1.62-1.94 (m, 8 H), 1.97-2.10 (m, 2 H), 2.53 (s, 2 H), 2.70-2.82 (m, 2 H), 2.87-3.13 (m, 5 H), 3.46 (s, 2 H), 3.56 (s, 2 H), 3.59 (s, 2 H), 3.68 (s, 2 H), 4.37 (s, 2 H), 6.83 (d, J=1.2 Hz, 1 H), 6.95 (s, 2 H), 7.00 (d, J=1.2 Hz, 1 H), 7.29 (s, 4 H).

Example 9(1) to Example 9(3)

The same procedure as in Example 9 was carried out, except that the compounds obtained in Example 8(1) to (3) were used in place of the compound obtained in Example 8 in Example 9, the following compounds were obtained.

Example 9(1)

3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic Acid

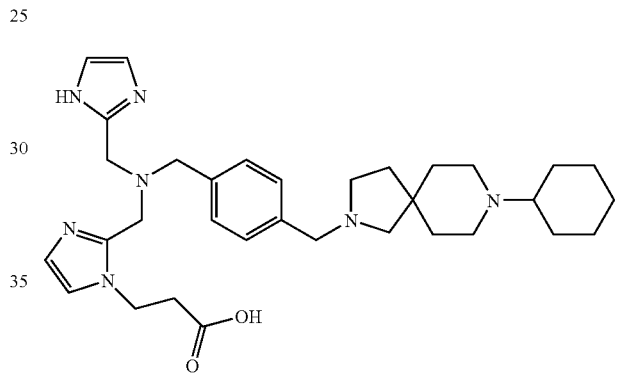

Description: amorphous;
Rf 0.33 (chloroform:methanol: 28% ammonia water=40:10:2);
NMR (CD₃OD): δ 1.04-1.54 (m, 6 H), 1.62-1.93 (m, 8 H), 1.99-2.18 (m, 2 H), 2.43 (t, J=7.2 Hz, 2 H), 2.59 (s, 2 H), 2.84 (t, J=6.3 Hz, 2 H), 2.90-3.20 (m, 5 H), 3.50 (s, 2 H), 3.61 (s, 2 H), 3.67-3.69 (m, 2 H), 3.74 (s, 2 H), 4.07 (t, J=7.2 Hz, 2 H), 6.81-6.85 (m, 1 H), 7.00-7.03 (m, 2 H), 7.06 (d, J=1.2 Hz, 1 H), 7.16-7.41 (m, 4 H).

Example 9(2)

4-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)butanoic Acid Description: amorphous;
Rf 0.36 (chloroform:methanol:28% ammonia water=40:10:2);
NMR (CD₃OD): δ 1.26-1.52 (m, 6 H), 1.58-1.96 (m, 8 H), 2.06 (t, J=7.2 Hz, 4 H), 1.99-2.05 (m, 2 H), 2.47 (s, 2 H), 2.81 (t, J=6.6 Hz, 2 H), 2.86-3.15 (m, 5 H), 3.49 (s, 2 H), 3.57 (s, 2 H), 3.67 (s, 4 H), 3.85 (t, J=7.5 Hz, 2 H), 6.85 (d, J=1.2 Hz, 1 H), 7.02 (s, 2 H), 7.03 (d, J=1.2 Hz, 1 H), 7.15-7.35 (m, 4 H).

Example 9(3)

2-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic Acid Description: amorphous;
Rf 0.36 (chloroform:methanol:28% ammonia water=90:10:1);
NMR (CD$_3$OD): δ 1.05-1.48 (m, 6 H), 1.48 (d, J=7.2 Hz, 3 H), 1.57-2.17 (m, 10 H), 2.47 (s, 2 H), 2.58-2.86 (m, 2 H), 2.84-3.16 (m, 5 H), 3.41-3.84 (m, 8 H), 4.66-4.89 (m, 1 H), 6.84 (d, J=1.2 Hz, 1 H), 6.96 (s, 2 H), 7.17 (d, J=1.2 Hz, 1 H), 7.19-7.36 (m, 4 H).

Example 10

Ethyl 3-(2-formyl-1H-imidazol-1-yl)propanoate

The same procedure as in Example 7 was carried out, except that ethyl 3-bromopropanoate was used in place of ethyl chloroacetate in Example 7, the title compound having the following physical properties (947 mg) was obtained.
Rf 0.83 (chloroform:methanol:28% ammonia water=90:10:1);
NMR (CDCl$_3$): δ 1.23 (t, J=6.9 Hz, 3H), 2.83 (t, J=6.3 Hz, 2H), 4.12 (q, J=6.9 Hz, 2H), 4.66 (t, J=6.3 Hz, 2H), 7.26 (m, 2H), 9.81 (s, 1H).

Example 11

N-benzyl1-(1H-imidazol-2-yl)methaneamine

The same procedure as in Example 6 was carried out, except that benzylamine was used in place of 1-{4-[(8-cyclohexyl-2,8-diazaspiro[4.5]dec-2-yl)methyl]phenyl}methaneamine trihydrochloride in Example 6, the title compound having the following physical properties (11.8 g) was obtained.
Rf 0.67 (chloroform:methanol:28% ammonia water=40:10:2);
NMR (CDCl$_3$): δ 3.81 (s, 2H), 3.94 (s, 2H), 6.99 (m, 2H), 7.20-7.39 (m, 5H).

Example 12

Ethyl 3-(2-{[benzyl(1H-imidazol-2-ylmethyl)amino]methyl}-1H-imidazol-1-yl)propanoate The same procedure as in Example 1 was carried out, except that the compound obtained in Example 11 was used in place of tert-butyl 2,8-diazaspiro[4.5]decane-2-carboxylate hydrochloride in Example 1, the title compound having the following physical properties (489 mg) was obtained.
Rf 0.92 (chloroform:methanol:28% ammonia water=40:10:2);
NMR (CDCl$_3$): δ 1.26 (t, J=7.2 Hz, 3H), 2.78 (t, J=6.9 Hz, 2H), 3.47 (s, 2H), 3.66 (s, 2H), 3.69 (s, 2H), 4.08-4.22 (m, 4H), 6.95 (d, J=1.5 Hz, 1H), 6.99 (d, J=1.5 Hz, 1H), 7.10 (s, 2H), 7.20-7.44 (m, 5H).

Example 13

Ethyl 3-(2-{[(1H-imidazol-2-ylmethyl)amino]methyl}-1H-imidazol-1-yl)propanoate

To an ethanol (5 mL) solution of the compound (489 mg) obtained in Example 12, 20%-palladium hydroxide/carbon (400 mg) was added under an argon atmosphere. The resultant solution was stirred under a hydrogen atmosphere at 60° C. for 2.5 hours. The reaction solution was cooled to room temperature and then filtered through celite (trade name). The filtrate was conentrated under reduced pressure. The residue was purified by silica gel column chromatography (ethyl acetate:10% ammonia water-methanol=1:0→8:2) to obtain the title compound having the following physical properties (248 mg).
Rf 0.41 (chloroform:methanol:28% ammonia water=40:10:2);
NMR (CDCl$_3$): δ 1.25 (t, J=7.2 Hz, 3H), 2.85 (t, J=6.9 Hz, 2H), 3.75 (s, 2H), 3.88 (s, 2H), 4.15 (q, J=7.2 Hz, 2H), 4.29 (t, J=6.9 Hz, 2H), 6.95 (brs, 1H), 6.99 (brs, 1H), 7.02 (m, 2H).

Example 14

Methyl 4-[(8-cyclohexyl-2,8-diazaspiro[4.5]dec-2-yl)methyl]benzoate

The same procedure as in Example 1 was carried out, except that the compound obtained in Example 2 was used in place of tert-butyl 2,8-diazaspiro[4.5]decane-2-carboxylate hydrochloride and methyl 4-formylbenzoate was used in place of cyclohexanone in Example 1, the title compound having the following physical properties (346 mg) was obtained.
Rf 0.74 (chloroform:methanol:28% ammonia water=40:10:2);
NMR (CDCl$_3$): δ 1.00-1.32 (m, 6H), 1.48-1.88 (m, 10H), 2.21 (m, 1H), 2.34 (s, 2H), 22.35-2.50 (m, 4H), 2.56 (t, J=6.6 Hz, 2H), 3.62 (s, 2H), 3.91 (s, 3H), 7.40 (brd, J=8.4 Hz, 2H), 7.99 (brd, J=8.4 Hz, 2H).

Example 15

4-[(8-cyclohexyl-2,8-diazaspiro[4.5]dec-2-yl)methyl]benzoic Acid

The same procedure as in Example 9 was carried out, except that the compound obtained in Example 14 was used in place of the compound obtained in Example 8 in Example 9, the title compound having the following physical properties (49 mg) was obtained.
Rf 0.28 (chloroform:methanol:28% ammonia water=40:10:2);
NMR (CDCl$_3$): δ 0.98-1.28 (m, 6H), 1.40-1.60 (m, 6H), 1.64-1.82 (m, 4H), 2.25 (s, 2H), 2.30 (m, 1H), 2.40-2.68 (m, 6H), 3.56 (s, 2H), 7.34 (d, J=7.8 Hz, 2H), 7.84 (d, J=7.8 Hz, 2H).

Example 16

Ethyl 3-(2-{[{4-[(8-cyclohexyl-2,8-diazaspiro[4.5]dec-2-yl)methyl]benzoyl}(1H-imidazol-2-ylmethyl)amino]methyl}-1H-imidazol-1-yl)propanoate To an anhydrous N,N-dimethylformamide (5 mL) solution of the compound (57 mg) obtained in Example 13 and the compound (49 mg) obtained in Example 15, N,N-diisopropylethylamine (0.047 mL) and N,N,N',N'-tetramethyluronium hexafluorophosphate (HATU) (103 mg) were added. The reaction solution was stirred at room temperature for 20 hours. To the reaction solution, an aqueous saturated sodium hydrogen carbonate solution (20 mL) was added. The aqueous layer was extracted twice with dichloromethane. The organic layers were combined, washed with saturated saline and then dried over anhydrous sodium sulfate. The anhydrous sodium sulfate was removed by filtration and the solvent was concentrated under reduced pressure. The residue was purified by thin layer chromatography (chloroform:methanol: 28% ammonia water=90:10:1) to obtain the title compound having the following physical properties (40 mg).

Description: amorphous;

Rf 0.68 (chloroform:methanol:28% ammonia water=40: 10:2);

NMR (DMSO-$D_6$): δ 1.10-1.32 (m, 6 H), 1.15 (t, J=7.2 Hz, 3 H), 1.42-1.59 (m, 6 H), 1.63-1.78 (m, 4 H), 2.11-2.24 (m, 1 H), 2.34 (s, 2 H), 2.36-2.57 (m, 6 H), 2.63-2.75 (m, 2 H), 3.57 (s, 2 H), 4.05 (q, J=7.2 Hz, 2 H), 4.12 (t, J=7.2 Hz, 2 H), 4.58 (s, 2 H), 4.66 (s, 2 H), 6.89 (d, J=1.2 Hz, 1 H), 6.90-6.98 (m, 2 H), 7.07 (d, J=1.2 Hz, 1 H), 7.24-7.34 (m, 2 H), 7.34-7.45 (m, 2 H).

Example 17

3-(2-{[{4-[(8-cyclohexyl-2,8-diazaspiro[4.5]dec-2-yl)methyl]benzoyl}(1H-imidazol-2-ylmethyl)amino]methyl}-1H-imidazol-1-yl)propionic Acid The same procedure as in Example 9 was carried out, except that the compound obtained in Example 16 was used in place of the compound obtained in Example 8 in Example 9, the title compound having the following physical properties (18 mg) was obtained.

Description: amorphous;

Rf 0.11 (chloroform:methanol:28% ammonia water=40: 10:2);

NMR ($CD_3OD$): δ 1.05-1.52 (m, 6H), 1.56-2.11 (m, 10H), 2.18-2.37 (m, 1 H), 2.41 (s, 2 H), 2.56-3.06 (m, 8 H), 3.55-3.73 (m, 2 H), 3.71-3.97 (m, 2 H), 4.48-4.81 (m, 4 H), 6.89-6.97 (m, 1 H), 7.00 (s, 2 H), 7.08-7.23 (m, 1 H), 7.25-7.53 (m, 4 H).

Example 18

Methyl 4-{[(1H-imidazol-2-ylmethyl)amino]methyl}benzoate

The same procedure as in Example 6 was carried out, except that methyl 4-(aminomethyl)benzoate was used in place of 1-{4-[(8-cyclohexyl-2,8-diazaspiro[4.5]dec-2-yl)methyl]phenyl}methaneamine trihydrochloride in Example 6, the title compound having the following physical properties (2.2 g) was obtained.

Rf 0.28 (chloroform:methanol:28% ammonia water=90: 10:1);

NMR ($CDCl_3$): δ 3.47 (s, 2H), 3.84 (s, 2H), 3.92 (s, 3H), 6.99 (m, 2H), 7.36-7.48 (m, 2H), 7.96-8.10 (m, 2H).

Example 19

Methyl 4-{[(tert-butoxycarbonyl)(1H-imidazol-2-ylmethyl)amino]methyl}benzoate

To a tetrahydrofuran (10 mL) solution of the compound (2.2 g) obtained in Example 18, triethylamine (2.5 mL), di-tert-butyldicarbonate (3.8 g) and hydroxyl aminehydrochloride (catalyst quantity) were added. The reaction solution was stirred at room temperature for 14 hours. To the reaction solution, water (30 mL) was added. The aqueous layer was extracted twice with ethyl acetate. The organic layers were combined, washed with saturated saline and then dried over anhydrous sodium sulfate. The anhydrous sodium sulfate was removed by filtration and the solvent was concentrated under reduced pressure. The residue was purified by silica gel column chromatography (n-hexane:ethyl acetate=8:2→2:8) to obtain the title compound having the following physical properties (2.4 g).

Rf 0.92 (chloroform:methanol:28% ammonia water=40: 10:2);

NMR ($CDCl_3$): δ 1.44 (s, 9H), 3.91 (s, 3H), 4.60-4.82 (m, 4H), 6.92 (d, J=1.5 Hz, 1H), 7.22-7.36 (m, 3H), 7.96-8.04 (m, 2H).

Example 20

4-{[(tert-butoxycarbonyl)(1H-imidazol-2-ylmethyl)amino]methyl}benzoic Acid

The same procedure as in Example 9 was carried out, except that the compound obtained in Example 19 was used in place of the compound obtained in Example 8 in Example 9, the title compound having the following physical properties (1.6 g) was obtained.

Rf 0.23 (chloroform:methanol:28% ammonia water=40: 10:2);

NMR ($CD_3OD$): δ 1.43 (s, 9H), 4.40-4.62 (m, 4H), 7.00 (s, 2H), 7.25 (m, 2H), 7.90-7.99 (m, 2H).

Example 21 tert-butyl {4-[(8-cyclohexyl-2,8-diazaspiro[4.5]dec-2-yl)carbonyl]benzyl}(1H-imidazol-2-ylmethyl)carbamate The same procedure as in Example 16 was carried out, except that the compound obtained in Example 20 was used in place of the compound obtained in Example 15 and the compound obtained in Example 2 was used in place of the compound obtained in Example 13 in Example 16, the title compound having the following physical properties was obtained. The resultant title compound was used for the subsequent reaction without being purified.

Rf 0.37 (chloroform:methanol:28% ammonia water=90: 10:1).

Example 22

1-{4-[(8-cyclohexyl-2,8-diazaspiro[4.5]dec-2-yl)carbonyl]phenyl}-N-(1H-imidazol-2-ylmethyl)methaneamine The same procedure as in Example 2 was carried out, except that the compound obtained in Example 21 was used in place of the compound obtained in Example 1 in Example 2, the title compound having the following physical properties (69 mg) was obtained.

Rf 0.75 (chloroform:methanol:28% ammonia water=40: 10:2);

NMR ($CD_3OD$): δ 1.04-1.40 (m, 6H), 1.46-2.00 (m, 10H), 2.18-2.80 (m, 5H), 3.40-3.88 (m, 8H), 6.97 (s, 2H), 7.38-7.52 (m, 4H).

Example 23

Ethyl (2-{[{4-[(8-cyclohexyl-2,8-diazaspiro[4.5]dec-2-yl)carbonyl]benzyl}(1H-imidazol-2-ylmethyl)amino]methyl}-1H-imidazol-1-yl)acetate The same procedure as in Example 8 was carried out, except that the compound obtained in Example 22 was used in place of the compound obtained in Example 6 in Example 8, the title compound having the following physical properties (55 mg) was obtained.

Description: amorphous;
Rf 0.84 (chloroform:methanol:28% ammonia water=40:10:2);
NMR (CD$_3$OD): δ 0.91-1.45 (m, 9 H), 1.48-2.11 (m, 10 H), 2.13-2.94 (m, 5 H), 3.41-3.74 (m, 10 H), 4.11 (q, J=6.9 Hz, 2 H), 4.73-4.96 (m, 2 H), 6.85-6.90 (m, 1 H), 6.94-7.09 (m, 3 H), 7.26-7.53 (m, 4 H).

Example 23(1) to Example 23(2)

The same procedure as in Example 21→Example 22→Example 23 was carried out, except that the corresponding amine was used in place of the compound obtained in Example 2 in Example 21, the following compounds were obtained.

Example 23(1)

Ethyl (2-{[{4-[(9-cyclohexyl-3,9-diazaspiro[5.5]undeca-3-yl)carbonyl]benzyl}(1H-imidazol-2-ylmethyl)amino]methyl}-1H-imidazol-1-yl)acetate Description: amorphous;
Rf 0.83 (chloroform:methanol:28% ammonia water=40:10:2);
NMR (CD$_3$OD): δ 1.05-1.38 (m, 9 H), 1.39-1.52 (m, 2 H), 1.53-1.72 (m, 6 H), 1.77-2.07 (m, 4 H), 2.31-2.56 (m, 1 H), 2.63-2.79 (m, 4 H), 3.28-3.46 (m, 2 H), 3.51-3.81 (m, 8 H), 4.12 (q, J=7.2 Hz, 1 H), 4.22 (q, J=7.2 Hz, 1 H), 4.61 (s, 1 H), 4.96 (s, 1 H), 6.83-6.91 (m, 1 H), 6.95-7.04 (m, 2 H), 7.05-7.16 (m, 1 H), 7.18-7.52 (m, 4 H).

Example 23(2)

Ethyl [2-({(1H-imidazol-2-ylmethyl)[4-({8-[(3-methyl-2-thienyl)methyl]-2,8-diazaspiro[4.5]dec-2-yl}carbonyl)benzyl]amino}methyl)-1H-imidazol-1-yl]acetate Description: amorphous;
Rf 0.85 (chloroform:methanol:28% ammonia water=40:10:2);
NMR (CD$_3$OD): δ 1.02-1.38 (m, 3 H), 1.43-2.04 (m, 6 H), 2.04-2.31 (m, 3 H), 2.24-2.82 (m, 4 H), 3.14-3.83 (m, 12 H), 3.88-4.26 (m, 2 H), 4.43-4.98 (m, 2 H), 6.54-6.94 (m, 2 H), 6.92-7.08 (m, 3 H), 7.09-7.30 (m, 1 H), 7.29-7.56 (m, 4 H).

Example 24

(2-{[{4-[(8-cyclohexyl-2,8-diazaspiro[4.5]dec-2-yl)carbonyl]benzyl}(1 H-imidazol-2-ylmethyl)amino]methyl}-1 H-imidazol-1-yl)acetic Acid The same procedure as in Example 9 was carried out, except that the compound obtained in Example 23 was used in place of the compound obtained in Example 8 in Example 9, the title compound having the following physical properties (25 mg) was obtained.

Description: amorphous;
Rf 0.23 (chloroform:methanol:28% ammonia water=40:10:2);
NMR (CD$_3$OD): δ 0.96-1.53 (m, 6 H), 1.59-2.14 (m, 10 H), 2.87-3.71 (m, 15 H), 4.32-4.48 (m, 2 H), 6.77-6.87 (m, 1 H), 6.91-6.98 (m, 2 H), 6.99-7.05 (m, 1 H), 7.37-7.49 (m, 4 H).

Example 24(1)

[2-({(1 H-imidazol-2-ylmethyl)[4-({8-[(3-methyl-2-thienyl)methyl]-2,8-diazaspiro[4.5]dec-2-yl}carbonyl)benzyl]amino}methyl)-1H-imidazol-1-yl]acetic Acid The same procedure as in Example 9 was carried out, except that the compound obtained in Example 23(2) was used in place of the compound obtained in Example 8 in Example 9, the title compound having the following physical properties was obtained.

Description: amorphous;
Rf 0.25 (chloroform:methanol:28% ammonia water=40:10:2);
NMR (CD$_3$OD): δ 1.54-1.98 (m, 6 H), 2.13-2.26 (m, 3 H), 2.50-2.85 (m, 4 H), 3.43-3.90 (m, 14 H), 4.43-4.49 (m, 2 H), 6.76-6.87 (m, 2 H), 6.95-7.02 (m, 2 H), 7.02-7.09 (m, 1 H), 7.15-7.30 (m, 1 H), 7.33-7.52 (m, 4 H).

Example 25

Diethyl 2,2'-[({4-[(8-cyclohexyl-2,8-diazaspiro[4.5]dec-2-yl)methyl]benzyl}imino)bis(methylene-1H-imidazole-2,1-diyl)]diacetate The same procedure as in Example 6→Example 8 was carried out, except that ethyl (2-formyl-1H-imidazol-1-yl)acetate was used in place of 1H-imidazole-2-carboaldehyde in Example 6, the title compound having the following physical properties was obtained.

Description: oily product;
Rf 0.34 (chloroform:methanol:28% ammonia water=90:10:1);
NMR (CD$_3$OD): δ 1.13-1.30 (m, 12 H), 1.57-1.69 (m, 6 H), 1.74-1.99 (m, 4 H), 2.33-2.44 (m, 3 H), 2.53-2.66 (m, 6 H), 3.48 (s, 2 H), 3.54-3.66 (m, 6 H), 4.08 (q, J=7.2 Hz, 4 H), 4.61 (s, 4 H), 6.90 (d, J=1.2 Hz, 2 H), 7.06 (d, J=1.2 Hz, 2 H), 7.12-7.24 (m, 2 H), 7.22-7.37 (m, 2 H).

Example 26

Ethyl [2-({{4-[(8-cyclohexyl-2,8-diazaspiro[4.5]dec-2-yl)methyl]benzyl}[(1-methyl-1H-imidazol-2-yl)methyl]amino}methyl)-1H-imidazol-1-yl]acetate The same procedure as in Example 6→Example 8 was carried out, except that 1-methyl-1H-imidazole-2-carboaldehyde was used in place of 1H-imidazole-2-carboaldehyde in Example 6, the title compound having the following physical properties was obtained.

Description: oily product;
Rf 0.55 (chloroform:methanol:28% ammonia water=90:10:1);
NMR (CD$_3$OD): δ 1.03-1.32 (m, 6 H), 1.22 (t, J=7.2 Hz, 3 H), 1.54-1.69 (m, 6 H), 1.73-1.97 (m, 4 H), 2.23-2.33 (m, 1 H), 2.38 (s, 2 H), 2.48-2.64 (m, 6 H), 3.31 (s, 3 H), 3.50 (s, 2 H), 3.57 (s, 2 H), 3.59 (s, 2 H), 3.63-3.65 (m, 2 H), 4.07 (q, J=7.2 Hz, 2 H), 4.64 (s, 2 H), 6.85 (d, J=1.5 Hz, 1 H), 6.89 (d, J=1.5 Hz, 1 H), 7.00 (d, J=1.5 Hz, 1 H), 7.04 (d, J=1.5 Hz, 1 H), 7.10-7.23 (m, 2 H), 7.22-7.35 (m, 2 H).

Example 27

[2-({{4-[(8-cyclohexyl-2,8-diazaspiro[4.5]dec-2-yl)methyl]benzyl}[(1-methyl-1H-imidazol-2-yl)methyl]amino}methyl)-1H-imidazol-1-yl]acetic Acid The same procedure as in Example 9 was carried out, except that the compound obtained in Example 26 was used in place of the compound obtained in Example 8 in Example 9, the title compound having the following physical properties was obtained.

Description: amorphous;

Rf 0.19 (chloroform:methanol:28% ammonia water=90:10:1);

NMR (CD$_3$OD): δ 1.16-1.40 (m, 6 H), 1.56-1.77 (m, 6 H), 1.78-2.05 (m, 4 H), 2.46 (s, 2 H), 2.57-2.65 (m, 1 H), 2.70 (t, J=6.9 Hz, 2 H), 2.75-2.84 (m, 4 H), 3.39 (s, 3 H), 3.50 (s, 2 H), 3.59-3.64 (m, 6 H), 4.32 (s, 2 H), 6.82 (d, J=1.5 Hz, 1 H), 6.85 (d, J=1.5 Hz, 1 H), 6.97 (d, J=1.5 Hz, 2 H), 7.10-7.22 (m, 2 H), 7.22-7.33 (m, 2 H).

Example 28 tert-butyl 3-(2-formyl-1H-imidazol-1-yl)propanoate

The same procedure as in Example 7 was carried out, except that tert-butyl 3-bromopropanoate was used in place of ethyl chloroacetate in Example 7, the title compound having the following physical properties was obtained.

Rf 0.40 (hexane:ethyl acetate=1:1);

NMR (CDCl$_3$): δ 1.40 (s, 9 H), 2.73 (t, J=6.32 Hz, 2 H), 4.62 (t, J=6.32 Hz, 2 H), 7.14-7.36 (m, 2 H), 9.81 (s, 1 H).

Example 29

3-(2-formyl-1H-imidazol-1-yl)propionic Acid

The same procedure as in Example 2 was carried out, except that the compound obtained in Example 28 was used in place of tert-butyl 8-cyclohexyl-2,8-diazaspiro[4.5]decane-2-carboxylate in Example 2, the title compound having the following physical properties was obtained.

Rf 0.10 (chloroform:methanol:28% ammonia water=40:1:2);

NMR (DMSO-d$_6$): δ 2.77 (t, J=6.96 Hz, 2 H), 4.55 (t, J=6.96 Hz, 2 H), 7.32 (d, J=0.92 Hz, 1 H), 7.67 (d, J=0.92 Hz, 1 H), 9.80 (s, 1 H).

Example 30

2-(dimethylamino)-2-oxoethyl 3-(2-formyl-1H-imidazol-1-yl)propanoate

The same procedure as in Example 7 was carried out, except that 2-chloro-N,N-dimethyl acetamide and the compound obtained in Example 29 were used in place of ethyl chloroacetate and 1H-imidazole-2-carboaldehyde in Example 7, the title compound having the following physical properties was obtained.

Rf 0.46 (chloroform:methanol=9:1);

NMR (CDCl$_3$): δ 2.84-2.95 (m, 8 H), 4.58-4.71 (m, 4 H), 7.17 (s, 1 H), 7.33 (s, 1 H), 9.71 (s, 1 H).

Example 31

2-(dimethylamino)-2-oxoethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate The same procedure as in Example 8 was carried out, except that the compound obtained in Example 30 was used in place of ethyl (2-formyl-1H-imidazol-1-yl)acetate in Example 8, the title compound having the following physical properties was obtained.

Rf 0.58 (ethyl acetate:methanol:28% ammonia water=40:10:2);

NMR (CDCl$_3$): δ 0.99-1.30 (m, 6 H), 1.51-1.67 (m, 6 H), 1.70-1.95 (m, 4 H), 2.16-2.29 (m, 1 H), 2.36 (s, 2 H), 2.42-2.50 (m, 4 H), 2.54 (t, J=6.87 Hz, 2 H), 2.93 (t, J=6.87 Hz, 2 H), 2.99 (s, 6 H), 3.51 (s, 2 H), 3.55 (s, 2 H), 3.61 (s, 2 H), 3.65 (s, 2 H), 4.17 (t, J=6.87 Hz, 2 H), 4.77 (s, 2 H), 6.98 (d, J=1.28 Hz, 1 H), 7.01 (d, J=1.28 Hz, 1 H), 7.06 (s, 1 H), 7.09 (s, 1 H), 7.26 (d, J=8.40 Hz, 2 H), 7.32 (d, J=8.40 Hz, 2 H), 12.02-12.10 (m, 1 H).

Example 31(1)

2-(4-morpholinyl)ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate The same procedure as in Example 30→Example 31 was carried out, except that N-(2-chloroethyl)morpholine hydrochloride was used in place of 2-chloro-N,N-dimethyl acetamide in Example 30, the title compound having the following physical properties was obtained.

Rf 0.43 (ethyl acetate:methanol:28% ammonia water=80:10:2);

NMR (CDCl$_3$): δ 1.00-1.31 (m, 6 H), 1.48-1.90 (m, 10 H), 2.16-2.28 (m, 1 H), 2.35 (s, 2 H), 2.42-2.50 (m, 8 H), 2.54 (t, J=6.77 Hz, 2 H), 2.59 (t, J=5.85 Hz, 2 H), 2.77 (t, J=6.59 Hz, 2 H), 3.48 (s, 2 H), 3.55 (s, 2 H), 3.61 (s, 2 H), 3.64-3.70 (m, 6 H), 4.10 (t, J=6.59 Hz, 2 H), 4.23 (t, J=5.85 Hz, 2 H), 6.97 (d, J=1.28 Hz, 1 H), 6.99 (d, J=1.28 Hz, 1 H), 7.06 (s, 1 H), 7.10 (s, 1 H), 7.26 (d, J=8.40 Hz, 2 H), 7.30 (d, J=8.40 Hz, 2 H), 12.08-12.25 (m, 1 H).

Example 32

1-{4-[(8-cyclohexyl-2,8-diazaspiro[4.5]dec-2-yl)methyl]phenyl}-N-[(1-{[2-(trimethylsilyl)ethoxy]methyl}-1H-imidazol-2-yl)methyl]methaneamine The same procedure as in Example 6 was carried out, except that 1-({[2-(trimethylsilyl)ethyloxy]methyl}-1H-imidazole-2-carboaldehyde (CAS Registry Number: 101226-42-0) was used in place of 1H-imidazole-2-carboaldehyde in Example 6, the title compound having the following physical properties was obtained.

Rf 0.48 (ethyl acetate:methanol:28% ammonia water=80:10:2);

NMR (CDCl$_3$): δ 0.02 (s, 9 H), 0.87 (t, J=8.40 Hz, 2 H), 1.03-1.32 (m, 6 H), 1.54-1.68 (m, 6 H), 1.73-1.92 (m, 4 H), 2.19-2.28 (m, 1 H), 2.35 (s, 2 H), 2.41-2.51 (m, 4 H), 2.55 (t, J=6.86 Hz, 2 H), 3.47 (t, J=8.40 Hz, 2H), 3.56 (s, 2 H), 3.80 (s, 2 H), 3.93 (s, 2 H), 5.31 (s, 2 H), 6.96 (s, 2 H), 7.29 (s, 4 H).

Example 33

Ethyl 3-[2-({{4-[(8-cyclohexyl-2,8-diazaspiro[4.5]dec-2-yl)methyl]benzyl}[(1-{[2-(trimethylsilyl)ethoxy]methyl}-1H-imidazol-2-yl)methyl]amino}methyl)-1H-imidazol-1-yl]propanoate The same procedure as in Example 8 was carried out, except that the compound obtained in Example 10 was used in place of ethyl (2-formyl-1H-imidazol-1-yl)acetate and the compound obtained in Example 32 was used in place of the compound obtained in Example 6 in Example 8, the title compound having the following physical properties was obtained.

Rf 0.60 (ethyl acetate:methanol:28% ammonia water=80:10:2);

NMR (CDCl₃): δ −0.08 (s, 9 H), 0.74 (t, J=7.50 Hz, 2 H), 1.04-1.32 (m, 9 H), 1.51-1.67 (m, 6 H), 1.71-1.90 (m, 4 H), 2.15-2.28 (m, 1 H), 2.30-2.57 (m, 10 H), 3.18 (t, J=7.50 Hz, 2 H), 3.54 (s, 2 H), 3.61 (s, 2 H), 3.71 (s, 2 H), 3.73 (s, 2 H), 3.96 (t, J=6.77 Hz, 2 H), 4.05-4.18 (m, 2 H), 4.92 (s, 2 H), 6.86 (d, J=1.28 Hz, 1 H), 6.90 (d, J=1.28 Hz, 1 H), 6.93 (d, J=1.28 Hz, 1 H), 6.96 (d, J=1.28 Hz, 1 H), 7.16 (d, J=7.20 Hz, 2 H), 7.24 (d, J=7.20 Hz, 2 H).

Example 34

3-[2-({{4-[(8-cyclohexyl-2,8-diazaspiro[4.5]dec-2-yl)methyl]benzyl}[(1-{[2-(trimethylsilyl)ethoxy]methyl}-1 H-imidazol-2-yl)methyl]amino}methyl)-1H-imidazol-1-yl]propanoate The same procedure as in Example 9 was carried out, except that the compound obtained in Example 33 was used in place of the compound obtained in Example 8 in Example 9, the title compound having the following physical properties was obtained.

Rf 0.28 (dichloromethane:methanol:28% ammonia water=80:10:2);

NMR (CD₃OD): δ −0.05 (s, 9 H), 0.71 (t, J=7.96 Hz, 2 H), 1.05-1.40 (m, 6 H), 1.60-1.73 (m, 6 H), 1.76-2.01 (m, 4 H), 2.26 (t, J=7.04 Hz, 2 H), 2.40-2.55 (m, 1 H), 2.45 (s, 2 H), 2.64 (t, J=6.77 Hz, 2 H), 2.68-2.75 (m, 4 H), 3.21 (t, J=7.87 Hz, 2 H), 3.51 (s, 2 H), 3.61 (s, 2 H), 3.64 (s, 2 H), 3.70 (s, 2 H), 3.92 (t, J=7.04 Hz, 2 H), 5.09 (s, 2 H), 6.83 (d, J=1.10 Hz, 1 H), 6.89 (d, J=1.10 Hz, 1 H), 7.11 (d, J=1.10 Hz, 1 H), 7.15 (d, J=1.10 Hz, 1 H), 7.17 (d, J=8.23 Hz, 2 H), 7.29 (d, J=8.23 Hz, 2H).

Example 35

1-{[(cyclohexyloxy)carbonyl]oxy}ethyl 3-[2-({{4-[(8-cyclohexyl-2,8-diazaspiro[4.5]dec-2-yl)methyl]benzyl}[(1-{[2-(trimethylsilyl)ethoxy]methyl}-1 H-imidazol-2-yl)methyl]amino}methyl)-1H-imidazol-1-yl]propanoate The same procedure as in Example 7 was carried out, except that cyclohexyl 1-chloroethyl carbonate (CAS Registry Number: 99464-83-2) and the compound obtained in Example 34 were used in place of ethyl chloroacetate and 1H-imidazole-2-carboaldehyde in Example 7, the title compound having the following physical properties was obtained.

Rf 0.58 (ethyl acetate:methanol:28% ammonia water=80:10:2);

NMR (CDCl₃): δ −0.03 (s, 9 H), 0.73 (t, J=7.50 Hz, 2 H), 0.99-1.98 (m, 29 H), 2.16-2.27 (m, 1 H), 2.34 (s, 2 H), 2.39-2.54 (m, 8 H), 3.18 (t, J=7.50 Hz, 2 H), 3.54 (s, 2 H), 3.61 (s, 2 H), 3.70 (s, 2 H), 3.72 (s, 2 H), 3.92-3.99 (m, 2 H), 4.57-4.69 (m, 1 H), 4.91 (s, 2 H), 6.73 (q, J=5.43 Hz, 1 H), 6.87 (d, J=1.28 Hz, 1 H), 6.89 (d, J=1.28 Hz, 1 H), 6.94 (d, J=1.28 Hz, 1 H), 6.95 (d, J=1.28 Hz, 1 H), 7.14 (d, J=8.10 Hz, 2 H), 7.25 (d, J=8.10 Hz, 2 H).

Example 36

1-{[(cyclohexyloxy)carbonyl]oxy}ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate

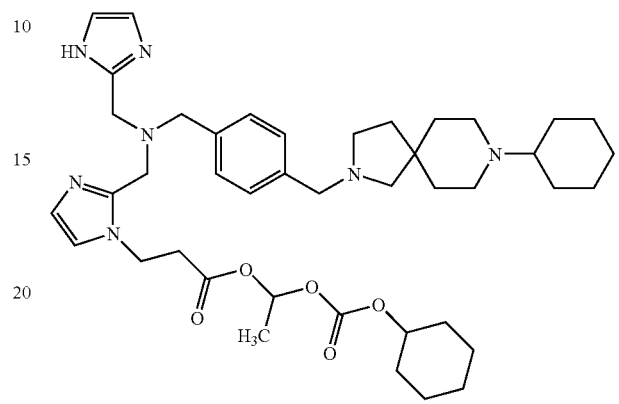

To the compound (142 mg) obtained in Example 35, trifluoroacetic acid (2 mL) was added. The reaction solution was stirred at 50° C. for 3 hours. The reaction solution was concentrated under reduced pressure and an aqueous saturated sodium carbonate was added to the residue. The aqueous layer was extracted with dichloromethane. The organic layers were combined, washed with saturated saline and then dried over anhydrous magnesium sulfate. The anhydrous sodium sulfate was removed by filtration and the filtrate was concentrated. The residue was purified by DM1020 silica gel chromatography (ethyl acetate:methanol=1:0→9:1) to obtain the title compound having the following physical properties (49 mg).

Rf 0.53 (ethyl acetate:methanol:28% ammonia water=80:10:2);

NMR (CDCl₃): δ 0.98-2.02 (m, 29 H), 2.16-2.29 (m, 1 H), 2.33-2.38 (m, 2 H), 2.44-2.50 (m, 4 H), 2.54 (t, J=6.95 Hz, 2 H), 2.80 (t, J=6.86 Hz, 2 H), 3.46 (s, 2 H), 3.56 (s, 2 H), 3.61 (s, 2 H), 3.65 (s, 2 H), 4.10 (t, J=6.86 Hz, 2 H), 4.56-4.68 (m, 1 H), 6.78 (q, J=5.37 Hz, 1 H), 6.94-6.99 (m, 2 H), 7.06 (s, 1 H), 7.10 (s, 1 H), 7.22-7.34 (m, 4 H), 12.07-12.23 (m, 1 H).

Example 37(1) to Example 37(3)

The same procedure as in Example 1→Example 8 was carried out, except that the corresponding carbonyl compound was used in place of cyclohexanone in Example 1 and the corresponding chloride was used in place of ethyl chloroacetate in Example 7, the following compounds were obtained.

Example 37(1)

Ethyl 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoate Rf 0.52 (dichloromethane:methanol:28% ammonia water=80:10:2);

NMR (CDCl₃): δ 0.87 (d, J=6.40 Hz, 6 H), 1.27 (t, J=7.14 Hz, 3 H), 1.50-1.65 (m, 6 H), 1.67-1.84 (m, 1 H), 1.94-2.07 (m, 4 H), 2.17-2.32 (m, 6 H), 2.36 (s, 2 H), 2.54 (t, J=6.77 Hz,

2 H), 3.45 (s, 2 H), 3.56 (s, 2 H), 3.63 (s, 2 H), 3.65 (s, 2 H), 3.85 (t, J=7.23 Hz, 2 H), 4.14 (q, J=7.07 Hz, 2 H), 6.91 (d, J=1.28 Hz, 1 H), 7.00 (d, J=1.28 Hz, 1 H), 7.07 (s, 1 H), 7.12 (s, 1 H), 7.21-7.36 (m, 4 H), 12.18-12.37 (m, 1 H).

Example 37(2)

Ethyl 4-(2-{[(4-{[8-(2,2-dimethylpropyl)-2,8-diazaspiro[4.5]dec-2-yl]methyl]benzyl)(1H-imidazol-2-ylmethyl)amino]methyl}-1H-imidazol-1-yl)butanoate Rf 0.58 (dichloromethane:methanol:28% ammonia water=80:10:2);
NMR (CDCl$_3$): δ 0.83 (s, 9 H), 1.27 (t, J=7.14 Hz, 3 H), 1.49-1.57 (m, 4 H), 1.58 (t, J=6.90 Hz, 2 H), 1.95-2.07 (m, 4 H), 2.25 (t, J=7.50 Hz, 2 H), 2.35 (s, 2 H), 2.36-2.46 (m, 4 H), 2.54 (t, J=6.95 Hz, 2 H), 3.45 (s, 2 H), 3.56 (s, 2 H), 3.63 (s, 2 H), 3.65 (s, 2 H), 3.86 (t, J=7.14 Hz, 2 H), 4.15 (q, J=7.14 Hz, 2 H), 6.92 (d, J=1.28 Hz, 1 H), 7.01 (d, J=1.28 Hz, 1 H), 7.08 (s, 1 H), 7.13 (s, 1 H), 7.27-7.35 (m, 4 H), 12.29 (s, 1 H).

Example 37(3)

Ethyl 4-(2-{[(4-{[8-(1-ethylpropyl)-2,8-diazaspiro[4.5]dec-2-yl]methyl]benzyl)(1 H-imidazol-2-ylmethyl)amino]methyl}-1H-imidazol-1-yl)butanoate

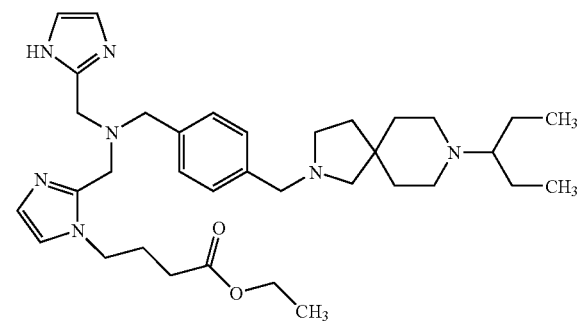 [SMILES: CCOC(=O)CCCn1ccnc1CN(Cc1ccc(CN2CCC3(CCN(C(CC)CC)CC3)C2)cc1)Cc1ncc[nH]1]

Rf 0.31 (dichloromethane:methanol:28% ammonia water=80:1:2);
NMR (CDCl$_3$): δ 0.87 (t, J=7.32 Hz, 6 H), 1.21-1.33 (m, 5 H), 1.38-1.66 (m, 8 H), 1.92-2.14 (m, 3 H), 2.24 (t, J=7.23 Hz, 2 H), 2.35 (s, 2 H), 2.36-2.45 (m, 4 H), 2.54 (t, J=6.77 Hz, 2 H), 3.45 (s, 2 H), 3.56 (s, 2 H), 3.63 (s, 2 H), 3.64 (s, 2 H), 3.85 (t, J=7.50 Hz, 2 H), 4.14 (q, J=6.65 Hz, 2 H), 6.90 (d, J=1.28 Hz, 1 H), 7.00 (d, J=1.28 Hz, 1 H), 7.06 (s, 1 H), 7.11 (s, 1 H), 7.22-7.38 (m, 4 H), 12.17-12.35 (m, 1 H).

Example 38(1) to Example 38(3)

The same procedure as in Example 9 was carried out, except that the compounds obtained in Examples 37(1) to (3) were used in place the compound obtained in Example 8 in Example 9, the following compounds were obtained.

Example 38(1)

4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoic Acid Rf 0.32 (chloroform:methanol:28% ammonia water=40:10:2);
NMR (CD$_3$OD): δ 0.95 (d, J=6.59 Hz, 6 H), 1.61-2.00 (m, 9 H), 2.07 (t, J=7.04 Hz, 2 H), 2.41 (t, J=7.14 Hz, 2 H), 2.56-2.79 (m, 6 H), 2.92 (t, J=7.04 Hz, 2 H), 3.50 (s, 2 H), 3.57 (s, 2 H), 3.67 (s, 2 H), 3.76-3.82 (m, 2 H), 3.84 (t, J=7.50 Hz, 2 H), 6.85 (d, J=1.28 Hz, 1 H), 7.01 (s, 2 H), 7.04 (d, J=1.28 Hz, 1 H), 7.26 (d, J=8.40 Hz, 2 H), 7.31 (d, J=Hz, 2 H).

Example 38(2)

4-(2-{[(4-{[8-(2,2-dimethylpropyl)-2,8-diazaspiro[4.5]dec-2-yl]methyl]benzyl)(1H-imidazol-2-ylmethyl)amino]methyl}-1H-imidazol-1-yl)butanoic Acid Rf 0.39 (chloroform:methanol:28% ammonia water=40:10:2);
NMR (CD$_3$OD): δ 0.89 (s, 9 H), 1.55-1.91 (m, 8 H), 2.08 (t, J=Hz, 2 H), 2.19 (s, 2 H), 2.51-2.66 (m, 4 H), 2.84 (s, 2 H), 3.06 (t, J=6.95 Hz, 2 H), 3.50 (s, 2 H), 3.57 (s, 2 H), 3.67 (s, 2 H), 3.82 (t, J=7.80 Hz, 2 H), 3.93 (s, 2 H), 6.86 (d, J=1.28 Hz, 1 H), 7.01 (s, 2 H), 7.06 (d, J=1.28 Hz, 1 H), 7.30 (d, J=8.10 Hz, 2 H), 7.34 (d, J=8.10 Hz, 2 H).

Example 38(3)

4-(2-{[(4-{[8-(1-ethylpropyl)-2,8-diazaspiro[4.5]dec-2-yl]methyl]benzyl)(1H-imidazol-2-ylmethyl)amino]methyl}-1H-imidazol-1-yl)butanoic Acid

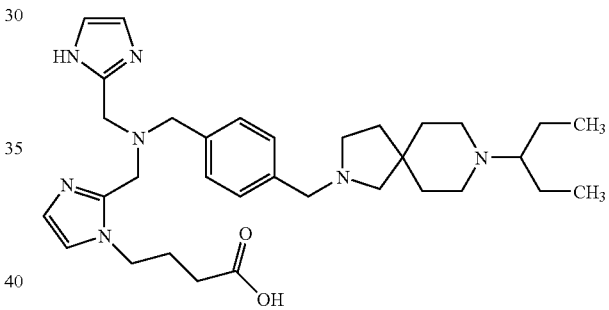

Rf 0.38 (chloroform:methanol:28% ammonia water=40:10:2);
NMR (CD$_3$OD): δ 0.96 (t, J=7.50 Hz, 6 H), 1.39-1.92 (m, 12 H), 2.07 (t, J=7.14 Hz, 2 H), 2.49-2.58 (m, 3 H), 2.72-2.89 (m, 6 H), 3.50 (s, 2 H), 3.58 (s, 2 H), 3.66 (s, 2 H), 3.72 (s, 2 H), 3.85 (t, J=7.20 Hz, 2 H), 6.84 (d, J=1.10 Hz, 1 H), 7.01 (s, 2 H), 7.03 (d, J=1.10 Hz, 1 H), 7.25 (d, J=8.40 Hz, 2H), 7.29 (d, J=8.40 Hz, 2 H).

BIOLOGICAL EXAMPLES

Efficacy of the compound of the present invention, for example the fact that the compound of the present invention has CXCR4 antagonistic activity, has been demonstrated by the following experiment. Also, the fact that the compound of the present invention has low toxicity, for example, the compound exerts less influence on the circulatory system and has a low risk of phospholipidosis, and oral absorption can be confirmed by carrying out the following tests.

A measuring method of the present invention was modified to improve accuracy and/or sensitivity of the measurement for evaluating the compound of the present invention. The detailed experimental methods are shown bellow.

As mentioned above, a more direct procedure is a screening a compound that prevents for HIV from binding to CXCR4, which is a receptor on CD4+ cell, on an assay system using HIV viruses. However, using HIV viruses for a large-scale screening is not practical due to its difficult handling. On the other hand, both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, in order to find a compound inhibiting absorption of HIV viruses to a cell that is a different mechanism from those of pre-existing anti-AIDS drugs (reverse transcriptase inhibitors and protease inhibitors), an assay system using an endogenous ligand for CXCR4, SDF-1 instead of HIV may be available.

Specifically, as a system of screening a compound that inhibits the binding between SDF-1 and CXCR4, for example a system of measuring the binding between iodine-labeled SDF-1 and a human T cell strain in which CXCR4 is known to be expressed is operable.

TEST METHODS

Test Example 1

Study for Inhibition of Binding Human SDF-1 to CEM Cells

To human T cell strain CEM cells in a binding buffer (containing HEPES and BSA), the test compound and $^{125}$I-SDF-1 (NEN) were added and the mixture was incubated at 4° C. for 60 minutes. The reacted CEM cells were rapidly filtrated with a GF/B membrane filter plate (Packard) to adsorb. The plate was washed with phosphate buffered saline (hereinafter abbreviated to PBS) three times and then dried. Microscint+20 (Packard) was added thereto. An amount of the radioactivity bound to the CEM cells was measured using Top Count (Packard) and inhibition (%) of the test compound was calculated according to the following equation:

$$\text{Inhibition} = \{(Et-Ea)/(Et-Ec)\} \times 100$$

wherein

Et: Amount of radioactivity when the test compound is not added,

Ec: Amount of radioactivity when non-radioactive SDF-1 (Pepro Tech) is added in an amount of 1,000 times as much as $^{125}$I-SDF-1 as a test compound, and Ea: Amount of radioactivity when the test compound is added.

All compounds of the present invention shown in Examples exhibited inhibition of 50% or more in a concentration of 10 μM. For example, IC$_{50}$ values for the compounds of Examples 9, 9(1), 36, 37(1), 37(3), 38(1) and 38(3) are as shown in Table 1 below.

TABLE 1

| Compound | IC 50 (μM) |
|---|---|
| Example 9 | 0.0048 |
| Example 9 (1) | 0.0034 |
| Example 36 | 0.0204 |
| Example 37 (1) | 0.0137 |
| Example 37 (3) | 0.0118 |
| Example 38 (1) | 0.0187 |
| Example 38 (3) | 0.0120 |

Test Example 2

Measuring of Influence of a Compound of the Present Invention on Blood Pressure and Heart Rate A rat was anesthetized with urethane (1.2 g/kg subcutaneous administration). After neck midline dissection, a catheter for measuring blood pressure was inserted into a right common carotid artery. Then, after dissecting inguinal region, a catheter for chemical injection was inserted into a femoral vein and fixed. A catheter for measurement of blood pressure was connected to a pressure transducer and then the pressure waveform was recorded on a thermal writing pen recorder through an amplifier for strain compression (AP-641G (manufactured by NIHON KOHDEN CORPORATION)). In this case, regarding a heart rate, a value through a cardiotachometer (AT-601G (manufactured by NIHON KOHDEN CORPORATION)) using the pressure waveform obtained from the amplifier for strain compression as a trigger was recorded on a thermal writing pen recorder. The test compound was dissolved in a 10% solubilizing agent/physiological saline solution (volume ratio of polyoxyethylene hydroxystearate:propylene glycol:physiological saline=7:3:190 (volume ratio)) so as to adjust the concentration to 0.1, 0.3, 1, 3 or 10 mg/mL to prepare solutions. Each solution was intravenous administered at 1 mL/kg through the caudal vein over about 10 seconds. Accumulative administration of stepwise increasing of a dosage was carried out to an individual.

Test Example 3

Artificial Lipid Membrane Binding Account by Using Biacore® S51 System (1) Liposome Preparation 10 mM of 1,2-dioleoyl-sn-glycero-3-phosphate monosodium salt (hereinafter abbreviated as DOPA) chloroform solution was evaporated to dryness by means of an aspirator, and 0.6 mL of PBS/5% dimethyl sulfoxide (hereinafter abbreviated as DMSO) was added. The solution was fully suspended by the vortex mixer, and the freezing and thawing were repeated for 5 times. Liposome was created by the liposome preparation instrument (manufactured by Avestin Inc.) and two syringes, and was diluted to 0.5 mM with PBS/5% DMSO just prior to immobilization.

(2) Preparation of Measurement Compound

38 μl of 1×PBS was added to 2 μl of a DMSO solution (10 mM), and the 360 μl of 1×PBS/5% DMSO was further added thereto and the 50 μM of final concentration in PBS/5% DMSO was prepared and measured.

(3) Analysis

All of the following analysis used Biacore® S51 system and the measurement conditions were set by Biacore S51 Control Soft.

The measurement temperature was set to be 37° C., and PBS/5% DMSO (pH 7.4) was used as a buffer. Series S Sensor Chip L1 was used for a sensor chip. DOPA was immobilized in one of the measuring spots on the sensor surface and the central spot was used as a reference.

Immobilization of liposome was conducted at a flow rate of 10 μL/min for about 3 minutes and then the compound was added at a flow rate of 30 μL/min and the interaction was measured. The measurement conditions are as follows:

Assay buffer: PBS/5% DMSO (pH 7.4)
Measurement temperature: 37° C.
Sensor chip: Series S Sensor Chip L1

Flow rate: 10 μL/min at the time of the liposome immobilization; 30 μL/min at the time of the measurement of interaction with the compound Regeneration: 20 mM CHAPS (3-[(3-cholamidopropyl)dimethylammonio]-1-propanesulfonate), isopropanol/aqueous 50 mM sodium hydroxide solution=40/60 (volume ratio) mixture (60 seconds)

(4) Data Processing

The data processing was conducted by means of method of Abdiche et al. (Analytical biochemistry, 328, 233-243 (2004)) by using Biacore S51 Evaluation Soft.

Regarding the value of binding response (RU) in which the value of reference was subtracted, it was divided by a sample molecular weight after minute error of the DMSO concentration included in the sample solution was corrected. In addition, the value obtained here was divided by an amount of capture at the time of the cycle because the value obtained here was proportional to the amount of capture of the liposome and the value was multiplied by a million to be considered as a corrected value (Corrected value=1,000,000×RU (test compound)/molecular quantity (test compound) RU (liposome)).

Propranolol, amiodarone, desipramine, imipramine and procaine were added as the controls, and it was recognized that the variation of the binding response was within about 10 to 15%.

(5) Determination

The compound wherein a value of the binding response after the correction was 150 or more was determined as positive.

As a result, it was found that the compound of the present invention, having a basic group substituted by a group having an acidic group, had a low phospholipidosis inductive effect in vitro experiment system. For example, corrected values of binding response (RU) of the compounds 9, 9(1), 38(1) and 38(3) are as described in the following table.

TABLE 2

| Compound | Corrected value of binding response (RU) | Determination |
| --- | --- | --- |
| Example 9 | 59.0 | Negative |
| Example 9 (1) | 52.0 | Negative |
| Example 38 (1) | 5.4 | Negative |
| Example 38 (3) | 98.9 | Negative |

Test Example 4

Investigation with Phospholipidosis Detecting System using Fluorescent Labeling Phospholipidosis Analog (1) Phospholipid Accumulation Measurement 100 μL/well as required (1 dose 2 wells) of cell suspension of CHL/IU (cell line derived from a Chinese hamster lung) ($7 \times 10^4$ cells/mL) prepared by MEM (minimum essential medium) culture medium was added to a 96-well plate (96-well clear-bottom plate), and cultured for about 24 hours. After culture, the supernatant of the 96-well plate was removed, and the 100 μL/well compounds of each concentration dissolved and suspended in an MEM including 25 μmol/L nitrobenzoxadiazole dipalmitoyl phosphatidylethanolamine (NBD-PE) (hereinafter abbreviated as a NPD-PE medium) were added and treated for about 24 hours. The treatment concentrations of each compound were set to be 6.25, 12.5, 25, 50 and 100 μmol/L. The positive control substance was set to be amiodarone hydrochloride, and the treatment concentrations were set to be 1.25, 2.5, 5, 10 and 20 μmol/L. In addition, 5-well untreated controls (only MEM) and 5-well NBD-PE controls (made by means of adding a 1/100 amount of DMSO to the NBD-PE culture medium) were set per compound, and cultured in the same manner. After finishing the culture, the cultures were washed twice with phosphate buffered saline (hereinafter abbreviated as PBS) (−) 100 μL/well, and the MEM (100 μL) was added to all of the treatment wells including two empty wells for WST-1 background controls and cultured for about a half hour. The fluorescence intensities of each well were measured by using a microplate reader (manufactured by Molecular Devices Inc., SPECTRA max M2; the excitation wavelength 485 nm/fluorescence wavelength 535 nm).

(2) Analysis

Using the average values of each dose×2 wells, a phospholipid increase rate (%) to the NBD-PE control was calculated by using the following calculating formula:

Rate of increase of pholipid accumulation (%)=100×{(test compound fluorescence intensity−non-treated control fluorescence intensity)/(NBD-PE control fluorescence intensity−non-treated control fluorescence intensity)}

(3) Cytotoxicity Assay 96-well plate measured in the phospholipid accumulation measurement was measured by means of Plate Reader (manufactured by Molecular Devices Inc., SPECTRA max M2) with the main wavelength of 450 nm and the correct wavelength of 690 nm to calculate a Pre value. An amount of 5 μL/well of Premix WS T-1 was added to each of the 96-hole plates by which Pre measurement was conducted. After culture for 2 to 4 hours, the 96-well plate was measured as well as the Pre measurement to calculate an Aft value. Then, the background control value was subtracted from the each measured value. A value which was calculated by subtracting the Pre value from the Aft value was used, then the cell growth rate (%) was calculated by using the following calculating formula:

Cell growth rate (%)=100×[(test substance OD)/(NBD-PE control OD)]

(4) Determination

A test dose that indicated value of 25% or more of the maximum phospholipid accumulation increase rate of amiodarone which was the positive control was determined as positive. In addition, the dose whose cell growth rate was equal to or less than 50% in the cytotoxicity assay was not used for determination of existence or nonexistence of a phospholipidosis inductive effect.

As a result, it was found that the compound of the present invention, having a basic group substituted by a group having an acidic group, had a low phospholipidosis inductive effect in vitro experiment system. For example, the rates of increase of pholipid accumulation (%) of the compounds 9, 9(1), 38(1) and 38(3) are as described in the following table.

TABLE 3

| Compound | Rate of increase of phopholipid accumulation (%) (compound dose: 100 μM) | Determination |
| --- | --- | --- |
| Example 9 | 10 | Negative |
| Example 9 (1) | 6 | Negative |
| Example 38 (1) | 8 | Negative |
| Example 38 (3) | 11 | Negative |

Test Example 5

Measurement of Maximum Plasma Level (Cmax)

A test compound is weighed, dissolved in WellSolve (trade name; manufactured by Celeste B Corporation) which is heated to 60° C. and adjusted to 20 mg/mL; thereafter, the test compound is diluted by 10 times with distilled water for injection, and further diluted by 2 times with saline solution, by which intravenously administered solution is eventually made. A test compound is weighed, dissolved in Solutol (trade name; manufactured by BASF-TAKEDA Vitamins Ltd.)/propylene glycol=7/3 which is heated to 60° C. and adjusted to 20 mg/mL; thereafter, the test compound is diluted by 10 times with distilled water for injection, by which orally administered solution is eventually made. Intravenous administration is performed by rapid single administration (n=3) of intravenously administered solution (1 mg/kg) from the tail vein of Crl:CD(SD) Rat (male, manufactured by CHARLES RIVER LABORATORIES JAPAN, INC). Oral administration is performed by forced administration (n=3) of orally administered solution (10 mg/kg) into the stomach of Crl:CD(SD) Rat (male, manufactured by CHARLES RIVER LABORATORIES JAPAN, INC.) using a sonde. The administration is conducted under fasting conditions; water is freely ingested. A 0.35 mL blood sample is taken from cervical vein by using Heparinized Syringe at 15 minutes, 30 minutes, 1 hour, 2 hours, 4 hours, 6 hours, 8 hours, and 24 hours after administration. The obtained blood is stored in ice, and after centrifugation at 12,000 rpm for 5 minutes, blood plasma is fractionated. The blood plasma is preserved at a temperature of −80° C. The sample of blood plasma preserved at a temperature of −80° C. is dissolved; inner standard solution (100 µL) and acetonitrile (2 mL) are added to the blood plasma sample 100 µL and stirred, and the sample is centrifuged at 2,500 rpm for 10 minutes. After the supernatant is evaporated to dryness by means of a centrifugal concentrator, 67% dimethyl sulfoxide solution (150 µL) is added to the residue and dissolves them again and 20 µL of the solution is analyzed by means of LC/MS/MS.

The analysis by means of LC/MS/MS should be performed, for example, under the following conditions:

[LC Conditions]

Measurement device: Waters 2795 (manufactured by Waters Corporation)

Analytical column: Unison UK-C18, 3.0 µm particle size, 2.0 mm×30 mm (manufactured by Imtakt Corporation)

Analytical column temperature: Room temperature

Flow rate: 200 µL/min

Moving bed: 5 mM IPC-PFAA-7 solution/acetonitrile (9/1 1/9)

[MS/MS Conditions]

Measurement device: Quatro micro API (manufactured by Micromass Communications Inc.)

Method for ionization: ES+

Capillary electric potential: 3.30 kV

Source temperature: 120° C.

Desolvation temperature: 350° C.

Multiplier: 650 V

The monitor ion which was suitable for each sample was selected.

The concentration transition in the rat blood plasma of the test compound is analyzed by means of non-compartment analysis method by using WinNonlin 4.0.1 (manufactured by Pharsight Corporation) to calculate the maximum blood concentration Cmax.

As a result, the maximum blood concentration Cmax of the compound of the present invention, having a group having an acidic group in a prodrug modification and an acidic group which is protected by a protective group, indicated good values. When the test compound is a prodrug to be metabolized after administration, the maximum blood concentration Cmax of the compound converted as a result of subjection to the reaction with an enzyme or gastric acid in the living body was measured. For example, when the compound of Example 36 as an ester of Example 9(1), the compound of Example 37(1) as an ester of Example 38(1) and the compound of Example 37(3) as an ester of Example 38(3) are administered, the maximum blood concentration Cmax of the hydroltyzates of Example 9(1), Example 38(1) and Example 38(3) was measured.

TABLE 4

| Compound to be evaluated | Compound to be converted in vivo | Cmax (ng/mL) |
| --- | --- | --- |
| Example 36 | Example 9(1) | 46.9 |
| Example 37(1) | Example 38(1) | 35.9 |
| Example 37(3) | Example 38(3) | 22.3 |

FORMULATION EXAMPLES

Formulation Example 1 diazaspiro (2-{[{4-[(8-cyclohexyl-2,8-diazaspiro[4.5]dec-2-yl)methyl]benzyl}(1H-imidazol-2-ylmethyl)amino]methyl)-1H-imidazol-1-yl)acetic acid (200 g), calcium carboxymethyl cellulose (disintegrant, 20.0 g), magnesium stearate (lubricants, 10.0 g) and microcrystalline cellulose (870 g) were mixed by a conventional method and then compressed to obtain 10,000 tablets each containing 20 mg of an active ingredient.

Formulation Example 2

(2-{[{4-[(8-cyclohexyl-2,8-diazaspiro[4.5]dec-2-yl)methyl]benzyl}(1H-imidazol-2-ylmethyl)amino]methyl)-1H-imidazol-1-yl)acetic acid (100 g), mannitol (2 kg) and distilled water (50 L) were mixed by a conventional method and filtered with a dust filter, and then each ampoule was filled with 5 mL of the obtained mixture and subjected to heat sterilization in an autoclave to obtain 10,000 ampoules each containing 10 mg of an active ingredient.

Industrial Applicability

The compound of the present invention has an antagonistic activity against CXCR4 and is therefore useful as a preventive and/or therapeutic agent for CXCR4-mediated diseases. For example, the compound of the present invention is useful as a preventive and/or therapeutic agent for inflammatory and immune diseases (for example, rheumatoid arthritis, arthritis, retinopathy, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

The invention claimed is:

1. A compound represented by formula (I-1):

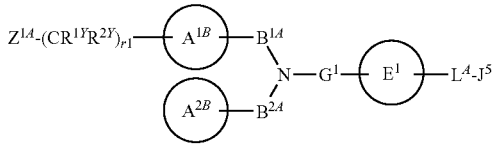
(I-1)

wherein ring $A^{1B}$ and ring $A^{2B}$ each independently represents an imidazole ring which may be substituted by a C1-8 aliphatic hydrocarbon group, an oxo group, or a C1-8 aliphatic hydrocarbon group substituted by a mono- or di-substituted amino group;

$B^{1A}$ and $B^{2A}$ each independently represents —$CH_2$—;

$G^1$ represents —CO—, or —$CH_2$—;

ring $E^1$ represents a benzene ring which may be substituted by a halogen atom, an —O—C 1-8 aliphatic hydrocarbon group, or a C1-8 aliphatic hydrocarbon group;

$L^A$ represents —CO— or —$CH_2$—;

$J^5$ represents

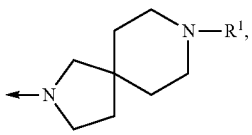

wherein an arrow binds to $L^A$, $R^1$ represents a hydrogen atom, a C4-7 monocyclic carbocyclic ring or a C1-8 alkyl group;

$Z^{1A}$ represents a carboxyl group which may be protected by a C1-15 alkyl group, a C2-10 alkenyl group, a C3-10 cycloalkenyl group, a C6-14 aryl group, a C7-16 aralkyl group or a (C3-8 cycloalkyl group)-(C1-4 alkyl group) which may be substituted by (1) aminocarbonyl group substituted with a C1-15 alkyl group, a C2-10 alkenyl group, a C3-10 cycloalkenyl group, a C6-14 aryl group, a C7-16 aralkyl group or a (C3-8 cycloalkyl group)-(C1-4 alkyl group), or (2) 5- or 6- membered heterocyclic group which may be substituted by a C1-15 alkyl group, a C2-10 alkenyl group, a C3-10 cycloalkenyl group, a C6-14 aryl group, a C7-16 aralkyl group or a (C3-8 cycloalkyl group)-(C1-4 alkyl group), and also have, in addition to a carbon atom, 1 to 4 hetero atom(s) selected from an oxygen atom, a sulfur atom and/or a nitrogen atom;

$R^{1Y}$ and $R^{2Y}$ each independently represents a hydrogen atom or a C1-8 aliphatic hydrocarbon group; and r1 represents an integer of 1 to 4, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group.

2. The compound according to claim 1, wherein formula (I-1) is formula (I-1-1):

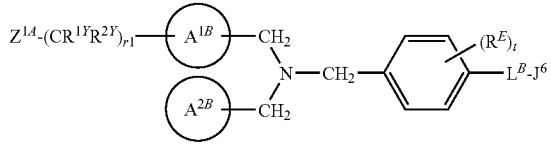
(I-1-1)

wherein $R^E$ represents a halogen atom, an —O—C1-8 aliphatic hydrocarbon group, or a C1-8 aliphatic hydrocarbon group;

t represents 0 or an integer of 1 to 2 and, when t represents 2, two $R^E$ may be the same or different;

$L^B$ represents —CO—, or —$CH_2$—;

$J^6$ represents:

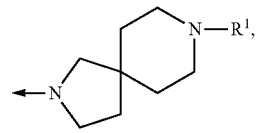

wherein an arrow binds to $L^B$, $R^1$ represents a hydrogen atom, a C4-7 monocyclic carbocyclic ring or a C1-8 alkyl group;

and other symbols are as defined in claim 1, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group.

3. The compound according to claim 1, which is (2-{[{4-[(8-cyclohexyl-2,8-diazaspiro [4.5]dec-2-yl)methyl]benzyl}(1H-imidazol-2-ylmethyl)amino]methyl}-1H-imidazol-1-yl)acetic acid, ethyl (2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)acetate, ethyl 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate, 3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propionic acid, 1-{[(cyclohexyloxy)carbonyl]oxy}ethyl3-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)propanoate, ethyl 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoate, 4-(2-{[(1H-imidazol-2-ylmethyl){4-[(8-isobutyl-2,8-diazaspiro[4.5]dec-2-yl)methyl]benzyl}amino]methyl}-1H-imidazol-1-yl)butanoic acid, ethyl 4-(2-{[(4-{[8-(1-ethylpropyl)-2,8-diazaspiro [4.5]dec-2-yl]methyl}benzyl)(1H-imidazol-2-ylmethyl)amino]methyl}-1H-imidazol-1-yl)butanoate, or 4-(2-{[(4-{[8-(1-ethylpropyl)-2,8-diazaspiro[4.5]dec-2-yl]methyl}benzyl)(1H-imidazol-2-ylmethyl)amino]methyl}-1H-imidazol-1-yl)butanoic acid, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group.

4. A pharmaceutical composition comprising a compound represented by formula (I-1) according to claim 1, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group.

5. The pharmaceutical composition according to claim 4, which is a CXCR4 antagonist.

6. The pharmaceutical composition according to claim 4, which is a therapeutic agent for CXCR4-mediated diseases, or an agent for regeneration therapy for the purpose of in vitro or in vivo amplification of stem cells for gene therapy as well as peripheral blood stem cell mobilization and tissue repair.

7. The pharmaceutical composition according to claim 6, wherein the CXCR4-mediated disease is human immunodeficiency virus infection, acquired immunodeficiency syndrome, cancer, cancer metastasis, rheumatoid arthritis, arthritis, retinopathy, macular degeneration, pulmonary fibrosis, asthma, ischemic diseases, systemic erythematosus, or transplanted organ rejection, or the agent for regeneration therapy is an agent for a transplantation medical treatment, or an agent for recruitment -of hematopoietic stem cells to peripheral blood.

8. The pharmaceutical composition according to claim 7, wherein the CXCR4-mediated disease is human immunodeficiency virus infection.

9. A pharmaceutical composition comprising a compound represented by formula (I-1) according to claim 1, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, short interfering RNA targeting a HIV-related factor, vaccine of HIV, and immunostimulant.

10. The pharmaceutical composition according to claim 5, which is a therapeutic agent for cancerous diseases.

11. A pharmaceutical composition comprising a compound represented by formula (I-1) according to claim 1, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group, and one or more kinds selected from anticancer drug, antimetabolite, antibiotic, antimitotic drug, platinum complex, plant-derived antineoplastic drug, anticancerous hormone, immunostimulant, interferon, biologics capable of performing T cell activation, and neovascularisation inhibitor.

12. A method for antagonizing CXCR4 in a mammal, comprising administering an effective dosage of a compound represented by formula (I-1) according to claim 1, a salt thereof, an N-oxide thereof, or a prodrug thereof which is a compound wherein a carboxy group of the compound represented by formula (I-1) is 1-{[(cyclohexyloxy)carbonyl]oxy}ethylesterified when the compound represented by formula (I-1) has a carboxy group to the mammal.

* * * * *